United States Patent
Grossman et al.

(10) Patent No.: US 11,236,339 B2
(45) Date of Patent: Feb. 1, 2022

(54) MODULATION OF GYS1 EXPRESSION

(71) Applicants: Ionis Pharmaceuticals, Inc., Carlsbad, CA (US); The Hospital for Sick Children, Toronto (CA)

(72) Inventors: Tamar R. Grossman, La Jolla, CA (US); Susan M. Freier, San Diego, CA (US); Berge Minassian, Toronto (CA); Saija Ahonen, Toronto (CA)

(73) Assignees: Ionis Pharmaceuticals, Inc., Carlsbad, CA (US); The Hospital for Sick Children, Toronto (CA)

( * ) Notice: Subject to any disclaimer, the term of this patent is extended or adjusted under 35 U.S.C. 154(b) by 0 days.

(21) Appl. No.: 16/306,831

(22) PCT Filed: Jun. 19, 2017

(86) PCT No.: PCT/US2017/038109
§ 371 (c)(1),
(2) Date: Dec. 3, 2018

(87) PCT Pub. No.: WO2017/219017
PCT Pub. Date: Dec. 21, 2017

(65) Prior Publication Data
US 2019/0194666 A1  Jun. 27, 2019

Related U.S. Application Data

(60) Provisional application No. 62/430,106, filed on Dec. 5, 2016, provisional application No. 62/351,396, filed on Jun. 17, 2016.

(51) Int. Cl.
| | | |
|---|---|---|
| C07H 21/04 | (2006.01) |
| C07H 21/02 | (2006.01) |
| C12N 15/113 | (2010.01) |
| A61K 31/7088 | (2006.01) |
| A61K 45/06 | (2006.01) |
| A61P 3/08 | (2006.01) |
| A61P 25/28 | (2006.01) |

(52) U.S. Cl.
CPC ...... *C12N 15/1137* (2013.01); *A61K 31/7088* (2013.01); *A61K 45/06* (2013.01); *A61P 3/08* (2018.01); *A61P 25/28* (2018.01); *C12N 15/113* (2013.01); *C12N 2310/11* (2013.01); *C12N 2310/315* (2013.01); *C12N 2310/321* (2013.01); *C12N 2310/3341* (2013.01); *C12N 2310/341* (2013.01); *C12N 2320/30* (2013.01)

(58) Field of Classification Search
CPC . A61K 31/713; C12N 15/113; C12N 2310/11
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,962,032 A | 10/1990 | Yoshida et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |

(Continued)

FOREIGN PATENT DOCUMENTS

| | | |
|---|---|---|
| WO | WO 2007/074428 | 7/2007 |
| WO | WO 2013/173637 A1 | 11/2013 |

(Continued)

OTHER PUBLICATIONS

Deleavey et al. (Chemistry & Biology, vol. 19, Issue 8, 2012, 937-954).*
Zois et al. (J. Mol. Med (Berl), Feb. 2016, 94(2), 137-154).*
Akman et al., "A novel mouse model that recapitulates adult-onset glycogenosis type 4" Hum Mol Genet (2015) 24(23): 6801-6810.
Bollen et al., "Specific features of glycogen metabolism in the liver" Biochem J (1998) 336: 19-31.
Branch et al., "A good antisense molecule is hard to find," TIBS (1998) 23:45-50.
Brown et al., "Brain glycogen re-awakened" J Neurochem (2004) 89(3): 537-552.

(Continued)

*Primary Examiner* — Amy H Bowman
(74) *Attorney, Agent, or Firm* — Michael Best & Friedrich LLP

(57) ABSTRACT

Provided herein are methods, compounds, and compositions for reducing expression of GYS1 in an individual. Such methods, compounds, and compositions are useful to treat, prevent, delay, or ameliorate a glycogen storage disease or disorder in an individual in need.

17 Claims, No Drawings

Specification includes a Sequence Listing.

(56) References Cited

U.S. PATENT DOCUMENTS

| | | |
|---|---|---|
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'o |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,825,328 B1 | 11/2004 | Scherer et al. |
| 6,906,182 B2 | 6/2005 | Ts'o et al. |
| 7,015,315 B1 | 3/2006 | Cook et al. |
| 7,034,133 B2 | 4/2006 | Wengel et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,871,768 B2 | 1/2011 | Scherer et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,450,060 B2 | 5/2013 | Scherer et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |

(56) References Cited

U.S. PATENT DOCUMENTS

| | | |
|---|---|---|
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,222,135 B2 | 12/2015 | Scherer et al. |
| 9,290,760 B2 | 3/2016 | Rajeev et al. |
| 2001/0053519 A1 | 12/2001 | Fodor et al. |
| 2003/0082807 A1 | 5/2003 | Wengel |
| 2003/0158403 A1 | 8/2003 | Manoharan et al. |
| 2003/0175906 A1 | 9/2003 | Manoharan et al. |
| 2003/0207841 A1 | 11/2003 | Kaneko et al. |
| 2003/0224377 A1 | 12/2003 | Wengel et al. |
| 2003/0228597 A1 | 12/2003 | Cowsert et al. |
| 2004/0143114 A1 | 7/2004 | Imanishi et al. |
| 2004/0171570 A1 | 9/2004 | Allerson et al. |
| 2004/0192918 A1 | 9/2004 | Imanishi et al. |
| 2005/0130923 A1 | 6/2005 | Bhat et al. |
| 2006/0148740 A1 | 7/2006 | Platenburg |
| 2007/0031844 A1 | 2/2007 | Khvorova et al. |
| 2008/0039618 A1 | 2/2008 | Allerson et al. |
| 2010/0190837 A1 | 7/2010 | Migawa et al. |
| 2010/0197762 A1 | 8/2010 | Swayze et al. |
| 2011/0123520 A1 | 5/2011 | Manoharan et al. |
| 2013/0130378 A1 | 5/2013 | Manoharan et al. |
| 2013/0203836 A1 | 8/2013 | Rajeev et al. |
| 2014/0107330 A1 | 4/2014 | Freier et al. |
| 2014/0228236 A1* | 8/2014 | Anastassiou ......... C12Q 1/6886 506/9 |
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2015/0344878 A1* | 12/2015 | Lu ....................... C12N 5/0619 514/44 A |
| 2019/0117794 A1* | 4/2019 | Nelson ........... C12Y 204/01011 |

FOREIGN PATENT DOCUMENTS

| | | |
|---|---|---|
| WO | WO 2015/179741 | 11/2015 |
| WO | WO 2015/192092 | 12/2015 |
| WO | WO 2016/161086 | 10/2016 |
| WO | WO 2017/040647 | 3/2017 |

OTHER PUBLICATIONS

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Clayton et al., "Antisense Oligonucleotide-mediated Suppression of Muscle Glycogen Synthase 1 Synthesis as an Approach for Substiate Reduction Therapy of Pompe Disease" Mol. Ther. Nucleic Acids (2014) 3(10): 1-11.

Crooke, St., et al., "Antisense Drug Technology" Second Edition, CRC Press (2008) Chapters 1-28.

Crooke et al., "Basic Principles of Antisense Therapeutics" Antisense Research and Application (1998) Chapter 1:1-50.

Depaoli-Roach et al. "Genetic depletion of the malin E3 ubiquitin ligase in mice leads to lafora bodies and the accumulation of insoluble laforin" J Biol Chem (2010) 285(33); 25372-25381.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Ganesh et al., "Targeted disruption of the Epm2a gene causes formation of Lafora inclusion bodies, neurodegeneration, ataxia, myoclonus epilepsy and impaired behavioral response in mice" Hum Mol Genet (2002) 11(11): 1251-1262.

Garcia-Cabrero et al., "Laforin and malin deletions in mice produce similar neurologic impairments" J Neuropathol Exp Neurol (2012) 71(5): 413-421.

Gautschi et al., "Activity of a novel bcl-2/bcl-xLbispecific antisense oligonucleotide against tumors of diverse histologic origins" J. Natl. Cancer Inst. (2001) 93:463-471.

International Search Report for PCT/US17038109 dated Sep. 28, 2017.

Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.

New England Biolabs 1998/99 Catalog (cover page and pp. 121 and 284).

Pederson et al., "Inhibiting glycogen synthesis prevents Lafora disease in a mouse model." Ann Neurol (2013) 74(2): 297-300.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Turnbull et al., "PTG Depletion Removes Lafora Bodies and Rescues the Fatal Epilepsy of Lafora Disease" PLOS Genetics (2011) 7(4):1-10.

Turnbull et al., "Glycogen Hyperphosphorylation Underlies Lafora Body Formation" Ann Neuro (2010) 68: 925-933.

Vilchez et al., "Mechanism suppressing glycogen synthesis in neurons and its demise in progressive myoclonus epilepsy." Nature Neuroscience (2007) 10(11): 1407-1413.

Wang et al. "Glycogen metabolism in tissues from a mouse modle of Lafora disease" Arch Biochem Biophys (2007) 457(2): 264-269.

Woolf et al., "Specificity of antisense oligonucleotides in vivo" PNAS (1992) 89: 7305-7309.

Zois et al., "Glycogen metabolism has a key role in the cancer microenvironment and provides new targets for cancer therapy" J. Mol. Med. (2016) 94(2):137-154.

Partial EP Search Report for 17814255.0 dated Jan. 2, 2020.

Duran et al., "Glycogen accumulation underlies neurodegeneration and autophagy impairment in Lafora disease" Hum Mol Gen (2014) 23: 3147-3156.

Grossman et al., "Antisense Oligonucleotide Therapy for Genetic Diseases" 2016 (1-13) Retrieved from: URL:https://apbdrf.org/wp-content/uploads/2016/12/Grossman-TR_APBDRF-2016-v2.pptx [on Nov. 29, 2019].

Grossman et al., "186: Antisense oligonucleotide therapy for the fatal epilepsy Lafora Disease" ASHG (2016) abstract p. 93.

Minassian et al., "Dr. Berge Minassian explains Lafora Disease in Miniature Wirehaired Dachshunds" YouTube (2016) Retrieved from: URL:https://www.youtube.com/watch?v=S-1 PiTaE6rw [on Dec. 2, 2019].

Minassian et al., "Scientists speak | Adult Polyglucosan Body Disease Research Foundation (APBDRF)" 2016: 1-8 Retrieved from: URL:http://web.archive.org/web/2016070118484p/https://www.apbdrf.org/resources/videos/scientists-speak [on Nov. 29, 2019].

Prakash et al., "Antisense Oligonucleotides Containing Conformationally Constrained 2',4'-(N-Methoxy)aminomethylene and 2',4'-Aminooxymethylene and 2'-O,4'-C-Aminomethylene Bridged Nucleoside Analogues Show Improved Potency in Animal Models" J Med Chem (2010) 53: 1636-1650.

Swayze et al., "Antisense Oligonucleotides containing locked nucleic acid improve potency but cause significant hepatotoxicity in animals" Nucleic Acids Research (2007) 35: 687-700.

Ahonen, "Therapy for Lafora Disease", Presentation, Jan. 2016, 9 pages.

* cited by examiner

SEQUENCE LISTING

<160> NUMBER OF SEQ ID NOS: 77

<210> SEQ ID NO 1
<211> LENGTH: 28000
<212> TYPE: DNA
<213> ORGANISM: Mus musculus

<400> SEQUENCE: 1

| | | | | | |
|---|---|---|---|---|---:|
| tggactatta | ctcaggcagg | aaaaaagagt | gaagctctga | ccccaacaca | cccaggaaga | 60 |
| ccactgagag | gtgctgagcg | agtgggctcc | cacataataa | agactgcacg | caggggctgg | 120 |
| agagaagggt | ggaggactct | tggccggtct | tccttccagg | ggaccgaggc | taaactgact | 180 |
| gcacacatgt | ggtggctcac | agctgactct | aactctggtt | ccggagatcc | aataccttct | 240 |
| tctggcctcc | tcaggcatag | acgtatccgg | agggaaaaca | cccatacaca | gaaaacatgg | 300 |
| tgaataaacc | ctcacgttga | aggattcttt | tttgttgttg | ttgctttggt | ttttttcgag | 360 |
| acagggtttc | tcagtgtagg | tagccctggc | tggccttgaa | cttagaaatc | cacctgcctc | 420 |
| tgcctcccaa | gtgctgggat | taaaggcatg | cgccaccact | gcccagcttg | ggttgaaggg | 480 |
| ttcttatatg | aagtatccaa | aagagatgcc | agaaatacaa | ggtagactag | tggttgccaa | 540 |
| aggctcgggg | agggaggtgt | ggggacactg | gagggtgcct | gctaggatgc | acttctgcag | 600 |
| ccactgggga | ggctgagtca | gaaagagtgc | ctcgagtctg | gagctagccc | aagctaaagg | 660 |
| gtgaaaacaa | gagaccgata | aatccaggcg | gtggacccct | gaacatcttt | tcctattttt | 720 |
| tacgaaccta | agaaaccaca | aagctaagcg | gccctcaacc | acagctcagg | atgcctcctc | 780 |
| ctggaatgga | acaaggcctt | ccaggatagc | ccacagccca | ggaccattta | ctgcctgtct | 840 |
| cttgctgtgg | gagccttcac | cttcctcttt | ttgtaggaga | ttgtgtggac | tgcaggagca | 900 |
| tgagaccccc | aaactactgt | cacacacagg | caagcaaagg | caggcccttc | ctcaccatgg | 960 |
| taacagcaac | agacgccact | gacctcccta | caacttgcct | gggcccaacc | ccagaatcaa | 1020 |
| ggacaccaca | aggccacaag | atttcttcac | tgggaagtct | gaggagctag | tgccaggccc | 1080 |
| aatatgcccg | gtctcacttc | ctgggcttta | ttcgctcact | gtaacattca | actaactgtg | 1140 |
| cgatggcaca | gacacgtgcc | ctaggtgagg | ttctgaaaaa | tacagtctct | ggacaagacc | 1200 |
| ccatgctctg | aacccagact | ctatttctct | tcctcactgt | cacactcctg | gcttcggaca | 1260 |
| cactttcctg | tgacctgtgc | tctcaagcac | acaacacaac | ttcccactta | ctaatcttcc | 1320 |
| ccagaagacc | agggtaccag | tctcagacct | cgcaggacac | tgggatgaga | ctttggaact | 1380 |
| ggtcactgac | tacatcaaga | ggcagacgaa | gtttccagaa | cgcattgtgg | gatgaaccac | 1440 |
| gactctgtca | ctccaggctc | tggctagtca | ctcattcaca | gagaaatctg | agtgtctaca | 1500 |
| tgactcttcc | atcagaccca | ggattctttc | tgttgttgtt | tctctgtgta | acccttggct | 1560 |
| gtcctggaac | tggctctgta | gaccaggcta | tcctcagact | cacagagatc | cacctgcctc | 1620 |
| tgcctcccaa | gtgcaggctt | tcactaccat | gcctgacatc | taggattctg | aatacattgt | 1680 |
| tgccttctct | actagcttct | aaagccacaa | tgaagctcct | tcctcagtgg | tcaatacact | 1740 |
| tcctccacat | ccaggagtcc | aggtccagcc | ctcttctatt | aggcccaggc | accctcccta | 1800 |
| gccctcctcc | tcctccaaac | caggcctcat | ccactgtgat | cgtccctccg | atctagggat | 1860 |
| tcaggctcta | gcctgcctac | ctcaaacaca | aggtgcaca | caccagcctg | cttccctcag | 1920 |
| accctggtat | cctctcctcc | caacacttcc | cacagatcca | tgtgtcctcc | caagccctcc | 1980 |
| ttggcgactt | cctcagcccc | cttccgtcag | attcatgcat | tctcctctgc | tctcttcctt | 2040 |
| tagacacatg | cattctcctc | tgtatccatt | gctcagactc | ggtgtcctca | gcatcctccc | 2100 |

```
tctgactcgg gagtactccc cagacctcct ccgtcaaacc aggcatcttc cttatcactc    2160
ctccctcaga tacaagagtc ctctccagct ccctccttca gactctctaa gaagggtcat    2220
tgtcggtcct ccacatgcac ccaacactta ccacggttgc catgatgcac accaaccgcc    2280
aatgcctcag cggaaacgga aatcggctag gagcgcggtc tttatcctct ctaggctccc    2340
ggtcatccag tcatctctat ggcccataag atatataaaa ttcctgtagg gggcgtacac    2400
taggccgcgc ccagcccgcg aggctaaatt ggaaagccgg tgttctgaat cccgggtggg    2460
ttcctgacgt ctcttgctcc tcctcctctt acctagcctc ctcccccctc cttccccccc    2520
gccctgcaac tgctaagtcc gattgcaaaa ttctgagcac attttgtagc aaccacacgt    2580
cctccacgat cccttccctc tctgtccaac cttcctcacc aaattgggcc tacagctgag    2640
attgacagct ctgttcacca atcacttcca tgctgcgtag aaacaagccc cgcccccgca    2700
gctccccagg agcctctggc caaggaaact ggattctatc cgccaataag tagacgcaat    2760
agcccccgcc cccagccgcc cgaccaatcg tgctagacca gcagggtggg cagtgcctcc    2820
tggcggccac gaggcttcac tgcagctgcc cgcccgattc agtgtctcag ctcaccctac    2880
ctgagtcgga gcgctctggg gcggggggtgc ggtcgtgcaa taggaagcgg agcgccttgc    2940
aagcttcccc tgggacaccc gctaactcta ccggtcacca agtctgctgc gttcccagcc    3000
gatctctctg gtttccagtt ttggtgctcg aagtcccctg cccgcagtag ccatgcctct    3060
cagccgcagt ctctctgtgt cctcgcttcc aggattggaa gactgggagg atgaattcga    3120
ccccgagaac gcagtgcttt tcgaggtggc ctggaggtg gccaacaagg gtgagaacgt    3180
cagcgttggt cccttgacca agaagggcag gcgaggatgg ggccccgaaa ctccgtttca    3240
gacgggaaaa gagttacgtg gaggagtctt gggtcctggg aaaagcgcct gtgacttctg    3300
tgtccttgtg aaggggctgg agtaggcgtc ctaggccctg gggggaaggg acaagagact    3360
actcttaaga tggaaggagg cttcaggttc tgcaatctag ggaagagggc actcagagaa    3420
agattcctgg gtcttgaagg gaggttttcg agggccgaga gacctgagat ctaaaagtgg    3480
aaggagttag tgcatctaag cccaaggaac actggagctt ttgggtctgt ggtccagagg    3540
acgtgactgt ggagttgggg tgttcctaaa ggttgggatt catggatttt tcaggggca    3600 tagcggacct gaaccagtgt aaagccaaga ggggcttgga gactcaaatt cttagataca    3660
aggtgggaaa gagttgggaa cttgaatgtc gagtttgaag gagcccaggg cctaagtcct    3720
ggcttcctat gtagtgaggt gcctccctcc ctgtggactg ggaaagctgg aagtcctaag    3780
ttggtcagga gctgggccct aggatgggag gaacccaccc acagtatgta tgggagatca    3840
ctagcttctc gctcatgaga aggctgggct gggaatccca gcagctgggc cttgtggatc    3900
tgaacatttc ctttttctgga tcctggggag aaagagacta ggtctctcag catgttggga    3960
gatggcagac tcaatgctgt gtactaccag ggtaccagtt tcaggtgaga aggctgagga    4020
cccagattcc taaatctgag gtggggtcac aggaggagca gggcccagca gtccctgtgt    4080
cccagcccag ggctagcatc gttaggggcc ctgaaggtgt ggaataataa gtcaagcttc    4140
cctcaggtaa ctgggtagct ggataggggc atgtaccatt tttcccactg catctgaaag    4200
tcaagagctt tagagccttc ctgctcctaa ttctctaaga attaggagac taaagagtgc    4260
ttcctgtgtc atgaccagga gtctaactgg agcctgctcc tccctcagca tctgatttc    4320 agtcccctct ctccataaac tcaagagggc tatcctcagg tttgcttttc cacgacccct    4380
accctccagt cccaacctcc cctgattccc aattataggt tcctgcccat tttctacccc    4440
```

```
aatactaccc acatacatcc cattacctgc caggtctcaa agctatggac caatggtggg    4500
gttgtctgtc cttttgcact ttggcccaca gtgggtggca tctacactgt gctgcagacg    4560
aaggcgaagg tgacagggga tgaatggggt gacaactact atctggtggg accatacacg    4620
gagcagggtg tgaggacgca ggtagagctc ctggagcccc caactccgga actgaagagg    4680
actttggatt ccatgaacag caagggttgt aaggtgggac acagccctac ccagggggt     4740
gggagtggga actgccagca ggggccctag caagaggtga agagaaggtg aatggaggc     4800
aggaggtgta gtcagaactt tcccagcagg cctagggaag aaagcgatag acgggtatag    4860
gatctggtga gtaggccag tgggtaccgg gtgtcagaaa ggccagatgg atggagatga     4920
atctcagcag agatcctcag acccagagac tacaaacaag ctggagctag cagaaagat     4980
agtcaaagct atgtgttctg tgcacacctg caatcccagg actacggagg cctaggcagg    5040
aggatctcgg tgtgttctaa gccagtctgg accacaagaa ggctctgtct cacagtaaat    5100
aaaataaaga tgagtagcca ggcagacaaa aagatggaat agagatgaag agaggagaac    5160
caggggaaaa gagtctgcgg tgagcagatc catgaactaa cgaggaaggg gcgtggctca    5220
gaggcagagc ccctgcctag aatccccaa tgaggggcta ggggtgtggc ccagtggcag     5280
agtccttgcc tagaatctcc ctgtaggggt ctggggttat agctcagcgg tagaaccct     5340
gcctagcatg gcccgtgggt ttcatcctaa gaaccacaaa cagaagcctg ttggtcccaa    5400
cactacagag taagttccag acagccagg actaggcaga aagccctgt ccgtctcccc      5460
ctccccccac ccccaccccc gccaaagaaa tacaaggaga aagccagaag agagggaagg    5520
tgagatggaa gaaccctaga agagatgcag atggaaagac aagtgcagag gctccaccta    5580
gtcacagcct gtgttcgggg ttgggttcca gcatccagtc aggccagacc atgtccctat    5640
gagacccag agtggccaca tccctccccc aggacagctg ttcctaataa tagaccccc      5700
cctcccagca aagggcaga caacagctgg gaggggagg ggtgctccag tgaggccctg      5760
gccagacgaa gccaggttgg gacagagtta gatcaatggc ctggagccat acctgtggtc    5820
tccggaggag aatggctaat ggggactgaa atagaacatc gagttttagg aaggtggcaa    5880
ttggtaggaa agtacagtcc tggctgatag acacgtgaca caggtgacaa aacaggccaa    5940
tggggagagg agaaaggtag tgggaggggt tacagagggc cacagatgag gccgtgggtg    6000
aggggaacgt gagacagctg agctcagtta ccaggctggg gatgtaagcc ggcgaggaat    6060
gcgggccagg tcttctgagc ctcccttgc ctctccctca ggtgtatttt gggcgttggc     6120
tgatcgaggg gggacccta gtggtgctcc tggatgtagg agcctcagct tgggccctgg     6180
agcgctggaa gggtgagctt tggacacct gcaacatcgg ggtaccctgg tacgaccgcg     6240
aggccaatga cgctgtcctg ttcggcttcc tcaccacctg gttcctgggt gaggtaggcg    6300
gtactacaga ccccacctca gccttcctac ccagacttga aaccatcatc atcatcatca    6360
ccgcttgggc cagagagtgg gcttcccctg ggaattctgg gaattgtcca tccactcttt    6420
taatccaagg atcgtctctg aaaagagtct agctgctttt ctcagagacc agaagtgtca    6480
acctcagttt catttcctct atatccaggt gtaaacacac tgcgacattg tttccaggga    6540
gtcctgccag aagagggttg ggtcccagga attctgggga ttgctgtcta ctttaatatc    6600
cattaccgtt aagcactcag ggtaactttt gatacttacc aaccttgagt tggtttcaga    6660
accagaaatc tgggctttcc ccaccccaaa cccattctag aattttttaag agaagttttt   6720
aggagactta attgggatgc cttaggacaa aaaagagcta cacgtgcgtt caaggaaatc    6780
tgggagtttt ggtcctgttt tgtgcccata aaagttctac taccgctgat tgaaatgctg    6840
```

```
agtcttagcc gggtggtggt ggcatgtacc tttaatctcg ggaggtagag acaagcagat    6900
ccctgagttc agggcaagcc tgttctacaa agtgatttcc aggacagcca gtgctattac    6960
acagagaaaa tctgtcttga aaaaccaaaa gaagccgggc agtagtggcc cacgcccttta   7020 atcccagcac tccagaggca gaggcaggca gatttctgag ttcgaggcca gcctggtcta    7080
cagagtgagt tccaggacag ccagggctat acagagaaac cctgtctcaa aaaccaaaa    7140 aaaaaaacaa aaaaaaaac caaacaaaca aacaaaaaaa gaccaagtcc ctgcagtagt    7200
gaccagggct tggggtgttg atccttccag ttccgcgttg ccagaattca taccttgcca    7260
aaaaaaaaaa aaaaaaaaaa aaaatctcat taacctctgg ggacaaggtc agccggttgg    7320
cctaacttgg gttttggccc tttgtgcgac caatgcctgc tctgcataat ggcgggctta    7380
cctctcccct gcttcttcat ccgtgatggg gattgctgct ggttcctttt gggccgtgtg    7440
gaaacacagt gaccctccct gtccctgttg ccccatagtt cctggcccag aacgaagaga    7500
agccgtatgt ggttgcccac ttccacgaat ggttggctgg cgttggtctg tgtctgtgcc    7560
gtgcccggcg cttgccggtg gcaaccatct tcaccactca tgccacgctg ctggggcgct    7620
acctgtgtgc tggcgctgtg gacttctaca caacctgga gaatgtgagc tgcgattgta    7680
ttgtgagaca gcccaaagcc ctggcaggga atcgtgctcc taagagtgca ggctcccagc    7740
ccttccacca tcagacatgc cccccccccc cccatcctg gccatcctcc ctcagacctg    7800
cctctcagag cgcagctgcc aatcccaacc tccctaagac cccagtccag tccctagtct    7860
taccctggtc cttttaacgc tgactttct cccttcctac ccagttcaat gtagacaagg    7920
aagcaggaga gaggcagatc tatcaccggt actgcatgga gcgtgcagca gctcactgtg    7980
cccatgtctt cactaccgta tcccagatca ccgcaatcga ggctcaacac ctccttaaga    8040 gaaaccagg tagggtctga gctgtggtcc ctacatgtgg ctgaggtaag aggctctatg    8100
tcacactcaa caccaatgcc attttactcc agagagtaga acaacttccc taagtcctgg    8160
attgagatgg taactcgtaa atgaagctgg ctgactctgt atcctgaagg ataataggag    8220
ctatagtctc attcatccta attttatgag taactaatat aaatactgat cttctgaaag    8280
aaatgcaaat atggcgggct ttatttttga ataaagtgga actagctagg aacttggttt    8340
actgatcctg cctcacgtgc tcctaagtct tggccctagg tcctgatgag ggttgatttg    8400
ttgtaatcgt gcgtgcgtgt gtgtgtgtgt gtgtgtgtgt gtgtgcgtgt gcgtgtgcgt    8460
gtgtgtgcgc gtgcgtgtgc gtgtgtgtgt gcgcgtgtgt gtgtgcgcgt gcgtgtgtgt    8520
gcgcgtgtgt gtgtgcgtgt gtgtgtgtgt gcgtgtgtgt gtgtgcgtgt gtgtgtgtac    8580
gtgtgcgtgt gtgtgcgcgt gcgtgtgcgt gtgtgcgcgt gtgtgcgtgt gcgtgcgtgt    8640
gtgtgtgtgt gtgtgtgtgt atgtgtgtgt gtgtgtagaa accagaggag aatgtagggg    8700
gtcttctctc tgtgactctc cacctaattt tttaaagagg tgtttgttat ttttatttat    8760
gtatatgtgt gtgtgcgcgc gcgcgcatcc ttgtgtgggg acatgcacac atgcatggtg    8820
tgtatgtgca tgtgtggtgt gtgtgtgttc acaggggggcg gaagagggct tatatcctaa    8880
tcttcagctg cagttacaag tactgttaac caccccgtct gcgtgctgca agagcagcag    8940
taagctcatt tgactgcaga gccggttcat cagacccaac agctcttgta agacagggtg    9000
tctcattgaa cctgaagttc accatttggg tgaggcctcg taagctccca gggcccacct    9060
ctcttccccc acccccacac taggattata ggcgaattta gccatgccca gcttttattg    9120
aatgtggtag gtctgatctt gggtcttttt ttaaataaac tttataaacg cttctatttt    9180
```

```
catatgcatt actctccata cctcagctcc tagagatggg tagtgccatg gatagtgcca    9240
tgggtagtgc catggatagt gccatggata gtgccatggg gcctgatata ctcaggaact    9300
ctgggaggtg cagttttcca tctgtccttc tcccattctg acacagggac tgaaaatacc    9360
actgctctgc ttctccagga tatccactcc cctctctctc tctccctctc cctctccctc    9420
tctccctctc tctccctctc tctccctctc tctctctctc tctctctctc tctctgagcc    9480
agggtctcac tatgtagctc agggtcatct tgattaacac gctctgtcat acttggctca    9540
cagtgcacca tctgtcttta tgtctctttt agggactcaa cccttctcc cctcatatac     9600 ttttaaaaaa tatttgtttt tatgtatgtg tgtgcgtgtg tatggcacgc atgtgtgtgt    9660
gcatgtgtgc gagtctgagt gtataaacac tggttacttt tctgggaaat ccaggtttaa    9720
ttctgagaac acacatggtg cttataacc atctgtgtgt tccaattcct ggagacctga     9780
ccacctcttc ttgcctccac aggcaacagg cacatatatg ttacacagtc atgcatgcag    9840 gcaaaccac catacacata aaatacaaga aaaaatcta aaacagagta tgaagggtca      9900
agtagcggtg ttgaatcagt cccccgtgga gctgagatca ctaaagggcc attataaaac    9960
tgtgacatta tgaaagggaa ttcagccggg cgtggtggtg cacgccttta atcccagcat   10020
tctggaggca ggcggatttc tgagtttgag gccagccagg gctacacaga gaaccctgt    10080 ctcgaaaaac aaacaaacaa acaaaaaaaa aaaaagaaa gaaagggaag tcacctcccc    10140
ttcggttttt gcctgtgaag ttgatcacaa taaagaaatg aagcatgggg ctggtgagat   10200
ggctcagtgg gtaagagcac ccgactgctc ttctgaaggt ccgaagttca aatcccagca   10260
accacatggt ggctcacaac catccgtaat gagatctgac tccctcttct ggtgtgtctg   10320
aagacagcta cagtgtactt acatataata aataaataaa tcttaaaaaa aaaaaaaga    10380 aagaaatgaa gcatgggccc ggcctgtctc tcccaatcct agatattgtg accccaacg    10440 ggctgaatgt gaagaagttc tctgctatgc acgaattcca gaaccttcat gctcagagca   10500
aagcacgaat ccaggaattt gtgcgtggcc atttttatgg gtatgtgagc cagacagtga   10560
agagaggtgg atgggggcgg gggagaggtg agattcctgc gtctgaggag gagggctgtg   10620
gttaggaccc tgagctctgc ggagagaaga ctcccgagtc tcaggaaga gagtgaggat    10680 tccttggtcc tcagtcctgg acagcaatgg tctccattat ttcctgatat ctggagccat   10740
gggatgggta ttagggtaaa tactcatcta aggagaaatt ctgcaattgc atgcatccct   10800
ctgatacctg tgcactataa aaacttcctt tggctctgtg acttctgggg tttgatggct   10860
tcagcacagg gttaggcgct tgggcctcac actcactccc ctgtggcttc tttaggcacc   10920
tggacttcaa cctagacaag actttgtatt tctttatcgc tggccgctat gagttttcca   10980
acaagggagc tgatgtgttc ctggaggcat tggcccggct caactatctg ctcagagtaa   11040
ggcctgctcg gtgggacagt gggtggggag ccggaggggg aagtgtgtgc ctagatgggg   11100
agaacagaga cccgagagat ggctgtggaa acccttggca gagtatagag tcccagaaag   11160
atcagaagtg agatctggtg gcctgtacct gttatcccag cacctgggag gctgaagcag   11220
aaggatcaaa acttcaaggt cagcttttgt ctatagaatg agttcaaggt tgacctgggc   11280
aattttgaga cgctgtatca aaataaaaac cagtctggca gtgtggctca gtggtagatc   11340
ccctgcctag aatcgcccag tgagggggca ggagagtggc tcagtggtaa agcgcctacg   11400
tattctagag atttgatttt aatccccctat attattatga aaagaaaat cggaagtccc    11460 atcattctta gcagcaaagg catgattgag tccacaaccc tgatgtccct ctcatccccg   11520
tccccaggtg aatggcagtg agcaaacagt tgtcgcattc ttcatcatgc cggcccggac   11580
```

```
caataatttc aacgtggaaa ccctgaaggg ccaagccgtg cgcaaacaac tatggtcagc  11640
aatccttgtc caggaccctg tgggcttcgt acctgcagtc gccatatctt atctctctct  11700
ggctatctct gacatgatca ggattcctag tgaactcctc tcttaaagca tgtggcgggg  11760
cagacaagtg tgagcgcgta atcagggcag ccatcacaca gtgaggtgac ctgactcctt  11820
gttatcttgc tgaaccaccg aatcctcacg gagcctgttt cctgctctct gaaacccacc  11880
cgttcactgc ccaccaggct ctgaatatct accacgaggc aggcactgtt ctaagccctg  11940
ggaacagcag atgcatgttt aagaaatgag gaagagctga aaatgtagct catggtaggg  12000
cgttcagcac tcacaagccc cggcacggca taaagtgggt gtgatggtcc atttctctta  12060
attctaatac ttggggagtg gaggctggag ggtcaaaagg tcaaggtcat actgggcagc  12120
atactgagcc aggaggcagt tagagagaga gagaagagac tggtgtggtt gggtcggcat  12180
gtccctggga ggatcgtaag tcatgagaca gtagggtgac agtctttccg aacttgtgtg  12240
ccagggtgtt cctctcagaa tattattcct cctgtttata agacagggcc tagcagtgct  12300
ctgtccaaga ctcattctaa ccctaataat agctgacatt tctggaaggc tctctgtgtg  12360
ctgggctttc cctgacctct cggactcctc tgcaaccacc tgaggttgac tctatttta  12420 cactcatcta caagaggagt cactgacgtt ggagaggaaa ggccaccatt cccagccacc  12480
tcaaggaact caagcagtct ccaggtcccc atcttccagt ttgaggtccc ccggggtgtg  12540
gattctgaac ccagacggaa gtttctctgg tgcccacaat gcctgacaga acatagtggc  12600
tgtgatgtga cattgtttct ctccgttcca gggacacagc caatacagtc aaggagaaat  12660
ttgggaggaa gctctacgaa tccctttag tgtgagtgtc agccctagc tcttctccca  12720 tgattgccct gacccatccc gtcacttcat tctgaaatgc ctccccctcc ccttgcaggg  12780
ggagcctccc ggacatgaac aagatgctgg acaaggagga cttcactatg atgaagagag  12840
ccatctttgc cactcaggta tggtctttac ccctgagcaa agtgctggcc agttctggca  12900
tttgctgagg cctcttgctg caaaggtttc tgggagttct gttctctttg gtggcccttt  12960
acagagggtc cagttctgaa atccagagaa ataccgatag taaaacacac ccaccacatc  13020
acaaagggta agatggttta ttccggaacc aagtataagc atggattggg aacacagatt  13080
ccggttacag tgttccaaca cagtgacgat cgtgtggctt tttatgataa cagaacactg  13140
acagtaatga atgaaggcct tgttaaaata cattgctgga ggggatacca gggggtcccc  13200
ttctcagagg agaaggggtg agggagagat gatgagggga gaatgggagg agaggggct  13260 gatattggga tgtaaagtga acaaataaat taattttaaa gagacactgc tggggctgga  13320
gagatggctc agtggttaag agcgccaact gctcttctga aggtcgtgag ttcaaatccc  13380
agcaaccaca tggtggctca caaccatcca taataagatc tgatgccctc tcctggtgcg  13440
tctgaagaca gctacagtat acttacatat aaataaataa atcttttaaa aaagagaga  13500 gagactgctg gagacatcag gctgagaagg ggcacagaaa ggggaacct cagctctatg  13560 tctgggggca tttccagtct tggtgaaaac tagggtttct tttttttttt tttttttggtt  13620 tttcgagaca gggtttctct gtgtagccct ggctgtcctg gaactcactt tgtagaccag  13680
gctggcctcg aactcagaaa tcagcctgcc tctgcctccc aagtgctggg attaaagaag  13740
cgtgcaccac cactgcccgg cttaaaacta gggtttcttt aagttcctgc accctaaag  13800 gttttaagtc acagccctta ttagagacag gtagcaaaga gtggcgggcg attcaggagc  13860
actgaactag accaagatca attttgttg ttgttgttgt tggtggtgtt tgttgttgt  13920
```

```
tgtttgttgg tttgttttgc ctttgcagac agggtttctc tgtgtagccc tggctgtcct    13980
gaaactgtct ctgtagacca ggttggcttt gaactcagag atccacctgt ttctgccttt    14040
ggagtgctgg tgtgtgtgcc accccacctg cccttatttt tatgagacag agtctaatta    14100
gactctctac ctgccacatt ccagcatctc cacagtcagt cagccttgca gaaggttgtt    14160
ctctgttaag gtacatttct ttttggggac ttcatagttt attgaacgtt cagaagcccc    14220
caggtgacaa cttctgtttc tgctgcccct ggggcgtgtt aagggtagca gtttaagggg    14280
cctttaggag ataggagtca ggcaagtcaa tacacctagt gttttctgga gaacactgaa    14340
tgctcatcag ccactattcg ccgtcctaga actcactctg tagagcaggc tagcctgtaa    14400
ctgagatctg cctacctctg ctttccgagt accaatatta aaggcatgca ctaccaagcc    14460
cagctccgtg gctgtgtctt acctctcaca gaaccctctg attcctgggg ttggagttaa    14520
aaggacagga aacattaggg agatgtggct cacaaaatga aaactacaac tcccatagta    14580
ttttgtatta tattgacctt ggcccctgag gcttttggga gttagagttc ttttttttt    14640 cctgtgggtc aaggggctgg tgcctatgtt tggcattaat gaggctgagt tttgggatct    14700
agacagccag catggattaa tgaggtagaa tgtgttttg ggcaaaatat ttttgaagtt    14760
aagcagccag ctttactcat gaagaagcct tttacatggg gctgctggga gttgtagttt    14820
ttcaccctca taccacccag gagtgggccc attaataaca taatgatgga acagttgtaa    14880
agaacttgtc ataaaagaga gggctggggg gctggagaga tggctcagca gttaagagca    14940
ttgactgctc ttctgaaggt cctgagttca aatcccagca accacatggt ggctcataat    15000
catctgtaat gaaatctgac gccctcttct ggtgcgtctg aagacagcta cagtgtactt    15060
acatataata aaaaattaat taaaaaaaaa agaagaagaa atgtctttta aaaaaaaaa    15120 gagggggctg ggatttcctg tctgtctttg tgttgcagcg gtgacttctg aaattgtgct    15180
taccttccct gaggggtag gcagtgggg ttggaagtga tggtggtgat ggtagggtgt    15240
ggattttcat aagaaaacta caacttgggc ctggagagat ggcgcagtgg ttaagagcac    15300
tggctgcttt ttcagaggtc aagagttcaa ttccagccgg gcagtggtgg ctcacaacca    15360
tctgtaatga gatctgacgc cctcctctgc tgtgtctgaa gacagagagt acttacatat    15420
taaaaaaaaa aaatcttttt taaaaaaaaa aaagaaaact acaactccca gctgtccttg    15480
tggcttgtta tcaaatagac atagctatac acttggctgg ggtaggtaca gttctttaga    15540
gctccccacc cccaactcct ccccacccc ccaccaccgg cagaggggag ggaggagtgg    15600
agtcaacatt ctgatgtcat tttggttcaa gttacgtggt tgcttccatc ttggtaaggt    15660
tctttgagtt tttgttattg acgggcaaga ctatataact aaacacagac atttcctcac    15720
aagatgtgga gtgcctctgt ttagctggga ttttttgtt ggtttggttt agctttgctt    15780
gtgatagtta aaagtcgggc tccagtcagg agtatgctga cctctgctgg tagcttcttc    15840
agagccctgt gaccgccctc cctccctga ccctccctc atgtctcctg tctacagcgg    15900
cagtctttcc caccagtgtg cacccacaac atgctggacg actcctcaga ccccatcttg    15960
accaccatcc gccgaattgg ccttttcaac agcagtgccg accgtgtgaa ggtcagggct    16020
ggcccgaggt tggtggggtg tggctgggga aaggggtctt ggatatcatg cttctcctct    16080
acctagtctg tcaattgtac tgtttagaaa gaaccctggc ttctgaagcc aaatgaattc    16140
agtttaagtc tttagcttgt tgtggacttg ctgtgtgttt ctagagaaat gtaccctctc    16200
tgggctacta taggtggcta gaagtagctc agcccttctc ctctgtcgac aggtgatttt    16260
tcacccagaa ttccttttctt ccacaagccc tctcctcccc gtggattatg aggaatttgt    16320
```

```
ccgcggctgt caccttgggg tcttccoctc ctactatgag ccctggggct acacaccagg   16380
tgagtacagg aggtgagggg tggcggattg ctgggtcctg ttcagttctg gcatgaacct   16440
gcaacacggt tcctctgttt caagatgatg gtagtgaccc atcctgtatc catgtgtcac   16500
atgtttgtct cacagaaggc tacagagctc agactagatg actgatgttc atttccggtc   16560
gtcgacactg ataacctcag ctccaatttg ctgatgttgg agttgcacat gaaccaggcc   16620
ttccccggtg tctctcagac ttgctatgta gcccagactg tcttgaact cctgatcttg    16680
tttccagatt cggagtgcta caccactgtg atctgtttgt gcagtgcggg ctgtagaagc   16740
tggggctctg tgcctgccag gcaagccctc taccctctga gcttctcctc ctggtcccta   16800
gtgctgctca acctcttcct ctcctcacct ctcttcagcc ctgagcttcg agttagaatt   16860
gcttgtgtgt aattctcctt caccgagagg atcctgtggg gcttttcctc cttattttg    16920
ttttttaggc ccgcttgttt tctgataccc aagctggcct ccagctcaca ggtgtctgag   16980
ggtgaccttg aactcttgac ctccctgcct ctacctttcc ttgtattcta gacatattct   17040
tcaattctgc actcccgagc acacactcac acacacagac agacacactg acacacacac   17100
acacacagac acacatacac agacagacac actgacacac acacacatac acacacacac   17160
acactcacac acagacacac acacacacac acacacacac acactcacac acacacacag   17220
taagttaatt aagtttcctt acagagcttg tgtgaggggt gaatgtggga aggagatgtt   17280
gggaggagtg gctagaacct ccagagaagg tctaacgtcc ccaccccac ttctttttta    17340
gttcattatt atgtttattc attcattttc taaatctta ttaattatt tattgacttt     17400
acatcccaat tgctgctccc cgccccgccc ccactcctat gagggggaca ttaacaagca   17460
ggtcttggtt ttgagagtca cttgcaaatc attttgctct ggttaaaatg ataatagagc   17520
caggtggtgg tggtgcacgc ctttaattcc agcacttggg aggaagaggc aggcaggtcc   17580
atgagttcga ggtcagcctg gtctacagag tgagttccag gacagccagg ggtacataga   17640
gaaaccatgt ctcagaaaaa aaaaaaaaa aagttgataa tgtttgggaa actaccatgg    17700
ggtctctgtc tgccaagctg agcacctggc agtccttacc ttagctccct gaaccttgga   17760
atcacacgct gctgccattg tatctcactc agatctttcc ttaccaccag tggacacggg   17820
ctgtgagctg ggtgtggagg catactgggg aagccgaggc aggagagtta tctatcattc   17880
cacaggctga ctgagctaca cagtaagacc ctgtctcaaa agcaaaccaa ccaaagagca   17940
tgtgcacctc taatgataac tgatgggatg cagaggagga agattaggag ttcaaggtca   18000
tctttggcta catagtgggc tcagggccat cctgagctac ataagattct gtctttaaaa   18060
aggggtggg gctggagaga tggcttagca actaagaata ctgtgttcta gaggacctag    18120
atttgctggg tatagttgca catgcctttg atccctgtac ccaggaggca gaggcaggtg   18180
ggcctctgtg agttcaaggc caagcctggt ctacacagtg ggctccagga cagccagagc   18240
tatatagtaa gaccttgtct caagaaagac aaaaataagg gctggtgagg tggctcagcc   18300
gttaagagaa ttgactgttc ttccagaggt cctgagttca attcccagca accccatggt   18360
ggggttgtaa tgggagctga taccctcttc tggtgtgtga agacagtgac agtgtgctca   18420
catacataaa ataaataaat cttttaaaac aaacaagccg gcatggtgg tgcatgcctt    18480
taatcccagc actcgggagg cagaggcagg cggatttctg agttcgaggc cagcctggtc   18540
tacagagtga gttccaggac agccccaggg ctatacagag aaaccctgtc tcaactcccc   18600
ccaaaacaaa caaacaaaaa aacaaagcca aaaataaaat aaaacagcca taaaaaaccc   18660
```

-continued

| | |
|---|---|
| agattcaatt cctagcaccc atatggctgc taacagtcta actgtacttc caggggatcc | 18720 |
| aacactcttc tggcctccac aggtgcttca tacacatggc gcatgtatgt aggcaaatca | 18780 |
| cccatacccca taaaaattaa aaattaataa atctttgttt gtttgtttgt tttgttttg | 18840 |
| tttttgtttt tggttttggt ttatcaagac agggttctc tgtatagccc tggctatcct | 18900 |
| ggaactcact ttgtagacca ggctggcctc gaactcagaa atctgcctgc ctctgcctcc | 18960 |
| cgagtgctgg gattaaaggc atgcgccacc acgcccggct tcaaaattaa taaatctttt | 19020 |
| tttaaaagat ttatttattt attatatgta agtatactct agctgtcttc agacactcca | 19080 |
| gaagacagcg ccagatctca ttacaggtgg ttgtgagcca ccatatggtt gctgggattt | 19140 |
| gaactcagga ccttcggaag agcagtcagt gctcttaacc gctgagccat ctctccagcc | 19200 |
| ccaaaattaa taaatcttaa aacaataact acaaccaacc tcatgatcat gtcataatct | 19260 |
| aaagccgtgt catgcacaca cgagcacaca cacagatacg aatcttaacg ccgtgatggt | 19320 |
| taagtaaagt tatttctgtg agccagcatt ggttagcgtt ccataaataa gtatcctctt | 19380 |
| tatcacaggt ttccgcagat tcactttct aaggctcttt ggttcctaga aatgggggag | 19440 |
| gccccttgcg ggtgtagcca ggcgcggttg gtttagttgc cagcaggtgg cgatgtagag | 19500 |
| ccatctctaa cagggcaggc tactgagtag ccttttttcc cctcccacct ttggttcctc | 19560 |
| agcggagtgc actgtcatgg gcatccccag catctccacc aacctctccg gctttggctg | 19620 |
| ctttatggag gaacacatcg cagatccctc agcttacggt cagtgcagag ggaggacaga | 19680 |
| acatggcggg cgctggtccc catttcagac tcttgttatc gttaacaaat cctgattcct | 19740 |
| gcctctgtag gcatttacat tctggatcgg aggttccgca gcctggatga ttcatgctca | 19800 |
| cagctcacct ccttcctgta cagcttctgc cagcagagcc ggcgacagcg catcatccag | 19860 |
| cggaaccgca cagaacggtt gtcggacttg ctagattgga agtacctggg ccgggtatga | 19920 |
| ctgatttcct ttcctaggcc tcctctggtt ctgtagcctt aaagaattga gataggggctg | 19980 |
| ggcgtggtgc tgcatgcttt aatctcagcc ctcagaaggc agaggcagat ggatttctgt | 20040 |
| gagttcctgg gcagcctgat ctacagaggg aatccaggac agctaggact ctgttacaca | 20100 |
| aagaaaccct atcttgaaaa atcaaaaaag agagagaaga tggagatagc ctgatgtggt | 20160 |
| ggtacagagc tcaggagaca gaggcaacct ggatacaaag taagttccag dacagccaga | 20220 |
| gctacataga gaaacaaaga ggctggaaat agatcaaagt ttcctgctta ttgtagttgt | 20280 |
| tgtctcttta agcaagtgat gtgaggctga agaagacagc tcaatggttc aaatcccagc | 20340 |
| acccacatgg cagctcataa ctatgtgtaa ctccaagatc tgacactctc acacagacac | 20400 |
| acacactgtc aaaacaccaa tgcacaaaac aaacaaacaa acaaacaaac aagcaaaaaa | 20460 |
| gaaactgttg tcagagctag agacacagca ttggctgctc ttccagaaga ctagggttca | 20520 |
| gttccagcac ccacatggtg gctcacaaac atctgtaatt ccacttccag cagatttgat | 20580 |
| atcctcttgg cttctgtggg taccagacat acttctgata cctagaacac atgcagataa | 20640 |
| aacactcata cacacatatt ttttttaaa tcccaatatg atgatccctg tgattttagc | 20700 |
| actggaaggt aaagataaga gaatacctgg aggagctgtc gagatggccc agaggttaag | 20760 |
| agcactgact gttcttccag aggtcctgag ttcaaatccc agcaaccaca tggtggctca | 20820 |
| caaccatctg taatgagatc tgatgccctc ttatagtgta ctcatacata ataaataaat | 20880 |
| aagtctttta aaagaagaaa aagaggatac ttggggccag gcagtggtgg tacctagcac | 20940 |
| tctgaagca aatctctgag ttcaaggcca gcctgatcta catagtgagt tcagtgacag | 21000 |
| gcaaggctag aaggcaagaa gctctgtctc agcaaacaaa taaataaaaa agaaagaaag | 21060 |

```
agctaggcgt gttggcgcac gcctttaatc gcagcacttg agaggcagag gcaggtggat  21120
ttctgagttc aaggccagcc tggtctataa agtgagttcc aggacagcta agactacaca  21180
gagaaaccct gtctcgaaaa actgaagaa  agaaggaag  gaaggaagga agaaagaaag  21240
aaagaaagaa agaaagaaag aaagaaagaa agaaagaaaa aaggggtacc tgggattcac  21300
tggacagcca gcatcctatt tatggcaagt ccccgcctca agaaacaagg tgaaagccag  21360
gtgtggggtt gtctgccttt aatcccagca ctttacaggc atagactgtg agtgcaaagc  21420
catcctagtc tacatagcaa gaccttgcct caaggaaaaa aggaaacaga gagagagaca  21480
gacagacaga cagagagaca gagaagctgg agagatggct cagtgtgttt aggaagagat  21540
caggcagcac tcacataacc tggcatctca gaaacacttg gaattccagc tgcaaaagac  21600
tgaatgtcat cttctagtcc ccacacacag gcacatgaca gcacacatca tatgttcata  21660
tacataaata aatcttacaa aacaaaattc aggatgaatt ttgcctgaga aatgacatct  21720
gaagttgttc tctggcctct gtatatagac acatatacac acacatac  atgcacatac  21780 atacacacat acatgcacat acatacgcac atacatacat caaaaatgaa aagagagcaa  21840
ggtgttagag tgcccacctt cagtctaagc acttggagac agagacagga gacaggtggg  21900
tctctgtgag tttgaggcca gcttctttta cattgccagg tctgtaacag ccaagagtac  21960
atagatccga tctcaaaaac aaaaaataaa tacataaatg aataaataaa taaagataa   22020 aaaaatctag aaatagcatc tggatagagt tctcatttgt gtgaccaaaa gagtatttga  22080
gaattcacct gccctgtagg aaggtatgac tagagcatgg tccatgccta gttcacttgg  22140
aacattcaca tttgcacagg aacatttgca taggagagat gagataactt tgcccagtgt  22200
gctcatctgt ataaaggtat agcaattgga gcctggctca agttcaaag  ccagctaggg  22260 gacacgtagt aacattccca acgcaaaaca gaaaatacaa gaaggtgtgg ccatcggtac  22320
ccaccagccc aggtttgtca tccagctact tggaaggatg aggcaggaaa gtcaccagtg  22380
ttaccaagtg aagattgctg gggactccag cagtgacggg tggagagcat ggctcagtgg  22440
tggagcaggg gagctgggcg tgcctttagg ttttagaccc ttaactataa tccaccagag  22500
aagtggttca gtggtagaga ccctgcctcg tgtccaccag taatgagggg tgtgtggctg  22560
ggcttgtgta gaaaaaatgt ggctggacat tgatggcctt gaataaatcc caagcactgg  22620
ggaggcagag gcaggcagat ctctgtgatt ttgaggtcag cctgatctac agagttctat  22680
gacagccagg acttacacaa agaaactctc aaaaagcaaa ccagacaaac aaacaaacaa  22740
acaaaaaagt gctgggggtt tatctgcctg aagccaggtg tgtagcctct gtccttgacg  22800
ctgtctgccc tcctgtctca gtactacatg tctgcgcgcc acatggctct ggccaaggcc  22860
tttccagacc acttcaccta tgaacccat  gaggtagatg cggtaagtgg agccgggatc  22920
gacgctgggc caggagtgaa gggctggggc aggctggttt ggggttgaca gttagtggac  22980
acctctaggg acttaaatgg cacccattca ttttggtttg tgcctgctct gggtatgcag  23040 acccagggt  accggtaccc acgaccagcc tccgtcccgc cgtcgccctc actgtctcga  23100
cactccagcc cacaccagag tgaggatgag gaagagccac gggatggacc cctgggggaa  23160
gacagtgagc gttatgatga ggaagaggag gctgccaagg accgccgcaa catccgggca  23220
cctgagtggc cacgcagggc ctcctgttcc tcctcacag  gtggcagcaa gagaagcaac  23280
tcggtggaca ctgggccctc cagctcactc agcacaccca ctgagcccct gagtcctacc  23340
agttccctgg gtgaggagcg caactaagct cccacccca  tcccattccc tgcctgtcca  23400
```

```
gtgctcctct cgcagagggc ctatgcagat gggagggtgc ctgaaccccca ctccagactc   23460 ttgagtggga cccctaccca gtgtggtcca tagcctaacc tctgtttcag acactccagc   23520
ccttgagctc caatcttgga gttcccgcac tccacgccgc cgtgcctttc ttggattgca   23580
ggatgcattc tttgtgcact gatctggagt ctccaggctt agactgggtc ccagaggcca   23640
ggcatctgcc attgtttttc aatgccagag gttttaggac acctggttta ttggcttcca   23700
ggctgtggct cttcgtttg atcctataat catacagagt atgctttgct caggcctgcc   23760
tctgggacca cctcatgttg gattctgtgt ggcttcccga atcagccaag ttcagagtta   23820
ggacatttca gggattaaca taattgaaaa tcagcctgca aggtagctca gtagctctgt   23880
cgacagattg cttgtctagc atgcccgaag ccctgggatc taactctaga acctcataaa   23940
cctggtgcgg tgatacacat ctgtaatccc agcactcggt aggtagaggt agacggatca   24000
agagttaaag gccatcatcc tctgctacat agggagttca aggccaaact gggcaacatg   24060
agacactgtc tcaaaagcaa agtaaaggtg gtggaatgct cacggtcctc catttcaacc   24120
cacgactgcg atgctgggac atgctgcaag gttggcctcc ctgggtgtgt tcttcaaagg   24180
agcatgcgga gttggaccag acacctttct gccttttttc tggaccagac cttcttttcc   24240
ttggtccagt gtcccctcta gggaatgcct ccattgaggg cagaatgtct gtcaaccca    24300 caagtgctca gcccactgtg aaaccactgg gttctgggtc ccagtggctg aatcaggagt   24360
cttttgtcac tgtgctgcac cccggtcccc tttcctgata caaaccgag cccaccggct    24420 tcttgaagcc ccacatgtac ctcgaggcct ttctgcctgc aagcttcagt gaatgggcgg   24480 gccctcctc acgtgtgctg tgtctggccc agtgcctttg gtttgcattt gggaggggga   24540
gggcagaagg tgtgtgattg gagtgtgtct agagatgaaa aaaaaaaaa gaaaatacac    24600 ctgtatttaa gaatgccaac tgtggctgga cataagctct tgtggtgtgg tgggtctctc   24660
ttgcttcccc agtcctgtat tttagttttt acagatagga tcttgccttg ccccccccc    24720 cccagatggt tcaaattcac agcagtccta tctcagcctc tcaagagctg gcattaccag   24780
gagtgccagc ttcccccaga ttttggttct gctcttacga gctccataga cttctactct   24840
gtgcagatct gggttactgt tctgaggtcc ccgtgctgtt gttaggaaag gtacatctga   24900
ctgcttagat ttgagatcca agtggcaaac actggcccca gtgaccttgg gtagacggtg   24960
gccgacatgg gggacccttg gggaaatcac aaatgcacag gtcaaaggac ccaaagctca   25020
aagcttacat ggactagagc ttctggggcc agcttgagca attggtgaga tctagcctga   25080
aaaagtgaaa agcccgggac agatgtccct aagcagaatg tccccgcaac acagtgagaa   25140
actggattcc agccgcagga ctttgttcct gcttctcaat gctgtttccc acgtggacat   25200
cgctgccaga atccctttag caggttctcc ctgcttagcc tcagtgacct gtgcatgact   25260
ggagttactg ctctaacccc caaccctccc gttatcaatc tcatgctttt aggggtggag   25320
tggcctgact agaagaaacc tgtagtgctg ggtcatcttc ctgtccacat gactgcttcc   25380
ccagagccat ggcataatac tgagccaagg gcctatcatg tggcttcata cgacccttgg   25440
acttgtttta accagtgtga gctgacacag cagtattgtc cggtgttcca cccccaccc    25500 caccaacttc ccatgtttct aaccccttg caatggttta gttcccattt gggcaatggt    25560
cccaagtttc acatcctctt tttgatgggc ccagcatcta gttcggaatc cagcaagaca   25620
ccctggctcc ccaccctcgc tcagccagca cccagggctc agcttgctca cctcctggcc   25680
ttctacttgt atgtttaact catttctgaa cttggatgtt taagcctttt cacttccctg   25740
cacagtaaca taaaccaagg actggcaaac tgctacaggc tacagactcc tacgacctgg   25800
```

```
atttgccaca tgaaaaggca gatactacca cacagagatc gctgtaagtt atcacatgtg   25860
ggttcccaca aaaaacagga gtacatacag ccaacctctt ctttctcgtg cacccctccc   25920
acatatatag aaaaaacacc agctgctgtc tcaaaaagct ttattttac ttggtccaag    25980
acttgacaga ggctccaggg cggttacaaa gctgcctagt ggcttgagag gttcattcag   26040
gtggaggtcc cagggcgggc tggtgcagag cagagggggg agccccttgg aaggtacaga   26100
ggcctcctag tcgtgcttga gagtgaggcg ctcaaagaga tactcgccca gagaccctg    26160
gggcgcgcca gtctgcgctg gttgtggccc cgccaccctg cggaggttgg tcagatggtt   26220
gcccatcttc ttgatgagtt tcacctcctt atccagatag tggctttcca ggaagtcaca   26280
gagctgtaaa ggaaggaaga gacatcagac accgagttct aagagacagg tgtgagcagg   26340
aagctttaaa aaaaaaaaat cctgccctca agggcaggta ggtaggtagg taggtgtgtc   26400
ctcagtactg tgtgtggtgc ttctgcaatc tgcactcggg aggcaggagg attaaattat   26460
tgggagctga aagccaacac acaacagtct aggttttgtc agagaaggga agaaatgatt   26520
agcaaggtac ttacatgagg gtccgcgcgg gcagaaccca gggcatgcag atccaagagg   26580
gcctgattca ggttcttctc catggccaag gcagcttcca tggcctcctg ggttttaccc   26640
cattcatctt gagatggctt ctgcacacaa gaatatcaag cctagattac atccttcacc   26700
cagccaatat aaaactgact gcacaggaaa agtgggcaca gtggggaaaa ataatgggat   26760
actgtcttta atcccaccac tgagagactg ggcgagaaga caggaggatc tcttgatagg   26820
aggcaacctg gtctacattg tgatttccat gctagctaga gagacaccgc ctctccccag   26880
cccagcagtc ctcatctgta ttctgtaatt accccatttt tccagtttct gacatcctgg   26940
tgggtttagt tgctctacat actcctattg tctacactag tcctgccacc actcccttcc   27000
aagacgtcta tccggatgcc caaactatgg ggatggcaag taaacgcaca tgctcggtag   27060
tgcccaatac ccccgcttct tacctgcaca tcctggaaga gtgcacggcc cccgcgatcg   27120
ttctgaaact cgaggagacg ctccgcgccc tcgcgcttct cctcggccaa ttcgcggaag   27180
aagtggccta cgccctccag agccacgtca tcccgatcaa aaagaagcc ctgcgggagg    27240
ttacaaatac gagttaacgg aacgcggtgg ctcggctcac actgtaaact tcaatcgcaa   27300
cactcaagag gtagaggcag tacgtgtgag atttcgaggg cagcccggtc tgcccagcga   27360
gttccagtca gacaaaacta ctatgtacac agcgcgcagg gagagggaga ggtcggagca   27420
cagtctctgc cctgcatgga acaaagaagg cccgcgcatg cgcaggaggg tgggtgtgat   27480
ggacccccc ccccccccc cgttcagaag gcaaccccga gctgctcacc agagagaggt     27540
aggtgtagga ggcccgcagg tgcaagttga ccaggcggtt cacggcagct tccacctcgg   27600
tggaataatt ctgacgaatc tgagaggtca tggctgatcc ggagtaggag ctaaccgcga   27660
agagacggtg cagactggtc ctaggagctg aaggcagcga ggagatggtc ccggaggctg   27720
cgactggaga gacttgtaaa ggcggctgga agcgagtaca gtgggaatcc ccgggtctgt   27780
tccgttcaaa cactgttgaa gcaagacaca gatccacggg acctccaagg cgctgctcta   27840
agtcccgggc aaggagcgct cctttatag catgttgacc ctccggaggg aggggtgccc    27900
caggcccgag actaaccaat cggcggtggc gtgaggcgga gacggaaaag tatacttgac   27960
caatccggag ctgagggaa cctcgctccc cacccaccca                          28000
```

<210> SEQ ID NO 2
<211> LENGTH: 3635
<212> TYPE: DNA

<213> ORGANISM: Homo sapiens

<400> SEQUENCE: 2

| | | | | |
|---|---|---|---|---|
| tcctggcggc | tgcgaggttt | cactgcaggg | gcgccagtgg | gctcagtgac | gctgcggcct | 60 |
| ccttctgcct | aggtcccaac | gcttcggggc | aggggtgcgg | tcttgcaata | ggaagccgag | 120 |
| cgtcttgcaa | gcttcccgtc | gggcaccagc | tactcggccc | cgcaccctac | ctggtgcatt | 180 |
| ccctagacac | ctccggggtc | cctacctgga | gatccccgga | gccccccttc | ctgcgccagc | 240 |
| catgccttta | aaccgcactt | tgtccatgtc | ctcactgcca | ggactggagg | actgggagga | 300 |
| tgaattcgac | ctggagaacg | cagtgctctt | cgaagtggcc | tgggaggtgg | ctaacaaggt | 360 |
| gggtggcatc | tacacggtgc | tgcagacgaa | ggcgaaggtg | acaggggacg | aatggggcga | 420 |
| caactacttc | ctggtggggc | cgtacacgga | gcagggcgtg | aggacccagg | tggaactgct | 480 |
| ggaggccccc | accccggccc | tgaagaggac | actggattcc | atgaacagca | agggctgcaa | 540 |
| ggtgtatttc | gggcgctggc | tgatcgaggg | aggccctctg | gtggtgctcc | tggacgtggg | 600 |
| tgcctcagct | tgggccctgg | agcgctgaaa | gggagagctc | tgggatacct | gcaacatcgg | 660 |
| agtgccgtgg | tacgaccgcg | aggccaacga | cgctgtcctc | tttggctttc | tgaccacctg | 720 |
| gttcctgggt | gagttcctgg | cacagagtga | ggagaagcca | catgtggttg | ctcacttcca | 780 |
| tgagtggttg | gcaggcgttg | gactctgcct | gtgtcgtgcc | cggcgactgc | ctgtagcaac | 840 |
| catcttcacc | acccatgcca | cgctgctggg | gcgctacctg | tgtgccggtg | ccgtggactt | 900 |
| ctacaacaac | ctggagaact | tcaacgtgga | caaggaagca | ggggagaggc | agatctacca | 960 |
| ccgatactgc | atggaaaggg | cggcagccca | ctgcgctcac | gtcttcacta | ctgtgtccca | 1020 |
| gatcaccgcc | atcgaggcac | agcacttgct | caagaggaaa | ccagatattg | tgaccccccaa | 1080 |
| tgggctgaat | gtgaagaagt | tttctgccat | gcatgagttc | cagaacctcc | atgctcagag | 1140 |
| caaggctcga | atccaggagt | ttgtgcgggg | ccatttttat | gggcatctgg | acttcaactt | 1200 |
| ggacaagacc | ttatacttct | ttatcgccgg | ccgctatgag | ttctccaaca | agggtgctga | 1260 |
| cgtcttcctg | gaggcattgg | ctcggctcaa | ctatctgctc | agagtgaacg | gcagcgagca | 1320 |
| gacagtggtt | gccttcttca | tcatgccagc | gcggaccaac | aatttcaacg | tggaaacccct | 1380 |
| caaaggccaa | gctgtgcgca | aacagctttg | gacacggcc | aacacggtga | aggaaaagtt | 1440 |
| cgggaggaag | ctttatgaat | ccttactggt | tgggagcctt | cccgacatga | acaagatgct | 1500 |
| ggataaggaa | gacttcacta | tgatgaagag | agccatcttt | gcaacgcagc | ggcagtcttt | 1560 |
| cccccctgtg | tgcacccaca | atatgctgga | tgactcctca | gacccatcc | tgaccaccat | 1620 |
| ccgccgaatc | ggcctcttca | atagcagtgc | cgacagggtg | aaggtgatt | tccacccgga | 1680 |
| gttcctctcc | tccacaagcc | ccctgctccc | tgtggactat | gaggagtttg | tccgtggctg | 1740 |
| tcaccttgga | gtcttcccct | cctactatga | gccttggggc | tacacaccgg | ctgagtgcac | 1800 |
| ggttatggga | atccccagta | tctccaccaa | tctctccggc | ttcggctgct | tcatggagga | 1860 |
| acacatcgca | gacccctcag | cttacggtat | ctacattctt | gaccggcggt | tccgcagcct | 1920 |
| ggatgattcc | tgctcgcagc | tcacctcctt | cctctacagt | ttctgtcagc | agagccggcg | 1980 |
| gcagcgtatc | atccagcgga | accgcacgga | gcgcctctcc | gaccttctgg | actggaaata | 2040 |
| cctaggccgg | tactatatgt | ctgcgcgcca | catggcgctg | tccaaggcct | tccagagca | 2100 |
| cttcacctac | gagcccaacg | aggcggatgc | ggcccagggg | taccgctacc | cacggccagc | 2160 |
| ctcggtgcca | ccgtcgccct | cgctgtcacg | acactccagc | ccgcaccaga | gtgaggacga | 2220 |
| ggaggatccc | cggaacgggc | cgctggagga | agacggcgag | cgctacgatg | aggacgagga | 2280 |

```
ggccgccaag gaccggcgca acatccgtgc accagagtgg ccgcgccgag cgtcctgcac    2340
ctcctccacc agcggcagca agcgcaactc tgtggacacg gccacctcca gctcactcag    2400
caccccgagc gagcccctca gcccaccag ctccctgggc gaggagcgta actaagtccg     2460
ccccaccaca ctccccgcct gtcctgcctc tctgctccag agagaggatg cagaggggtg    2520
ctgctcctaa accccgctc cagatctgca ctgggtgtgg cccgcagtg ccccacccca      2580 gtccgccaaa cactccaccc cctccagctc cagtttccaa gttcctgcac tccagaatcc    2640
acaaagccgt gcctttctct ggctccagaa tatgcataat cagcgccctg gagtcccctg    2700
ggcctggacc gcttcccaga ggccaggaat ctgccattac tctgcggtgg tgccagaggt    2760
tttaggaaac ctggcatggt gctttcaggt ctggggcttt tagagccccc cgtgtggctt    2820
acaaattcta cagcatacag agcaggccac gctcaggccc ggcatgcggg ccaccaagtt    2880
ctggaaacca cgtggtgtcc ctgcgaatgg ggcgatcaag tccagagccg ggcactttc     2940 agagtttgaa ggtaactgag agcagatggt cctccatttc aactccagaa gtggggctct    3000
gggagggatg ttctagccct ccctggcatg tcagagccag gctctgcctg gaggatccct    3060
ccatccggct cctgtcatcc cctacacttt ggccaagcaa gaggtggtag aaccacttgg    3120
ctgctcattc cttctggagg acacacagtc tcagtccaga tgccttcctg tctttctggc    3180
cctttctgga ccagatccta ctcttccttt ctaaatctga gatctccctc cagggaatcc    3240
gcctgcagag gacagagctg gctgtcttcc cccacccta acctggctta ttcccaactg     3300
ctctgcccac tgtgaaacca ctaggttcta ggtcctggct tctagatctg gaaccttacc    3360
acgttactgc atactgatcc ctttcccatg atccagaact gaggtcactg ggttctagaa    3420
cccccacatt tacctcgagg ctcttccatc cccaaactgt gccctgcctt cagctttggt    3480
gaaagggagg gcccctcatg tgtgctgtgc tgtgtctgca ccgcttggtt tgcagttgag    3540
aggggagggc aggaggggtg tgattggagt gtgtccggag atgagatgaa aaaaatacat    3600
ctatatttaa gaatcccaaa aaaaaaaaaa aaaaa                               3635

<210> SEQ ID NO 3
<211> LENGTH: 3443
<212> TYPE: DNA
<213> ORGANISM: Homo sapiens

<400> SEQUENCE: 3
tcctggcggc tgcgaggttt cactgcaggg gcgccagtgg gctcagtgac gctgcggcct     60
ccttctgcct aggtcccaac gcttcggggc aggggtgcgg tcttgcaata ggaagccgag    120
cgtcttgcaa gcttcccgtc gggcaccagc tactcggccc cgcaccctac ctggtgcatt    180
ccctagacac ctccggggtc cctacctgga gatccccgga gccccccttc ctgcgccagc    240
catgccttta aaccgcactt tgtccatgtc ctcactgcca ggactggagg actgggagga    300
tgaattcgac ctggagaacg cagtgctctt cgaagtggcc tggaggtgg ctaacaaggt     360 gggtggcatc tacacggtgc tgcagacgaa ggcgaaggtg acagggacg aatggggcga    420 caactacttc ctggtggggc cgtacacgga gcagggcgtg aggacccagg tggaactgct    480
ggaggccccc accccggccc tgaagaggac actggattcc atgaacagca agggctgcaa    540
gttcctggca cagagtgagg agaagccaca tgtggttgct cacttccatg agtggttggc    600
aggcgttgga ctctgcctgt gtcgtgcccg gcgactgcct gtagcaacca tcttcaccac    660
ccatgccacg ctgctggggc gctacctgtg tgccggtgcc gtggacttct acaacaacct    720
```

| | |
|---|---|
| ggagaacttc aacgtggaca aggaagcagg ggagaggcag atctaccacc gatactgcat | 780 |
| ggaaagggcg gcagcccact gcgctcacgt cttcactact gtgtcccaga tcaccgccat | 840 |
| cgaggcacag cacttgctca agaggaaacc agatattgtg accccaatg ggctgaatgt | 900 |
| gaagaagttt tctgccatgc atgagttcca gaacctccat gctcagagca aggctcgaat | 960 |
| ccaggagttt gtgcggggcc attttatgg gcatctggac ttcaacttgg acaagacctt | 1020 |
| atacttcttt atcgccggcc gctatgagtt ctccaacaag ggtgctgacg tcttcctgga | 1080 |
| ggcattggct cggctcaact atctgctcag agtgaacggc agcgagcaga cagtggttgc | 1140 |
| cttcttcatc atgccagcgc ggaccaacaa tttcaacgtg gaaaccctca aaggccaagc | 1200 |
| tgtgcgcaaa cagctttggg acacggccaa cacggtgaag gaaaagttcg ggaggaagct | 1260 |
| ttatgaatcc ttactggttg ggagccttcc cgacatgaac aagatgctgg ataaggaaga | 1320 |
| cttcactatg atgaagagag ccatcttgc aacgcagcgg cagtcttcc ccctgtgtg | 1380 |
| cacccacaat atgctggatg actcctcaga ccccatcctg accaccatcc gccgaatcgg | 1440 |
| cctcttcaat agcagtgccg acagggtgaa ggtgattttc cacccggagt tcctctcctc | 1500 |
| cacaagcccc ctgctccctg tggactatga ggagtttgtc cgtggctgtc accttggagt | 1560 |
| cttcccctcc tactatgagc cttggggcta cacaccggct gagtgcacgg ttatgggaat | 1620 |
| ccccagtatc tccaccaatc tctccggctt cggctgcttc atggaggaac acatcgcaga | 1680 |
| cccctcagct tacggtatct acattcttga ccggcggttc cgcagcctgg atgattcctg | 1740 |
| ctcgcagctc acctccttcc tctacagttt ctgtcagcag agccggcggc agcgtatcat | 1800 |
| ccagcggaac cgcacggagc gcctctccga ccttctggac tggaaatacc taggccggta | 1860 |
| ctatatgtct gcgcgccaca tggcgctgtc caaggccttt ccagagcact tcacctacga | 1920 |
| gcccaacgag gcggatgcgg cccaggggta ccgctaccca cggccagcct cggtgccacc | 1980 |
| gtcgccctcg ctgtcacgac actccagccc gcaccagagt gaggacgagg aggatccccg | 2040 |
| gaacgggccg ctggaggaag acggcgagcg ctacgatgag gacgaggagg ccgccaagga | 2100 |
| ccggcgcaac atccgtgcac cagagtggcc gcgccgagcg tcctgcacct cctccaccag | 2160 |
| cggcagcaag cgcaactctg tggacacggc cacctccagc tcactcagca ccccgagcga | 2220 |
| gccctcagc cccaccagct ccctgggcga ggagcgtaac taagtccgcc ccaccacact | 2280 |
| ccccgcctgt cctgcctctc tgctccagag agaggatgca gaggggtgct gctcctaaac | 2340 |
| ccccgctcca gatctgcact gggtgtggcc ccgcagtgcc cccacccagt ccgccaaaca | 2400 |
| ctccaccccc tccagctcca gtttccaagt tcctgcactc cagaatccac aaagccgtgc | 2460 |
| cttttctctgg ctccagaata tgcataatca gcgccctgga gtccctggg cctggaccgc | 2520 |
| ttcccagagg ccaggaatct gccattactc tgcggtggtg ccagaggttt taggaaacct | 2580 |
| ggcatggtgc tttcaggtct ggggcttta gagcccccg tgtggcttac aaattctaca | 2640 |
| gcatacagag caggccacgc tcaggcccgg catgcgggcc accaagttct ggaaaccacg | 2700 |
| tggtgtccct gcgaatgggg cgatcaagtc cagagccggg gcactttcag agtttgaagg | 2760 |
| taactgagag cagatggtcc tccatttcaa ctccagaagt ggggctctgg gagggatgtt | 2820 |
| ctagccctcc ctggcatgtc agagccaggc tctgcctgga ggatccctcc atccggctcc | 2880 |
| tgtcatcccc tacactttgg ccaagcaaga ggtggtagaa ccacttggct gctcattcct | 2940 |
| tctggaggac acacagtctc agtccagatg ccttcctgtc tttctggccc tttctggacc | 3000 |
| agatcctact cttcctttct aaatctgaga tctccctcca gggaatccgc tgcagagga | 3060 |
| cagagctggc tgtcttcccc caccccctaac ctggcttatt cccaactgct ctgcccactg | 3120 |

```
tgaaaccact aggttctagg tcctggcttc tagatctgga acctaccac gttactgcat    3180 actgatccct ttcccatgat ccagaactga ggtcactggg ttctagaacc cccacattta    3240
cctcgaggct cttccatccc caaactgtgc cctgccttca gctttggtga agggagggc     3300 ccctcatgtg tgctgtgctg tgtctgcacc gcttggtttg cagttgagag gggagggcag    3360
gaggggtgtg attggagtgt gtccggagat gagatgaaaa aaatacatct atatttaaga    3420
atcccaaaaa aaaaaaaaaa aaa                                            3443

<210> SEQ ID NO 4
<211> LENGTH: 3453
<212> TYPE: DNA
<213> ORGANISM: Homo sapiens

<400> SEQUENCE: 4
tcctggcggc tgcgaggttt cactgcaggg gcgccagtgg gctcagtgac gctgcggcct     60
ccttctgcct aggtcccaac gcttcggggc aggggtgcgg tcttgcaata ggaagccgag    120
cgtcttgcaa gcttcccgtc gggcaccagc tactcggccc cgcaccctac ctggtgcatt    180
ccctagacac ctccggggtc cctacctgga gatccccgga gccccccttc ctgcgccagc    240
catgccttta aaccgcactt tgtccatgtc ctcactgcca ggactggagg actgggagga    300
tgaattcgac ctggagaacg cagtgctctt cgaagtggcc tgggaggtgg ctaacaaggg    360
tgtatttcgg gcgctggctg atcgagggag gccctctggt ggtgctcctg gacgtgggtg    420
cctcagcttg ggcccggag cgctggaagg gagagctctg gatacctgc aacatcggag     480 tgccgtggta cgaccgcgag gccaacgacg ctgtcctctt tggctttctg accacctggt    540
tcctgggtga gttcctggca cagagtgagg agaagccaca tgtggttgct cacttccatg    600
agtggttggc aggcgttgga ctctgcctgt gtcgtgcccg gcgactgcct gtagcaacca    660
tcttcaccac ccatgccacg ctgctggggc gctacctgtg tgccggtgcc gtggacttct    720
acaacaacct ggagaacttc aacgtggaca aggaagcagg ggagaggcag atctaccacc    780
gatactgcat ggaaagggcg gcagcccact gcgctcacgt cttcactact gtgtcccaga    840
tcaccgccat cgaggcacag cacttgctca agaggaaacc agatattgtg accccccaatg    900 ggctgaatgt gaagaagttt ctgccatgc atgagttcca gaacctccat gctcagagca    960
aggctcgaat ccaggagttt gtgcggggcc atttttatgg gcatctggac ttcaacttgg   1020
acaagacctt atacttcttt atcgccggcc gctatgagtt ctccaacaag ggtgctgacg   1080
tcttcctgga ggcattggct cggctcaact atctgctcag agtgaacggc agcgagcaga   1140
cagtggttgc cttcttcatc atgccagcgc ggaccaacaa tttcaacgtg gaaaccctca   1200
aaggccaagc tgtgcgcaaa cagctttggg acacggccaa cacggtgaag gaaaagttcg   1260
ggaggaagct ttatgaatcc ttactggttg ggagccttcc cgacatgaac aagatgctgg   1320
ataaggaaga cttcactatg atgaagagag ccatctttgc aacgcagcgg cagtcttccc   1380
cccctgtgtg cacccacaat atgctggatg actcctcaga cccatcctg accaccatcc    1440 gccgaatcgg cctcttcaat agcagtgccg acagggtgaa ggtgattttc cacccggagt   1500
tcctctcctc cacaagcccc ctgctccctg tggactatga ggagtttgtc cgtggctgtc   1560
accttggagt cttccccctcc tactatgagc cttgggggcta cacaccggct gagtgcacgg   1620
ttatgggaat cccagtatcc tccaccaatc tctccggctt cggctgcttc atggaggaac   1680
acatcgcaga cccctcagct tacggtatct acattcttga ccggcggttc cgcagcctgg   1740
```

```
atgattcctg ctcgcagctc acctccttcc tctacagttt ctgtcagcag agccggcggc    1800
agcgtatcat ccagcggaac cgcacggagc gcctctccga ccttctggac tggaaatacc    1860
taggccggta ctatatgtct gcgcgccaca tggcgctgtc caaggccttt ccagagcact    1920
tcacctacga gcccaacgag gcggatgcgg cccaggggta ccgctaccca cggccagcct    1980
cggtgccacc gtcgccctcg ctgtcacgac actccagccc gcaccagagt gaggacgagg    2040
aggatccccg gaacgggccg ctggaggaag acggcgagcg ctacgatgag gacgaggagg    2100
ccgccaagga ccggcgcaac atccgtgcac cagagtggcc gcgccgagcg tcctgcacct    2160
cctccaccag cggcagcaag cgcaactctg tggacacggc cacctccagc tcactcagca    2220
ccccgagcga gcccctcagc cccaccagct ccctgggcga ggagcgtaac taagtccgcc    2280
ccaccacact ccccgcctgt cctgcctctc tgctccagag agaggatgca gaggggtgct    2340
gctcctaaac ccccgctcca gatctgcact gggtgtggcc ccgcagtgcc cccacccagt    2400
ccgccaaaca ctccaccccc tccagctcca gtttccaagt tcctgcactc cagaatccac    2460
aaagccgtgc ctttctctgg ctccagaata tgcataatca gcgccctgga gtccctggg     2520 cctggaccgc ttcccagagg ccaggaatct gccattactc tgcggtggtg ccagaggttt    2580
taggaaacct ggcatggtgc tttcaggtct ggggcttta gagcccccg tgtggcttac     2640 aaattctaca gcatacagag caggccacgc tcaggcccgg catgcgggcc accaagttct    2700
ggaaaccacg tggtgtccct gcgaatgggg cgatcaagtc cagagccggg gcactttcag    2760
agtttgaagg taactgagag cagatggtcc tccatttcaa ctccagaagt ggggctctgg    2820
gagggatgtt ctagccctcc ctggcatgtc agagccaggc tctgcctgga ggatccctcc    2880
atccggctcc tgtcatcccc tacactttgg ccaagcaaga ggtggtagaa ccacttggct    2940
gctcattcct tctggaggac acacagtctc agtccagatg ccttcctgtc tttctggccc    3000
tttctggacc agatcctact cttcctttct aaatctgaga tctccctcca gggaatccgc    3060
ctgcagagga cagagctggc tgtcttcccc caccctaac ctggcttatt cccaactgct     3120
ctgcccactg tgaaaccact aggttctagg tcctggcttc tagatctgga accttaccac    3180
gttactgcat actgatccct ttcccatgat ccagaactga ggtcactggg ttctagaacc    3240
cccacattta cctcgaggct cttccatccc caaactgtgc cctgccttca gctttggtga    3300
aagggagggc ccctcatgtg tgctgtgctg tgtctgcacc gcttggtttg cagttgagag    3360
gggagggcag gaggggtgtg attggagtgt gtccggagat gagatgaaaa aaatacatct    3420
atatttaaga atcccaaaaa aaaaaaaaaa aaa                                  3453
```

<210> SEQ ID NO 5
<211> LENGTH: 1276
<212> TYPE: DNA
<213> ORGANISM: Homo sapiens

<400> SEQUENCE: 5

```
agtgacgctg cggcctcctt ctgcctaggt cccaacgctt cggggcaggg gtgcggtctt      60
gcaataggaa gccgagcgtc ttgcaagctt cccgtcgggc accagctact cggccccgca     120
ccctacctgg tgcattccct agacacctcc ggggtcccta cctggagatc cccggagccc     180
cccttcctgc gccagccatg cctttaaacc gcactttgtc catgtcctca ctgccaggac     240
tggaggactg ggaggatgaa ttcgacctgg agaacgcagt gctcttcgaa gtggcctggg     300
aggtggctaa caagggtgta tttcgggcgc tggctgatcg agggaggccc tctggtggtg     360
ctcctggacg tgggtgcctc agcttgggcc ctggagcgct ggaagggaga gctctgggat     420
```

```
acctgcaaca tcggagtgcc gtggtacgac cgcgaggcca acgacgctgt cctctttggc    480
tttctgacca cctggttcct gggtgagttc ctggcacaga gtgaggagaa gccacatgtg    540
gttgctcact tccatgagtg gttggcaggc gttggactct gcctgtgtcg tgcccggcga    600
ctgcctgtag caaccatctt caccacccat gccacgctgc tggggcgcta cctgtgtgcc    660
ggtgccgtgg acttctacaa caacctggag aacttcaacg tggacaagga agcaggggag    720
aggcagatct accaccgata ctgcatggaa agggcggcag cccactgcgc tcacgtcttc    780
actactgtgt cccagatcac cgccatcgag gcacagcact tgctcaagag gaaaccaggc    840
atctggactt caacttggac aagaccttat acttctttat cgccggccgc tatgagttct    900
ccaacaaggg tgctgacgtc tttctggagg cattggctcg gctcaactat ctgctcagag    960
tgaacggcag cgagcagaca gtggttgcct tcttcatcat gccagcgcgg accaacaatt   1020
tcaacgtgga accctcaaa ggccaagctg tgcgcaaaca gctttgggac acggccaaca   1080
cggtgaagga aaagttcggg aggaagcttt atgaatcctt actggttggg agccttcccg   1140
acatgaacaa gatgctggat aaggaagact cactatgat gaagagagcc atctttgcaa   1200
cgcagcggca gtctttcccc cctgtgtgca cccacaatat gctggatgac tcctcagacc   1260
ccatcctgac caccat                                                   1276

<210> SEQ ID NO 6
<211> LENGTH: 31000
<212> TYPE: DNA
<213> ORGANISM: Homo sapiens

<400> SEQUENCE: 6 ttttttttt ttttgagaca cagccttact ctgtcaccca ggctggagtg cagtggcgcg     60
atctcggctc actgcaacct tcgcctcccg ggttcaagca attctcctgc ctcagcctcc    120
agagtagttg ggactacagg catgtgccac cacgcccggc taattttttt tgtattttta    180
ataaagacgg ggtttcacca tattagccag gctgctctca aactcctgac ctcatgacct    240
gcccgcctcg accccccaaa gtgctgggat tacaggtgtg agccaccgca cccggcctaa    300
ttttcttatt tttttgtaga gacagggttt cgctatgttg ccaggctag tcttaaattc    360 ctgggctcaa gcaatccttc tacctcggac tcccaaagtg tgggattaca ggcgtgagcc    420
actgtgccca gcccacaggt ctttcttctc ttcttcccct agagaggaca tgcagttatc    480
cagcccagag gaagcctcct ccctctggag ccaatcgttt agactttctg gccatcaatg    540
gtcacaagct ttccctgtca ctgtgtgaac cttcccacct accgtctcct ataggaagct    600
ggaacccagg agcatagaac attaccccca gactacaagc agaagactag gcatccccac    660
cccacaaaaa agacatgaat ccaggaatcc caaatgtagc tctctcaaca taaacaggcc    720
ccttaccaag gactgtctcc tataaagact ttctctttca tcataagtct ctccaaaacc    780
ttgctgcccg ctgttcccat gaaaccaag gtcatttcaa aactcagcac acaccgtccc    840
ctcatacttc caatactttc tccacggtag ttctggtcat agccttcctc ttctacttcc    900
ctatccacct cctcctcctc cttgccctgg tgacagcaac agactcaaat tcatccccca    960
gctaccaaca actttctccc cctcccttcc tccatcttga ctgggctcat catggaaatt   1020
gaggcacctg taagcccagc ccagtcccta agttcaggtc acattacctt tttttttttg   1080
gagacagagt ctcgctttgt cgcccaggct ggaatgcagt ggcgcgatct ggctcactg   1140 caacttctgc ctcccaggtt caagcgattc tcctgcctca gccttctgag tagctgggat   1200
```

```
tacaggcctg caccaccaca cctggctaat ttttgtattt ttaatagaga cggggtttcg   1260
caatgttggc cacgaactcc tgacctgaag tgatccgccc gcctcggcct cccaaagtgc   1320
tgggattaca ggcatgagcc accacgccag gccaaaatcg cttctttatt caggtaattg   1380
agcaggtgcc aggccaagtt tcctggcctc tccttcattc acatgtattc attcattcaa   1440
atattcaagt gataatttat tgagcattta cactgagacg tagcccgtgt gaaatactgg   1500
aaatatgaaa atggccaaaa cggtagcatg acaagatccc gatttctggg tccctaatcc   1560
ttcagtcctc tccactaaga ctctcttgtt cctcgacaat ttcttcccac taaaggctca   1620
ctaggcgccc tcgcgctctc agacacactg aacaggtacc tgcctgtgct tccagcttgg   1680
aactcaagtg ccattggcac cactaacaat ccaaggctcc caaatggctc gaagcgcaag   1740
gtcctacaac cctcctcatc acacactggc gccaaggact gcggaaccgg ccgttgcgcc   1800
aagatgattt tgaaagttgg agttcctata gcatgatggg gccagacccg agattctggg   1860
atcccagccc cctccccgcc tcagatccag aagtccagcc cccatgtccc cttctccccc   1920
agatctgggt ggccgagctt cctcctcttt cagacccagg agtctgaacc cccagatccc   1980
ccctccctca gacccaggag tcagggcctc cagcatcctc ctctctcaaa ctcgagactg   2040
ctagctcgct cctcacccct catgcaccca cacttacaac ggttgccatg atgctcacca   2100
actgccagag tcctagcgga aacgaaacg cgcgaggagc gagatgttct ggctcctcta   2160
ggctagctgg ttcttcaaag atctcgatgg ttcctcataa atatgtaaat attgtggggg   2220
cgtggcggga ctttatgccc cgccctccca ccgaggctgc gctggaagac gggcgtccgg   2280
aactcctggg tccattccca atgtctcctg gctcctcctc cttttgctca gccccaccac   2340
cgccccgctc aggccgattg caaaattctt agctgttctt tgagtaacca cacgtcctcc   2400
acgctccttt cctctttatc ccaccctcct cctcctcccc actttgaggc ctccagctcc   2460
agattgacag agctgaaggc cactcgtttc cgtaaagcgc agcggcaagc tccgcccct   2520
ggaggtctca cggccgaggc ggggccggga cacagcgact ccaacccgtt ccaccaatga   2580
ggacacgcgg aaatccccgc cccgggcgt gggccaatgg cgctggctgg ggggggcggc   2640
caccgcctcc tggcggctgc gaggtttcac tgcaggggcg ccagtgggct cagtgacgct   2700
gcggcctcct tctgcctagg tcccaacgct tcggggcagg ggtgcggtct tgcaatagga   2760
agccgagcgt cttgcaagct tcccgtcggg caccagctac tcggcccccgc accctacctg   2820
gtgcattccc tagacacctc cggggtccct acctggagat ccccggagcc ccccttcctg   2880
cgccagccat gcctttaaac cgcactttgt ccatgtcctc actgccagga ctggaggact   2940
gggaggatga attcgacctg gagaacgcag tgctcttcga agtggcctgg gaggtggcta   3000
acaagggtga gcacgccagg cgtcggggcc cttgacgaga aggacagtag tggatggggg   3060
cccggaactc tgagttgtag gaggacgggg ctactagggg aacccttgtg acctgggcaa   3120
ggaggctgtg tccttgagga ggggctggga agcggaggt gggtgggaga gggatggttc   3180
gtttgactta agatgaaagg aggctggaag cccgggttct gggtcctagg gaagagggcg   3240
ctaaaatgag actcctaggt cctggaggca ggcttccgag agactagata cctgggtcct   3300
gaacagggaa ggggatgggg ggatgggatt tctgcgtgca aacctgggaa gctgccgggg   3360
tttcagacct atgaccctaa cagcatggtc tagggataa aactccagat ttgagagaga   3420
gctgactggg agataggagg cctgagcggc ggtggggagga cctgaggatc tggctgctta   3480
agaataaaga tgggacgggc tggagactgt aatgaatgcc tgggctttga aggagctgag   3540
ggcctgagct attagttcct aggagtagag gagcccatgg cctgggacac atgcgtactg   3600
```

```
gaatagggga aggctgggaa gtcctaagtt agtcagaggc tgggccctag gatgggaggg    3660
gctaggagcc tgcatttctg tgtcttgggc ttcagaaagc tgaggttctg gccttggaga    3720
aggctggggc tgaaatcccc aggaacaagc caatctcaca cctcaaagag cagggtctgg    3780
ggggttgctt tgctgggtct tggaggagaa agggactgtg tctcccagga ggagagggga    3840
cccgtgaaca cccagccggg tatcgccagg gcctgggctc caggatggga ggaggctggg    3900
ggctggggct cctgggtctg ggatagggtc atgggagagg cagagccctg catgctggtg    3960
tccctagtca gggagaggaa attgggaggc aggtcagcaa ggtccctggg ggcagggaat    4020
gaccatgcag gcttctcttg ggcaatggtg agaagctgga ttggccatga gggggtctcc    4080
ctcactgggt tttggagcct ggctgcgatt taaacccagc tcctgtgagc tgggaactcg    4140
ggaacctgag tccgggtagt cagtcctcag ctctgccatc cttagagccc cagtgcctaa    4200
ttccttcaga ccaaggggtc ccggcaccca gccccttctc tctcagaccc agaagtctag    4260
cctgagcccc ctcctccttc agggtcctga ccccagcccc cttctccctt agacccagga    4320
ggactgccct ccagccctcg tgttcccctc atccaagctt ccaaccccta ctccaaacta    4380
tgggctccca gtccctctt cccctgagc tagaggtctg gggcctgagt gccccctaca    4440 tcccggccc accccacccc aggcccaga actatggacc tcggccgggg cctgccctca    4500
cacgcttggg cccacagtgg gtggcatcta cacggtgctg cagacgaagg cgaaggtgac    4560
aggggacgaa tggggcgaca actacttcct ggtggggccg tacacggagc agggcgtgag    4620
gacccaggtg gaactgctgg aggccccac cccggccctg aagaggacac tggattccat    4680
gaacagcaag ggctgcaagg tgggacgtgg cccagcccag ggcagaagcg ggtggacagc    4740
ctgccatcgg ggtgggagcc acagacggag agggtgcagg gtggacagcc ccagccagag    4800
agcgaggcag gcttggacac aggaaggagg cgtgatagga cacccagaca gatgcagggc    4860
ctggaagtgg gtgggtggat cccagacatg ggcgaatgga cagacagatg gcaagtatga    4920
gacagactga gacggagatc caagaggcca aggtcctcag acccagagag aaagagagca    4980
agatcgaaag acagcctggt caacatggcg aaacccgtc tctaccaaaa atacaaaaat    5040
tagctgggtg tggtggcggg tgcctgtaat cccagctact cgggaggctg aggcaggaga    5100
atcgcttgaa cccggggaggc ggaggttgca gtgagctgcg attgggccac tgcactccag    5160
cctgggcgac ggagcgagac tctgtctcag aaaagaatgc cagccagcca ggcagagctg    5220
gggagaagtg ggcctgaggt caggaaggag caggattctg gagcttgaag ttcaagttca    5280
ccctccactt gctgcctgtg tgtccttggc taatggacat gctaatagcg tctaccttct    5340
agcggtgctg ggaggaggaa acagttaata aggacaaagt ggttagtaga gttcttggca    5400
tgaaggtagc acattgtgtg ggcggtgatt gtcattgtta tgatcatcgt cattattgtt    5460
actaacagcc aagcttggag agtgaggggg acaggcagac caaggagaa gggtggatgg    5520 agccacaggc aagagtaata gactgggac agaagagagg ccaccagatg tttcagaaag    5580
ccagtcctag aaggagagag aagcatggaa tatcgggaa gagaggagag gtcagtggac    5640
agacccacag gacagagtct gagatgggca gatcagggat tagagaggag ggggagttcc    5700
agggccccag ggtgaagacg gaaagagaca cgctgttgtc caaggagaaa gccatcaggc    5760
ggcacgctgt tgtccaagga gaaagccatc aggcggcagg gctaagggac agacaggtcc    5820 aggctggggga tggagaggca ctgtggttcc tttactcatt cacagcctct ggtttggggt    5880
ggggtctgga atccattcag gtccgactgt gtccctaagg gaacccagaa cagcccagtc    5940
```

```
gcttcctgag ggcagctgct tcccacgtgc tgggggccta agaatagccc cccccccccc   6000
ccagcaaaag ggcagacaac agctgggagg gggaggggacc tcagagcgag gctccaggca   6060
gcaaaaagcc aggtcggcga ggagcggggc tgcttctcca ctgctgtggc agcaggccca   6120
gaaccaaagc catggtctca gggaggaaaa cagccaactg gagaaatgtg gcagaggcag   6180
aagtgagaca gcaagtctta gaaacacggc agtggctaga aaaatgcagc cctggggcac   6240
ggacagagga tgggctatgt tagaaatgtg tggcgtggcc gagggcgtg gctcatgcct    6300 ggaatcccag cactttggga ggccgaggtg agaggatagc ttgagcccag gagttcctga   6360
cccacctggg caacatggcg aaactctgtc tctactaaaa atacaaaaaa ttagccaggc   6420
atgatggtgc gtgctcgtga tcccagttac tcaggaggct gaggtgggag gatgggatgt   6480
ggaggctgta gtgagccata atttttttt ttttttttc agatagaatc tcactctgtc     6540
gctgagtctg gagtgcagtg gtacaatctc gactcactgc aacctccgcc tcccgcgttc   6600
aagcaattct cctgcctcgg cctcccaagt agctgggacc tcaggcacat gctgccacgc   6660
ccggctaatt ttttgtattt tagtagagac agggtttcac catgttgccc aggctggtct   6720
caaactcctg agctcaggca atccgcccgc ctcggccccc caaagagcta ggattacagg   6780
cgtgagccac cgcgcccagc ccagtgagcc atgattgcac cactgcactc cagcctgggt   6840
gaccggagtg agaccctgtc aaaaacaaaa acaaacaaaa aaaatggaa gaaagaaaga    6900 aaaggagag agggagggaa ggaggggagag agggaaggaa ggaaggaagg aagcaaggaa   6960
ggaaggaagg aggctgtgga ctacaaaatg ggcctatgga tagaggaaag aggtcgcagg   7020
tgacagatat gtgatgaaag gaacagaaac aaggcatcat ggggaagaaa agtggcagca   7080
tgaacagtaa gagaatcatt acaggctggg tgcagtagct cacgcctgta atcccagcac   7140
tttggtaggc tgaggccagg agtttgagac cagcctgggc aacatggtga aaccctgtcc   7200
ttacaaaaaa gttaaaaatt agccgggatg tgataccttg tgcctgtggt cccagctacg   7260
tgggaagctg cggtggaagg attgcttgag cctgggagat cgaagcttca gtgaaccgta   7320
attgcaccac tcccttccag gctggaggac agagcaagac cccgtctctg aaaataaaaa   7380
agggcctgct ttaggtggct cacacttcta atctcaacac tttgggaggc taagcaagaa   7440
aactgcttga acgcaggagt tcacgatcag cctgggcaac atagtgagac cccatctcca   7500
caaaaaatta aaaatcagc ctggcatggt ggcccacgcc tgtaggaggt gaggtgggag    7560
gattgactga gccagggagg ttgaggctat agtgaaccat gttcacacca ctgcactcca   7620
gcctgggcaa cagagcgaga ccctgtctga aaacaaaaaa gaagcatccc gtggaaggaa   7680
ttagcatcag aaagaaaaga cagtgggaga tgcagatggt tggtaagaga aatgtggcag   7740
caagtacaga aacaaggcag caggtagggg aaatgatttg cagagtggcc agacagggca   7800
gtgggggcat agacacagga catgtgacat atgtggttat aagcagagaa aggaggcagc   7860
gagtgggaga agggtagcag ttacaggaat taaacaggag gctgggtgcg gtggctcacg   7920
cctgtaatcc cagcactttg ggacgccgag gcgggcggat cacaaggtcg ggaaatggag   7980
atcatcctgg ctaacacagt gaaacctcgt ctctactgaa aatacaaaaa aaagtagccg   8040
ggcgtggtgg cgggccgctg tagtcccagc tactcgggag gctgaggcag gagaatggtg   8100
tgaacccagg aggcagaggt tgcagtgagc cgagatcatg ccacggcact ccagcctggg   8160
caacagagcc agactccgtc tcaagaaaaa aaaaaatta gccaggtgtg ggagcgggtg   8220
cctgtaatcc cagctacttg ggaggctgag gcaggagaat tgcttgaacc cgggagacag   8280
aggttgcagt gagctgagat cgcaccactg cactccagcc tgggccacag agtgagactc   8340
```

```
catctcaaaa aaaagaaaga aagaaagtaa gcaggggggca cggaaaatat tgcaacagag    8400
atggaaaaaa tgtgtagcag gaataaatca tgcaaataga gaagtaaggc taaggcagca    8460
ggtgagaaat tagcagcaga tatggaaaca gaagataaga gagctgaggc ttaagtctat    8520
agacatctgc ctgcaaatgg gagaaccacg gatgagtgaa gatatgaggc tgaagcccag    8580
agcctcccta tggtgcctcc ccaaccccat cccaggtgta tttcgggcgc tggctgatcg    8640
agggaggccc tctggtggtg ctcctggacg tgggtgcctc agcttgggcc ctggagcgct    8700
ggaagggaga gctctgggat acctgcaaca tcggagtgcc gtggtacgac cgcgaggcca    8760
acgacgctgt cctctttggc tttctgacca cctggttcct gggtgaggta ggccccgtct    8820
gacacattcc acccatacct gaaactacaa tgaccatcag cccctgggcc agaggatggg    8880
cttctccctg ggcattctgg gagtcatagg gtcctttaat ccaaggatta gctctggcct    8940
ttgaggacat gaacatccaa gggcccaggc tctactctcg atgccaactt catttactct    9000
agtcttccaa gcatagggat tcttggaatc agcctcaaag tgaggctggc gggcttgccc    9060
gaggaattct aggagttgta gttctctagt gtgatattgc tggactcagc tctcagatgc    9120
tgccctggat gctcatgaat ccccagcctg acctggtttt gacccccttc taggttttaa    9180
gaggctcaag aagcttagtt tccaggctgg gcacggtggc tcatgcctgt aatcccagca    9240
ctttgggagg ccgatggggg aagatcacgt gaggccagga gttcaagatg gccaaacctc    9300
gtctttacta aacatacaaa aaaattagct gggtgtggtg gtgggcacct gtaatcccaa    9360
atcccagcta cttgggaggc tgagacagga gaattgcttg aacctgggag gcgggaattg    9420
cagtgagctg agattgcatc acggcactcc agcctgggcc acagagtgag acactgtctc    9480
aaaaaaaaaa agaaaaagaa aaaaaaaaaa agaagcttaa tttctcatgc cctgggacaa    9540
ataattgagg aactggctgc tcctatggca ttctgggagt tgtagtccct ttgccaatgt    9600
tgggtgcaga cagcgtaccc ttgagacaag gggtctttgg aaactatgtc caggacctgg    9660
gaacatgaaa acttcagtct gtccaatcta accctgccag gacttagatg gttggccaaa    9720
aaatcctcag ttcctgtcaa cccctgagga ggcagtcact tgagcccagg agttcaagac    9780
cagcctgggc tgcctcaggg atttacaggt ccctgtccgg ttgggattgc tgcagtgggc    9840
cgctgcccac tctgtgcagt agtggtgaca gattgacctc tccccgagtc cttgtcccta    9900
ctggggattg ccgattcttt tcccaacact cgtggagaca gtggccctgt ccctgttgcc    9960
cacagttcct ggcacagagt gaggagaagc acatgtggt tgctcacttc catgagtggt   10020
tggcaggcgt tggactctgc ctgtgtcgtg cccggcgact gcctgtagca accatcttca   10080
ccacccatgc cacgctgctg gggcgctacc tgtgtgccgg tgccgtggac ttctacaaca   10140
acctggagaa cgtgagctgg gaccgtgcca gatggggac tgcgagtatg ccaggaaaac   10200
ccaaagctct gggggggccca aggggatggc accccctctt ctcccaggat ccaggagtcc   10260
aagtccccag accctcccta cctcagaccc aggaatccag ccccagcac caatttctct   10320 tgggacccca gtgtctggac ctccagagtc ttctccccaa tccttctaac cggactgctg   10380
tcccctccca cccagttcaa cgtggacaag gaagcagggg agaggcagat ctaccaccga   10440
tactgcatgg aaagggcggc agcccactgc gctcacgtct tcactactgt gtcccagatc   10500
accgccatcg aggcacagca cttgctcaag aggaaaccag gtagggctgg ggctgaagtc   10560
cccagacgtg aatgaggtag gcagctgtct atgccaaagc cagttgctcc tcagcccaag   10620
aagcccactg taagttgaaa tagcataaac cgaaaacgta tttcggctgg gcatggtggc   10680
```

```
tcacacctgt aatctcagca ctttgagagg ccaaggcagg agaaccactt gagcccggga    10740
atttgagacc agcctgggca acatggcgaa tccctgtcta aaatattcgc cagacatggt    10800
gtgtgcctgt atccctagct actcaggagg ctgaggtggg aggattgctc gagcctagga    10860
ggtcaagggt gcagtgagct gtgatcgtgc cattgcatga tttgggtggc ctggagagac    10920
cctgtcacag cctgggtgac acagtgagac cctgtctcaa aaataaaaa aatgcattta     10980 atacacctaa cctactgaac atcatagctt aggctagtat accttaaatg tgcccagaac    11040
actttatgtt agcctacgac tgggcaaaat catccaatac aaatctgttt tattttattt    11100
ttatttattt atttattttt gagacggagt ctcgctctgt cgcccaggct ggagtgcagt    11160
ggcgctatct tggctcactg taagctccgc ctcccaggtt catgccattc tcctgcctca    11220
gcctcccaag tagctgggac tatacgcgcc tgccaccacg cctggctaat tttaatacaa    11280
acctatttta taataaagtg ttgaataggc tgggcgcagt ggctcacacc tgtaatccca    11340
acactttggg aggccaaggc gggcagatca cgaggtcagg agatcgagac cagcctggcc    11400
aacatggcga aactccatct ctactaaaaa tacaaaaatt agccgggcgt ggtggtgggt    11460
gcctgtaatc ccagctactc gggaggctga ggcaggagaa tcacttgaac ccaggaggcg    11520
gaggttgcag tgggccgaga tcacaccact gcactccagc ctggacaaca gagcgagact    11580
ccatctcaaa aaattaaaaa aaaaagtgt tgaatatctc atcaaaatcc aaaattggac     11640
tcatgtggat gtatgtaact ttcacaccat cataaggttg aaaaatcata acttggctgg    11700
gcacggtggc ttacacctgt aatcccagca ctttggaagg ctgaggtggg cagatcacct    11760
gaggtcatgt gctcaagacc agcctggcca acattgtgag accccctctc tgccaaaaat    11820
acaaaaatta ggtgggcatg gtggcaggcg cctgtaatcc cagccaccca gctactcggg    11880
aggctgaggc aggagaatct cttgaaccca ggaggcagag gttgtcgtga gccaagattg    11940
tgccattgca ctccagcctg gcaacaaga gcgaaactct gtctcgaaaa gaaaaatcat     12000
aacttggacc atcctaagtc ctaagctggg gaccatcagt taccattttt ttacctaaag    12060
aatagagaac tacagctccc agaaggctgt gggggtggtg acctgtattt gaggctctct    12120
gactatatac tctggaggct aatgggaggt ataatttctt tcatattaat ttcagatatg    12180
ataaaattct gtaattggct aatgtagatt ggtcttatga aagggaatgg aagatcagtg    12240
gactttgctt ttgagaaagg ttaggtcaga actgggcatt cttcccagcc cttagtatcc    12300
gttctcagtg agtataaggt gagaactaca actcccagaa ggcctttgac tggttagctc    12360
tatatgttcc agaactttgc cctaggcgct gatgggggtt gtagtttttc gttgatatac    12420
tttaatttct atgaggagaa gaaatgattg gtccctgta agaagcttgg aagtagagga     12480
tatatcctag gagaagcagg actttgggga tgtttaatca tttccatctc agggtgggct    12540
aagaggaaac aaaagaagta caactttccc agaatcacca gtgtggatca gatccctgtt    12600
agccatttgc agtagctgag gagacttata cttgtgcttg tgaacctaag caagtaatat    12660
taggcaagaa ggcatcttgg agtcagggta ggtgtgtcac caagggaact ggccaggcat    12720
ggtggctcac acctgtaatc ccagcacttt aggaggccag ggcaggaaga ctgcttgaag    12780
ccaggagttt gagatcagct tgggtaacat gacaagaccc catcactaca aaagtaaaat    12840
aaataaatta gccgggtgtg gtagtgcacg cctgtagtgc cagctactcg ggaggctgag    12900
gagggaggat tgcttgagcc caggaggtca gggatgcaat gagctgtgat tgtgccactg    12960
ctctccagcc tgagcgacag agagaaaccc tgtctccaaa aacaaacaaa caaacaaaaa    13020
aggtgggagg gggaccctca taggaacgct cttgaaacaa aaaaattgca aaaggcaaag    13080
```

```
ggtgttttct tcatttattc attcaaccac aacattgatc tgaatgaaca aataaaacat  13140
gggaccctca cccccaatcc cagatattgt gaccccccaat gggctgaatg tgaagaagtt  13200
ttctgccatg catgagttcc agaacctcca tgctcagagc aaggctcgaa tccaggagtt  13260
tgtgcggggc cattttttatg ggtacgtggg gcatatacct aggtcttaag agaggagggc  13320
gttgggagcc taaccatcta ggtctggggg aggggcagc tgggggccca gactcctggg  13380
tctgagggag ggggcacctg ggtattcggc ctccttaatt cttgagcgct ggaacaatgg  13440
gctcaggatt aaaggaaatc tccatctaaa gagaagaact acaactccca ggaggccccg  13500
tgatgcctct gtattaccta agacatcctc tgcccccca cccatagctt ctgggatttg  13560
tagttttgag ccagggcta gcgggtgagg gctttgggct ttaccgtgcc ttgtgggttc  13620
tttaggcatc tggacttcaa cttggacaag accttatact tctttatcgc cggccgctat  13680
gagttctcca acaagggtgc tgacgtcttc ctggaggcat tggctcggct caactatctg  13740
ctcagagtga ggcctgggct atgaggggac agggagggca agcaaagcag tttataacta  13800
gggagaacag ccaggcacag tggctcacac ctgtaatccc aacactttg gaggccaagg  13860 cgggaggatc acttgagccc aggagatgga gaccagcctg ggcaacatgg tgaaacccca  13920
tctctacaaa aaatacaaaa attagccagg catggtggct cacacgtgta gtcccagcta  13980
ctcgggaggg tgaacgggga ggatcacgcg agcccgggag gtggaggttg cagtgagcca  14040
agatcatatc actgcactcc agcctgggcg acagaaaaag acgctgtctc aaaaacaaaa  14100
caaaacaaaa caaaacaaaa aattacagaa cagaaaccca agaagccagg aagatggggg  14160
taggaaagcc cctgagtatg gtgggggggcc gtgagggggag tatagagacc cagaaagaag  14220
gtcagagtcc aggtggggac tgtcctataa ttctccttga caggaatggg tatggcagga  14280
tcccagtggt cttgacagaa aggctggctg gttccaggct tcccccacat gatcctggcc  14340 tcccctcct ttctttctgc gcaggtgaac ggcagcgagc agacagtggt tgccttcttc  14400
atcatgccag cgcggaccaa caatttcaac gtggaaaccc tcaaaggcca agctgtgcgc  14460
aaacagcttt ggttagcagc cctcgctccg gcccctggcg cagcccactc ccagatgcat  14520
gctttgggtc ctgtgtttct cctagagtct cagttttttg ttttgtttgt ttgtttgttt  14580
gtttgttttt gagacagtct cactctgtcg cccaggctgg agtgtagtgg tgcgatcttg  14640
gctcactgca acctccacct cctgggttca agcaagtcat ctgcctcagc ctctcgagta  14700
gctgggacta caggtgcaca ccaccatgcc tggctaattt ttgtatttc agtagagatg  14760 gggtttcacc acattggcca gactagtctc aaactcctga tctcgtgatc tgcccgcctc  14820
agcctcccaa agtgctggaa ttacaggcat gagccaccgc acccggccct cttttttttt  14880
tttattttga gatggagttt tgctctgtcg cccaagctgg agtgcaatgg catgatctcg  14940
gctcactgca acctctgcct cctgggttca agcgattttc ctgcctcagc ctctgagtag  15000
ctgggactac aggggtgtgc caccacacct ggctaacttt ttattttat tagagacagg  15060 ttttcactat attggccagg ctggtcttga actcctgacc tcaggtgttc cgcctgcctc  15120
agcctcccaa agtgctggga ttccaggcgt gagccaccac acctagcctt ttttgtatt  15180 tttagtagag atggggtttc accatgttgg ccaggctgat cttgaacacc tgacctcagg  15240
tgatccagcc gccttggcat cccaaagtgc tgggattaca ggggtgagcc actgcgcctg  15300
gcttagtttc ttttttcttt ctctgatttt tttttttttt tgaaacagag tctcactgtt  15360
gcccaggctg gagtgcagtg gcgtaatctc agctcactgt aacctccgcc tcccagcaaa  15420
```

```
gctcagtttc ttcatctgta aaaccgttca ttcattagca gagatactca ctgagcatct    15480
actatgtgct agctaatttt tatatttta gcaccgatgg gatttcacca cgttgaccag    15540
gctggtcttg aactcctgac ctcaagtgac ctgccctcct catgtattcc aggtcctggg    15600
aatacagctg tgaaccagaa agataagatc cctttcctca tggagcttgt attctagaaa    15660
atcctgtaga cggaatttac ttttgggcaa aaataaagca gaactggaat atgagacggg    15720
gttgtcagga caggccacac tgagaaagtg ttattgggca gagacgagga aaggtgacga    15780
gggagcaagc cctgtgggta tctgaggaac agcaaactcg aaggccccga ggcatgattg    15840
agacgcggtg gggagtccca tggggctgga gtgacatgtc tcatagagaa ggggtagaaa    15900
gtgaggcaag atggagggca cctgtagtgc cagctacagg aggcaggagg atcattttgg    15960
ccctggaggt tgaggctgta gtgaggcatg attgcgccac tgcactccag cctaggcaac    16020
agagtgagac tctgtctcaa aaaataaaa aagaagtcgg gcgtggtggc tcacacctgt    16080
aatcccggca ctttgggagg ccgaggcggg tggatcacct gaggtcggga gtttgagacc    16140
agcttgacca acatggtgaa accccgtctt tcctaaaaat aaaaaaaatc agcagggcgt    16200
ggtgacacac atctgtagtc ctagctactc gagaggctaa gcaggagaat cgctcgaacc    16260
cgggaggcag agattgcagt gagccaagat cgcgccaatg cactccagca tgggtgacag    16320
tgagactcgg tctcaaaaaa aaaaaaaaa aaagaaaga agaggctgg gcgcggtggc    16380 tcacacctgt aatcccagca ctttgggagg ctgaggaggg cagatcactt gaggtcagga    16440
gttcgagatc agcctggtca acgtggtgaa atcccatcgg tactaaaaat ataaaaatta    16500
gccagatgtg gtggcgcacg cttgtaattg cagctactca ggaggctgag gcaggagaat    16560
ttcttgaacc tagaaagtgg ccgagattgc gccatcctgg gcgacagagc aagactctgt    16620
ctcaaaaaaa aaaaaaaaa aaaaaaaaa aaaaaaaaa aaagaaaag aaaaagaaa    16680 aagagacaaa gaaagaaaaa taatgaggc cagagctatg ggaggatttt aagtggagga    16740
gtgaccgtgg ggctgttgtg tgacactgct agctttactt gtgtgcctaa gtggtccttt    16800
ctcagaatct tactttcttt tcgtataaaa tggggcttag cattgccatc tgcaggacaa    16860
gtacaagtcc taataatagc tgacatttct ggaaggcttg ccatgtgtac tttttggcat    16920
gacatcattg ggtcctcatc gcaaacctct gaggttgatt ctatttcat cctcctctga    16980 aaaatgagtc actgcagtca gagagggaag gccacctgtc cctgaccaca cagctgatgt    17040
caggcacgtg ggtcctaagc cttccagggc ctgcccctg ggtccccatc ctccagcctg    17100
gaggccccag ggcacggctt ccctgctcac acctcagttt ccttgctatc ctagaaacct    17160
aagggtagct gggcgcggca gctcatgcct gtaattccag cactttggga ggccgaggtg    17220
gccaattacc agccagaggt caggagttcg agaccagcct ggccaacgtg gtgaaacccc    17280
gtctctacta aagttacaaa aattagccgg gcatggtggc aggtgcctgt aatcccggct    17340
actcaggagg ctgaggcagg agaattgctt gaacctgaga ggcagaggtt gcagtgagcc    17400
aagatcgcac cactgcgctc cagcctggac gacagagtaa ctctgtcaat aataataata    17460
ataataataa ataaactgct gggcacagtg gctcaagcct ctaatcccag tactttggga    17520
ggccgaggtg ggcagattac ctgaggttgg agtttgaga ccagcctgac caacatggag    17580
aaaccccgtc tctactaaaa atagaaaatt agccgggcgc ggtggctcat gcctgtaatc    17640
ccagctactc gggaggctga ggcaggagaa ttgcttgaac ctgggaggca gaggttgcag    17700
tgagccgaga tcacgccatt gcattccagc ctgggcaaca agagcaaaac tccgtctcaa    17760
aataaacaaa caaactaact aaagaagcct aacagtaaat ggcagctggt gtgtatgtga    17820
```

```
ccctgttgct ctgcttcctc cagggacacg gccaacacgg tgaaggaaaa gttcggagg    17880 aagctttatg aatccttact ggtgtgagtg ccccaccctc agccctgtgc cctcctaggc    17940
cctgactaac ccctctcatt actccgttct cacatgcatg cccctgcttg ccttgcagtg    18000
ggagccttcc cgacatgaac aagatgctgg ataaggaaga cttcactatg atgaagagag    18060
ccatctttgc aacgcaggta tggattggac ctctgtgcag agagatagca gttcctggca    18120
gccccagagg cagcttgcca ggccagctca gaccccagag attgctggga gtcctgcttt    18180
ctcctgcagc cctttatgaa gggatctatt ctgaggtcca cagaagggca cgtgctgact    18240
cgtgcaactt cagttgctgg aggcgaggca cttagggtgg gctgttttct gtggcttatt    18300
ctgccacgag ggttgctggg acgtgtggtt tctctgggat tctgggtca atgagcaaaa    18360 ggaagcttat ttgtttattt attttttatta tatttattta tttatttttga gatggagtct    18420 cgctctgtcg cccaggctgg agtgcagtgg cacgatctcg gctcactgca acctctgcct    18480
cctgggttca gcaatactc ctgccttggc ctcccaagta cctgggatta caggcacatg    18540
ccaccacacc cagctaattt atatattttt agtagaaacg agattcacc atgttggcca    18600 ggccagtctc aagctcctga cctcaagtgt tctgtctgcc tcagcctccc aaagtgctga    18660
gtttacaagc gtgagtccct gttcccagcc caaagggaag tttaaaagga agtgtagaaa    18720
tgtaataaag ggccaggtgt ggtggctcat gcctgtaatc tcagcacttt gagaggccaa    18780
agcaggaaga tcacttgaga ccaggaggct gaggctgcag tgagccatga ctgtgccact    18840
gtacaccagc ctgggggaca gagccagatc ccacactagc ccccacccca ccccaaaaag    18900
aaagtcaagg cccagcttgg tagctcacac ctgtcagtat tcccagcact ttgggaggct    18960
gaggtgggag gatcgcttga gcccaggagt ttgagaccag cctgggcaac atgatgaaac    19020
cctgtctcta ccaaaaatac aaaaatgagc tgggcatagt ggcatacacc tgttatccca    19080
gctacctggg aggctgaggc cagaggatgc cttgagctca ggaggtcaag gctgcagtga    19140
gctatgatta tgccgctgca gtgagctatg attatgccac tgcactccag actgggcaac    19200
agagcgaggc ggacacatac acacacacac gaaagaagga aaagaaagaa agaaaaggt    19260 caagacagcc ataaagaat tacaactctc agctctcctt gggccttgct gcacacggct    19320
ccacctctac ccctaaaact gctgggagtg gtagttttat cgggccactt tagggacgca    19380
gtcaggaggt gagcaaaagc acccagcatt ctccagaaaa cattgcaaac tctcagcagc    19440
tgcggtttct tatttccaga ggctgtgtgt tggtccccag acaccctgg gaattgtagc    19500 tgctttagat ccctaacttc agagagaatt ggcatttata aaatgagaac ttaccgtcat    19560
tctattgagt ctaggggccc aaaaaactac aactcccagc agccctgct ggctttctgg    19620 ggcattgacg cttcccttgt ccagaggctt ctgggagtta gagttctttc attctctggg    19680
gtccagggac ttcagtactt gtggtctaca ttggggagcc atttcctggg gaatggaaac    19740
ccagacagct aagttgtaga aacaaaacgt gaactgcttt tggctaacct ataatttcca    19800
atagtcccta aagcagccca cctcattatg aatgtttctg ccatcgggat gctgggagtt    19860
gtagtttctc gggcccctag actcagtaga gtggtggtaa gtaaaatctt taatgagcta    19920
tgatggaaca gttgctaaga actatacacc ccagcagtcc tcaggacttc ctatcacact    19980
agctctgtct tgctccagag actcttggaa attgtggttt cttgggcct tgttagggt    20040 tggaggtgaa ttttctttt tcttcttttt tttttttt tttttttg agacggagtc    20100 tcgctctgtc gcccaggctg gagtgcagtg gcgcgatctt ggctcacttc aacctccgcc    20160
```

```
tcccggattc atgccgttct cctgccccag cctcctgagg cacccaccac cacgcctggc   20220
taatttttg tattttagt agagacgggg tttcaccgtg ttagccagga tggtctcgat    20280
ctcctgacct cgtcatcctc ctgcctcggc ctcccagagt gctgggatta caggcgtgag   20340
ccaccacgcc tggtggttgg aagtgaattt tcataaggaa actacaactc ccagcagtct   20400
ccaaagcttg ctgccatatt ggcacagtct ccaccccat tgactgggga tagttatatt    20460
tcctttgggt ttctttaata atagagccca gagtacagaa caaggtagct gcaactcctc   20520
atagtccttg gaggtaaggg agttgctaac acggctttgc ctcaaagaca gctgggaatt   20580
ctagttcttt gaagctcatg gtggttaagg aaggaaaac atttccaggc caggtgtggt    20640
ggctcatgtc tgtaatccca gcacttcggg aggccaaaac ggatgcatcg cttgagccca   20700
tgagttcgag accaacttgg ccaacatagt gaaaccccat ctctattaaa aaaaaaaaa    20760
aaaaaatta ggctgagcgc aatggctcac gcctgtaatc ccagcacttt gggaggccaa    20820
ggcaggtgga tcacgaggtc aggagatcta gaccatcctg atttaacaca gtgaaacctc   20880
gtctctacta aaatacaaa aaattaaccg ggcgtggtgg taggcgcctg tagttccagc    20940
tactcgggag gctgaggcag gagaatggca tgatcctggg aggtggagct tgcagtgagc   21000
cgagattgtg ccactgcatt ccagcctggg cgacagagcg agactccgcc tcaaaaataa   21060
ataataataa tttaaaagaa aagaaagaaa acctttacag gttgtactag tgggaatcca   21120
caactcctgg tgatcacttg ggtttgttgc cccacgtccg gtgcatttgt ggtctccttg    21180
gctcccccag ggtccgcatg gctcatgagg aagtagggag ttctctgtcc cttccatgac   21240
cccttaccct tcttgtggct cctgcagcgg cagtctttcc cccctgtgtg cacccacaat   21300
atgctggatg actcctcaga ccccatcctg accaccatcc gccgaatcgg cctcttcaat   21360
agcagtgccg acagggtgaa ggtgagggca tttggtcagg gctgggttgg gcacggcaga   21420
gggaaggggt tgggtcctgg gcctcacaca ctccattccc ctataagtttt tatcaaaggt    21480
attgctgtgt ttagaaagaa ccctggcttc tgaggcaggc agacctgggt ttgaacattg   21540
gtcctgccaa acacatgctg tgtgatgcta gacaagcttt ttaccctctc tgggccacct   21600
tgggatctca gggcttagct aaataaggca cttgggctga gtccttcttt ttcactacca   21660
ggtgattttc cacccggagt tcctctcctc cacaagcccc ctgctccctg tggactatga   21720
ggagtttgtc cgtggctgtc accttggagt cttcccctcc tactatgagc cttgggcta    21780
cacaccgggt gagtgtagtg ggcaggggac agcgtggtca tggcatccta gtcagagcta   21840
gcatgtcttg gggcgaggca ctggccttct ctgagcctgt tgccttcttt gcaaaacagg   21900
aacaatggta atcacctgtt ctgctacagc gcgtgctttt gtgatacaat agctcatgta   21960
ttgagaaact agaagactgg gttttgagga ctagtgaact ggatgtcaca gttcacactg   22020
cttctctcca gaaagcagtg gccccccaaa tagtggcaat gaaatgcaca attcacaaat   22080
acagccgagt gtggccaagt ctcctcgtaa gacgttccca gtgcccatca actccacctt   22140
cctcttgttg gttcacatta gccagtgttt ttaaagctaa ataaggctgg gcgtggtggc   22200
tcatgcctgt aatcccagca cttggggagg ccaagatggg cagatcatga ggtcaggagt   22260
ttgagaccag cctggccaat atagtgaaac cctgtctcta ctaaaaatac aaaaattagc   22320
caggtgtggt ggtacgcacc tgtagtctca gctacttggg aggctgaggc agagaattgc   22380
ttgaacttgg gaggcggagg ttgcagtgag ctgagatcat gccactgcac tccggcagtg   22440
ctgtgctctg ggtgacagag cgagactccg tctcaaaaaa aaaaaaaaaa aaaaattaaa   22500
gctaaattag tgccatttcc taatttatta gtaatttaac aagtcctgca aactgtgctt   22560
```

```
gcatgataat taggagtcgc ggtcagcccc aattcccttt ttccataggc cttgttttat   22620
agatagattg atagatagta ctagtctgtt ttcacaccgc tataaaaaaa aaatccaaga   22680
ctgggtaatt tataacggaa agaggtgtaa ttgactcacc gttccacatg tctggagagg   22740
cctcagaaaa ctcagtcatg gcagaagggg aagaaagaag cttcttctca tggcggcagg   22800
agggagaagt atgtgagggt gcaggaaaaa cgaacattta taaaaccatg agatctcgtg   22860
agaattcact cactatcatg agaacagcgg cgggggaacc accccgtaa tccaatcatt    22920 tccctccctc gacacgtggg gactacattt tgagatgaaa tttgggggg aacacagagt    22980 caaactatat cataaatata tatttaatac attttactat ttgtttcttt tttgagatgg   23040
ggttattact ctgttgccaa ggctcacctg gaactcctag gttcaggtgc ttctgcctca   23100
gcctcttgag tatctgtcat tataggtgca tcccaccatg cctgacagat gtattatatt   23160
tagtgcctat ttttgcagtt tacagatgtt tttaggaaaa cttacataag aattatagat   23220
caggccaggc atggtggctc acgcctataa tccccacact tgggaggcc gaggtgggag    23280 gatcacttga ggacatgagt ttgagaccag cctggccaac atggtgaaac cctatctcta   23340
ctacaaatac aaaaattagc tggggtggt ggcaggcacc tgtaatccca gcccttcggg    23400
aagttgaggt gggagaatcg tttgaacccc agaggcagag attgcagtga gctgagatcg   23460
cgccactgca ctccagcctg ggcgacagag tcagaccctg tctaaaataa taataataat   23520
aattataggt caggggcagt ggctcacacc tataatccta gcatcttgga aggctgaggt   23580
gggaggatag cttgagctca ggagttcaag accagcctgg acaacatggt gagaccctgt   23640
ctctataaaa gattttttt ttttttgag acagagtctt gctctattgc caggctggag    23700
tgcagtggca cagtcttggc tcactgcaac cgcctcccgg gttcaagtga ttctcctgcc   23760
tcagcctcca gagtagctgg gactataggc gcctgccacc acacccagct aattttgta   23820 tttttattag acacagggtt tcaccatgtt ggccaggatg gttttttttt ttttctcttc   23880
ttgacctcgt gatccacccg ccttggcctc ccaaagtgct gggattacag acatgagcca   23940
ccgtgcccgg cctttttttt ttttattttt aattagccat gcgtagtgtt gtgtgctcgt   24000
agtcccagcc tcttgggtgg ctgaggtggg aggattgctt gagcctagga ggtcaaggct   24060
gcagtgagct atgatcaagc cactgtcctc caggttgggt gataaagtga gaccttgtct   24120
cgagaaaaaa aaaaaaaag cattgggcca ggcgcagtgg ctcacaccta aatttgacc    24180 actttgggaa gccaagacgg atggatcacc tgaggtcagg agttcaagac ctgcctggcc   24240
aacatggtga aaccctgtct atactaaaaa atacaataat taactgggca tggtggtgtg   24300
tgcctgtagt cccagctact cgggtggcta aggcacgaaa atcgcttgaa cccgggaggt   24360
gaaggttgca gtgagccgag attgtgccac tgcactacag cttgggtgac agagtgagac   24420
cctgtctcga agaaaaaaa aaaagcata aaatccatc aaaaaattat aatacattcc     24480
ttgaactatt tctcaaggtt gttaaaggta ttaaacaaga cgtactagat gctctgtaca   24540
cagggatact aataatgaga gaccttatct taccccccat caaaatagac taagtccgta   24600
caagatactg gcacaagaaa ggatcttaca ggttgtgaca attaagtaga atgatggacc   24660
ttggcccgat cctacaggtt gtgagagtta agtcaaatgg atattgggat gctcaataaa   24720
ttagcatcct tatctcccaa ctatggactt tcccgcatct tggagcaaga gcaagtaatt   24780
ctcttttctg agcctcttag cgtccccctct gagaaatagg gaaatgcaca gcctggttgt   24840
gggggctcag cgacgctccg cacagcgcct ggcacttggt acaggcgcca gtagagggcg   24900
```

```
gtgttgaggc gtctattgcg attaagacgg taggcgatga gggaagctaa gtgggtctct   24960
ctcctgcctt cccgcagctg agtgcacggt tatgggaatc cccagtatct ccaccaatct   25020
ctccggcttc ggctgcttca tggaggaaca catcgcagac ccctcagctt acggtcagcg   25080
cccaggcccc tgaggattct ggaaggggc ttgagaacag tgactcctgg atcctgggaa    25140
ggaggagctt gcacccttgg agaccagggg caccaggaaa tggggggct ctcgggccgc    25200
tgggagagga ggggtcctgg tgccacagag tcctggagac catgaagatc tccccaggat   25260
gttttctgaa cctgggtcct ggcctccaca ggtatctaca ttcttgaccg gcggttccgc   25320
agcctggatg attcctgctc gcagctcacc tccttcctct acagtttctg tcagcagagc   25380
cggcggcagc gtatcatcca gcggaaccgc acggagcgcc tctccgacct tctggactgg   25440
aaatacctag gccgggtagg acccccactt tcctatcctc tcctggcaaa tcagcagctc   25500
ctggctaggg gtctttggtg cagggtgcag ggtctcatcc tacttgtaac agttgctgtc   25560
cctttaagca atgaaccagg ccgatcgcga tggtggctca tggttgtaat cccagcactt   25620
tgggaggcct aacaggaagg atcgcatgag ctcaggagtt aagagaccag cctgggcaac   25680
attttatttt tactaaaaat aaaaaaaaat cagccgagcg tgatggtgcg tgcctgtagt   25740
cccagctact ggggaggctg aggtggtagg gtcgcttgag cccggaggt tgaggctgca     25800
gtgagccttg ttcaaaccca ctgcactcca tcctagagta acagaacaag accgtgttta   25860
aaagaaaaa aagaacattg gtcaggcgtt ctcatttgca taagggtgtg gccaaagagg     25920
agactcactt gagaattcgg cccctgtttg aggggtatgg ctcagaaact gtccattcac   25980
aggtctgctt atctacataa ggggtggagt cagatagatg gattatttgt atgggggtgca  26040
gcagtgtgct catctgcata aagggtgtgg ccaagacccc catcatctgc ctggggtgg    26100
ggcctggctc tcacatcctc tgcccctct cctcctttcc cctagtacta tatgtctgcg    26160
cgccacatgg cgctgtccaa ggcctttcca gagcacttca cctacgagcc caacgaggcg   26220
gatgcggtga gtgaccctg gatttctgct tagccaggag ctaaagggct gggcttcggt    26280
gggggtgggg tccctcctgg agtgggaagg cctagaggtg gctggatgcc tgggtgggac   26340
tgtgaggtcc tcagctcacc ctggtttgca cccacatcgc cgtatgcagg cccagggta    26400
ccgctaccca cggccagcct cggtgccacc gtcgccctcg ctgtcacgac actccagccc   26460
gcaccagagt gaggacgagg aggatccccg gaacgggccg ctggaggaag acggcgagcg   26520
ctacgatgag gacgaggagg ccgccaagga ccggcgcaac atccgtgcac cagagtggcc   26580
gcgccgagcg tcctgcacct cctccaccag cggcagcaag cgcaactctg tggacacggc   26640
cacctccagc tcactcagca ccccgagcga gcccctcagc cccaccagct ccctgggcga   26700
ggagcgtaac taagtccgcc ccaccacact ccccgcctgt cctgcctctc tgctccagag   26760
agaggatgca gaggggtgct gctcctaaac ccccgctcca gatctgcact gggtgtggcc   26820
ccgcagtgcc cccacccagt ccgccaaaca ctccaccccc tccagctcca gtttccaagt   26880
tcctgcactc cagaatccac aaagccgtgc ctttctctgg ctccagaata tgcataatca   26940
gcgccctgga gtcccctggg cctggaccgc ttcccagagg ccaggaatct gccattactc   27000
tgcggtggtg ccagagggttt taggaaacct ggcatggtgc tttcaggtct ggggcttta   27060
gagccccccg tgtggcttac aaattctaca gcatacagag caggccacgc tcaggcccgg   27120
catgcgggcc accaagttct ggaaaccacg tggtgtccct gcgaatgggg cgatcaagtc   27180
cagagccggg gcactttcag agtttgaagg taactgagag cagatggtcc tccatttcaa   27240
ctccagaagt ggggctctgg gagggatgtt ctagccctcc ctggcatgtc agagccaggc   27300
```

```
tctgcctgga ggatccctcc atccggctcc tgtcatcccc tacactttgg ccaagcaaga   27360
ggtggtagaa ccacttggct gctcattcct tctggaggac acacagtctc agtccagatg   27420
ccttcctgtc tttctggccc tttctggacc agatcctact cttcctttct aaatctgaga   27480
tctccctcca gggaatccgc ctgcagagga cagagctggc tgtcttcccc cacccctaac   27540
ctggcttatt cccaactgct ctgcccactg tgaaaccact aggttctagg tcctggcttc   27600
tagatctgga accttaccac gttactgcat actgatccct ttcccatgat ccagaactga   27660
ggtcactggg ttctagaacc cccacattta cctcgaggct cttccatccc caaactgtgc   27720
cctgccttca gctttggtga aagggagggc ccctcatgtg tgctgtgctg tgtctgcacc   27780
gcttggtttg cagttgagag gggagggcag aggggtgtg attggagtgt gtccggagat    27840
gagatgaaaa aaatacatct atatttaaga atcccaggtg tggtcagaca tgacacttgg   27900
tgggcctggc tgtgacgtcc ccccagtacc accccttccc tggtctgagc tcatcctctt   27960
attctagaga gacttggggg gtctccctat gttgcttagg ctggtctcaa cctcctgggc   28020
tcaagtgatc gtcctgcctt ggcctcccaa agtgctggga ttacaggctt gaaccaccct   28080
gccccagacc caggggaagg agaagggaa gagtcagagc tgacacagca gttttgcagc    28140
ttggacacag caagtgcttt ttaaggcctg ttttaagctt cttcagttcc catttggaga   28200
atccggccca aggtttcaca tcccatttct gtgatgaacc ctaaacccct tgtccagcat   28260
tgcttgggca tcacgtgttc ctggctgctc agctccactg gccagttcct ctcagtgtgc   28320
gcctcacatt gggatcactc aagctcgggc cataatctct taaactctgg agcaaagacc   28380
tcagtgagcc cccggttgc catgcaagtt gcatagcaat agcgtcaatg tgcccatata    28440
aagggcctaa taattccaac tgcctcccag aattgaggct ttttctttt ttgagacaga    28500 gtcttactct gttgcccaag ctggagcaca gtggcgccat ctcagctcac cgcaacttcc   28560
gtgaggcaga catgttttt gtttgagatg ggagttccac tcttttttgcc caggctggag   28620 tgcaatgacg ccatctcagc tcactgcaac ctccgcctcc cagattcaag cgattctcct   28680
acctcaacct cctgactagc tgggattaca ggtatgagcc accacaccca gctaattttg   28740
tattttagta gagacggggt ttcttcatgt tggtcaggct ggtctcgaac tcctgacatc   28800
aggtgagcga cccacctggc cccataatca ctcgttaaat agggctgttt ctggctgaga   28860
cctaacatct gtttctagat accaacctag gtcttaattc aactccctgg agtctatctc   28920
taccatctgg gagggacagt taacagccag gcaagcagag aaccctcagg ttcaacacta   28980
cccagatagc ctcttgtctt aggacagtta agaaaatggg agatggggcc aactcctctt   29040
tcactggcat cccaacccag ccagaagctt tatgagaaca gatcccacct catcttccac   29100
accacacaca aaaccaccag ctgcatcaaa aagctttatt tccatttggt ccaaggcttg   29160
ttaggatagt taagaaagct gcctattggc tggagggaga ggcttaggca gaagccctat   29220
tactttgcaa ggggcccttc agaagtcgct gggctcagaa ggctcttagt cgtgcttgag   29280
agtgagcctt tcgaagagat actcgcccag cccagcctcc gggccaccca gcctgtggag   29340
gttggtcagg tggtcaccca tcttcttgat aagcttcact tcctcatcta ggaagtgagt   29400
ctccaggaag tcagagagct gagagagaag agggagaaat tagaaaccca atccctgaa    29460 aagaggggga gagagcagcc agttgcagat taaaatgtga caggtgtgaa atgaggctct   29520
gaaggaaatt tgcccaaagg gagcagaggc ttgaggggta tggttgggta gccatggatg   29580
cagcgggtac gtacatgggg gtccgtgcgg gcagaaccca gggcatgaag atccaaaagg   29640
```

```
gcctggttca gcttttctc cagggccatg gcagctttca tggcgtctgg ggttttaccc    29700
cactcatctt cagctggctt ctatatagaa gggagaaatg gctcagaata cacacactcg    29760
gcacatagaa ctaaacctac atttcccaag agtcgttggg ggtcagaggc ccaggccaca    29820
aagacatgtg acagcttgta tttatcactc tccgcaccct gtcctagctc ttacagctat    29880
acgtccctaa gaccacgcag cggtgtggac tgccgcgtgt tgtgggcact gcacgaggtg    29940
cgcctctatt tccagcggtt aagagggctc acaagaccga actcaatctc ccagaagccc    30000
acgcgacacc tacgccctca aatcaaggct cctcgcgcgc acggcctgct gggagatgta    30060
gtccattacc cacacactag ttaccttgat gtcctggaag agagcgcggc cgccacgctg    30120
gttttgcatc ttcaggagac gctcgtagcc ctcgcgcttc tcctcggcca attcgcggaa    30180
gaagtggctc acgccttcca gagccacatc atcgcggtcg aaatagaagc cctacggaaa    30240
gagatggagg caacaatggt tagcgggagg cgaggccaag gggactccgc cctctgttta    30300
cccgaccgca caagaaggc tggcgcgtgc agtgagggcc ggaggtgcgc agctggagga    30360
aattagggcc aggggcgtcc tggggactca ccagagagag gtaggtgtag gaggcctgca    30420
ggtacaaatt gaccaggctg ttgacggctg cctccacgtc ggtggaataa ttctgacgaa    30480
tctgggagct catggttggt tggcaagaag gagctaacca caaaaacggt gctggcaggt    30540
cccagaagca ggagatggcc gagaagatgg tcccggaggt tgcaagcgga gaggaaatcg    30600
gagggcggtc ggaggctgga agagagtccc cggatctgtt ccgtccaaac actgttgaag    30660
caagagacag acccgcggga ccgccgaact gcgaggggac gtggctaggg cggcttcttt    30720
tatggtgcgc cggcccctcgg aggcaggcg ctcggggagg gctagcggcc aatctgcggt    30780
ggcaggaggc ggggccgaag gccgtgcctg accaatccgg agcacatagg agtctcagcc    30840
ccccgcccca aagcaagggg aagtcacgcg cctgtagcgc cagcgtgttg tgaaatgggg    30900
gcttgggggg gttggggccc tggggctgat tctggaaatg caggggttcg tgggcgggag    30960
ggtgggggct ggggtccctc tgggaggcta gagttttatg                         31000
```

<210> SEQ ID NO 7
<211> LENGTH: 22
<212> TYPE: DNA
<213> ORGANISM: Artificial sequence
<220> FEATURE:
<223> OTHER INFORMATION: Primer

<400> SEQUENCE: 7
tgatgaagag agccatcttt gc                                              22

<210> SEQ ID NO 8
<211> LENGTH: 21
<212> TYPE: DNA
<213> ORGANISM: Artificial sequence
<220> FEATURE:
<223> OTHER INFORMATION: Primer

<400> SEQUENCE: 8
aggagtcgtc cagcatgttg t                                               21

<210> SEQ ID NO 9
<211> LENGTH: 24
<212> TYPE: DNA
<213> ORGANISM: Artificial sequence
<220> FEATURE:
<223> OTHER INFORMATION: Probe

<400> SEQUENCE: 9
actcagcggc agtctttccc acca                                            24

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
ccgactcagg tagggtgagc                                                 20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
cttggtgacc ggtagagtta                                                 20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
gagaggcatg gctactgcgg                                                 20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
cggctgagag gcatggctac                                                 20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
tcttccaatc ctggaagcga                                                 20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
atggtcccac cagatagtag                                                 20

<210> SEQ ID NO 16
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 16
cgtgtatggt cccaccagat                                                   20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
aggtgttgag cctcgattgc                                                   20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
tgactgtatt ggctgtgtcc                                                   20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
ctccttgact gtattggctg                                                   20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
gtagagcttc ctcccaaatt                                                   20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
cctccgatcc agaatgtaaa                                                   20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
acttccaatc tagcaagtcc                                                   20
```

-continued

```
<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
tcccgtggct cttcctcatc                                               20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
tgtggaggag gaacaggagg                                               20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
tgccacctgt ggaggaggaa                                               20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
ctggagggcc cagtgtccac                                               20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
gtgagctgga gggcccagtg                                               20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
cataggccct ctgcgagagg                                               20

<210> SEQ ID NO 29
<211> LENGTH: 20
<212> TYPE: DNA
<213> ORGANISM: Artificial sequence
<220> FEATURE:
```

<223> OTHER INFORMATION: Synthetic oligonucleotide

<400> SEQUENCE: 29
atctgcatag gccctctgcg					20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
ttcaggcacc ctcccatctg					20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
actcaagagt ctggagtggg					20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
ggctggagtg tctgaaacag					20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
tggagctcaa gggctggagt					20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
ccaagaaagg cacggcggcg					20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
ctggagactc cagatcagtg					20

```
<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
aaacaatggc agatgcctgg                                                    20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
cctaaaacct ctggcattga                                                    20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
cctggaagcc aataaaccag                                                    20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
gccacagcct ggaagccaat                                                    20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
gccacacaga atccaacatg                                                    20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
tcgggaagcc acacagaatc                                                    20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 42
cctgaaatgt cctaactctg                                              20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
ttaatccctg aaatgtccta                                              20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
aatctgtcga cagagctact                                              20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
gacaagcaat ctgtcgacag                                              20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
tgtgtatcac cgcaccaggt                                              20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
gaaatggagg accgtgagca                                              20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
tgctcctttg aagaacacac                                              20

<210> SEQ ID NO 49
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 49
gcagaaaggt gtctggtcca                                              20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
aaggcagaaa ggtgtctggt                                              20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
tgacagacat tctgccctca                                              20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
agtgggctga gcacttgtgg                                              20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
agccactggg acccagaacc                                              20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
ttcaagaagc cggtgggctc                                              20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
```
gcagaaaggc ctcgaggtac                                               20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56 cccccccaggg cctaggacgc                                              20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
acagcattga gtctgccatc                                               20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
tggcctgact ggatgctgga                                               20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
attgatctaa ctctgtccca                                               20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
atccttggat taaaagagtg                                               20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
gaccaaaact cccagatttc                                               20

<210> SEQ ID NO 62
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 62
agccacatgt agggaccaca                                                 20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
catgcttcat ttctttattg                                                 20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
ggcccatgct tcatttcttt                                                 20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
tcagagatag ccagagagag                                                 20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
ccctactgtc tcatgactta                                                 20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
gaggcctcag caaatgccag                                                 20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
cctccagcaa tgtattttaa                                                 20
```

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
aggaatcaga gggttctgtg                                                   20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
agccctctct tttatgacaa                                                   20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
acaagctaaa gacttaaact                                                   20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
gatttgcaag tgactctcaa                                                   20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
tggattccct ctgtagatca                                                   20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
tgtctctagc tctgacaaca                                                   20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 75
ccagatgcta tttctagatt                                                    20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
actgctggag tccccagcaa                                                    20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
cctataggac tatccaggaa                                                    20
```

MODULATION OF GYS1 EXPRESSION

SEQUENCE LISTING

The present application is being filed along with a Sequence Listing in electronic format. The Sequence Listing is provided as a file entitled BIOL0294USASEQ_ST25.txt, created on Dec. 3, 2018 which is 108 KB in size. The information in the electronic format of the sequence listing is incorporated herein by reference in its entirety.

FIELD OF THE INVENTION

Provided herein are methods, compounds, and compositions useful for reducing expression of glycogen synthase 1 (hereinafter referred to as GYS1) in an animal. Also, provided herein are methods, compounds, and compositions comprising GYS1 inhibitors, which can be useful in reducing GYS1-related diseases or conditions in an animal. Such methods, compounds, and compositions can be useful, for example, to treat, prevent, delay or ameliorate a glycogen storage disease or a polyglucosan disorder in an animal.

BACKGROUND

Glycogen is a branched polymer of glucose that constitutes the sole carbohydrate reserve for mammals. It is synthesized by glycogen synthase (GYS), the only mammalian enzyme able to polymerize glucose (Bollen M. et al. Biochem. J. 1998 336: 19-31). Glycogen biosynthesis involves chain elongation by glycogen synthase and chain branching by glycogen branching enzyme. If chain elongation outbalances chain branching, glycogen forms starch-like precipitates made up of long, non-branched chains called polyglucosans. The most glycogenic tissues are muscle and liver.

Glycogen synthase 1 (GYS1) is an enzyme involved in converting glucose to glycogen by catalyzing the elongation of short glucose polymers into long glycogen polymers. Mutations in GYS1 are associated with glycogen storage diseases. In the brain, glycogen is normally stored in astrocytes (brown A. M. J. Neurochem. 89: 537-552, 2004) and glycogen synthesis is normally absent in neurons because of tight regulation of GYS1 by laforin and malin (Vilchez et al., Nat. Neurosci. 10: 1407-1413, 2007). Nevertheless, aberrant glycogen accumulation in neurons is a hallmark of patients suffering from Lafora disease, Pompe disease, Andersen's disease, adult polyglucosan disease, or other polyglucosan disorders.

Currently, there is a lack of acceptable options for treating glycogen storage diseases. There is also a lack of specific inhibitors for glycogen synthase. It is therefore an object herein to provide methods for the treatment of such diseases.

SUMMARY

Provided herein are compositions, compounds and methods for modulating expression of GYS1-associated diseases such as glycogen storage disease and polyglucosan disorders, including Lafora disease, adult polyglucosan body disease, Andersen's disease, and Pompe disease. In certain embodiments, these compositions, compounds and methods are for modulating the expression of GYS1. In certain embodiments, the GYS1 modulator is a GYS1-specific inhibitor. In certain embodiments, the GYS1-specific inhibitor decreases expression or activity of GYS1. In certain embodiments, GYS1-specific inhibitors include nucleic acids, proteins and small molecules. In certain embodiments, the GYS1-specific inhibitor is a nucleic acid. In certain embodiments, GYS1-specific inhibitor comprises a modified oligonucleotide. In certain embodiments, the modified oligonucleotide can be single stranded or double stranded.

Certain embodiments are directed to novel GYS1 inhibitors useful for inhibiting GYS1, which can be useful for preventing, inhibiting, or slowing the progression of accumulation of glycogen in tissues. Certain embodiments are directed to GYS1 inhibitors useful for treating, ameliorating, or slowing progression of polyglucosan disorders, including, but not limited to, Lafora disease, adult polyglucosan body disease, and Pompe disease. Certain embodiments relate to the novel findings of antisense inhibition of GYS1 resulting in reduction of glycogen synthesis, glycogen aggregation, reduction of Lafora bodies accumulation, reduction of polyglucosan bodies, glycogen level normalization, reduction or cessation of seizures, improvement or prevention of cognivitive deterioration, reduction of neuromuscular weakness, and reduction or cessation of epileptic episodes. Certain embodiments are directed to GYS1 inhibitors useful in improving glycogen levels. Certain embodiments are directed to GYS1 inhibitors useful in reducing incidence of seizures or epileptic episodes.

DETAILED DESCRIPTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Compounds described by ISIS number (ISIS #) indicate a combination of nucleobase sequence, chemical modification, and motif.

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE and 2'-O(CH$_2$)$_2$—OCH$_3$) refers to an O-methoxy-ethyl modification at the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"3' target site" refers to the nucleotide of a target nucleic acid which is complementary to the 3'-most nucleotide of a particular compound.

"5' target site" refers to the nucleotide of a target nucleic acid which is complementary to the 5'-most nucleotide of a particular compound.

"5-methylcytosine" means a cytosine with a methyl group attached to the 5 position.

"About" means within ±10% of a value. For example, if it is stated, "the compounds affected about 70% inhibition of a GYS1", it is implied that GYS1 levels are inhibited within a range of 60% and 80%.

"Administration" or "administering" refers to routes of introducing a compound or composition provided herein to an individual to perform its intended function. An example of a route of administration that can be used includes, but is not limited to parenteral administration, such as subcutaneous, intravenous, or intramuscular injection or infusion.

"Administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel or sequentially.

"Adult polyglucosan body disease" is characterized by dysfunction of the central and peripheral nervous systems. Associated symptoms and findings may include sensory loss in the legs, progressive muscle weakness of the arms and legs, gait disturbances, urination difficulties, and/or cognitive impairment or dementia.

"Amelioration" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Andersen's disease", also known as glycogen storage disease type IV, is caused by deficient activity of the glycogen-branching enzyme, resulting in accumulation of abnormal glycogen in the liver, muscle, and other tissues. The disease course is typically characterized by progressive liver cirrhosis and liver failure. In some case, several neuromuscular variants of Andersen's disease occur that may be evident at birth, late childhood, or adulthood.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable and/or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an oligonucleotide and optionally one or more additional features, such as a conjugate group or terminal group. Examples of antisense compounds include single-stranded and double-stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"Ataxia" means the loss of full control of bodily movements.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Chemical modification" in a compound describes the substitutions or changes through chemical reaction, of any of the units in the compound. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine ($^m$C) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Dementia" means a continued loss of intellectual function that impairs memory, judgment, and thought.

"Designing" or "Designed to" refer to the process of designing a compound that specifically hybridizes with a selected nucleic acid molecule.

"Diluent" means an ingredient in a composition that lacks pharmacological activity, but is pharmaceutically necessary or desirable. For example, the diluent in an injected composition can be a liquid, e.g. saline solution.

"Differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides.

Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Dose" means a specified quantity of a compound or pharmaceutical agent provided in a single administration, or in a specified time period. In certain embodiments, a dose may be administered in two or more boluses, tablets, or injections. For example, in certain embodiments, where subcutaneous administration is desired, the desired dose may require a volume not easily accommodated by a single injection. In such embodiments, two or more injections may be used to achieve the desired dose. In certain embodiments, a dose may be administered in two or more injections to minimize injection site reaction in an individual. In other embodiments, the compound or pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Double-stranded compound" means a compound comprising two oligomeric compounds that are complementary to each other and form a duplex, and wherein one of the two said oligomeric compounds comprises an oligonucleotide.

"Effective amount" means the amount of compound sufficient to effectuate a desired physiological outcome in an individual in need of the compound. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Ensembl ID' is an identification number consisting of letters and numbers assigned to a gene sequence by Ensembl, which is a joint project between EMBL-EBI and the Welcome Trust Sanger Institute to develop a software system that produces and maintains automatic annotation of selected eukaryotic genomes. Ensembl annotation helps identify a gene location in a particular genome and can be used to configure the equivalent gene on another species' genome.

"Epilepsy" is a central nervous system disorder in which nerve cell activity in the brain becomes chronically disrupted. In certain instances, it may cause seizures, periods of unusual behavior, sensations, and sometimes loss of consciousness. In certain instances, it may also cause other symptoms including myoclonus, cognitive deficits, learning disabilities, or developmental delay in children. In certain instances, it may lead to death in some patients. In certain instances, some forms of epilepsy are associated with progressive neurodegenerative diseases. Many people with epilepsy have more than one symptom.

"Expression" includes all the functions by which a gene's coded information is converted into structures present and operating in a cell. Such structures include, but are not limited to the products of transcription and translation.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Glycogen" is a polysaccharide that is the principal storage form of glucose in animals. Glycogen is found in the form of granules in the cytosol in a variety of tissues, including brain.

"GYS1" means glycogen synthase 1 and refers to any nucleic acid of GYS1. For example, in certain embodiments, GYS1 includes a DNA sequence encoding GYS1, an RNA sequence transcribed from DNA encoding GYS1 (including genomic DNA comprising introns and exons). The target may be referred to in either upper or lower case.

"GYS1-specific inhibitor" refers to any agent capable of specifically inhibiting GYS1 expression or activity at the molecular level. For example, GYS1-specific inhibitors include nucleic acids (including antisense compounds), peptides, antibodies, small molecules, and other agents capable of inhibiting the expression or activity of GYS1.

"Hybridization" means annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

"Immediately adjacent" means there are no intervening elements between the immediately adjacent elements of the same kind (e.g. no intervening nucleobases between the immediately adjacent nucleobases).

"Individual" means a human or non-human animal selected for treatment or therapy.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage. Non-phosphate linkages are referred to herein as modified internucleoside linkages.

"Intraperitoneal administration" means administration through infusion or injection into the peritoneum.

"Intravenous administration" means administration into a vein.

"Lafora bodies" are massive neurotoxic inclusions formed as a result of mis-structuring of glycogen and its precipitation and accumulation to form polyglucosan.

"Lafora disease" (LD) means the severe and fatal form of adolescence-onset epilepsy resulting from accumulation of Lafora bodies in neurons, muscle, and other tissues.

"Lengthened oligonucleotides" are those that have one or more additional nucleosides relative to an oligonucleotide disclosed herein, e.g. a parent oligonucleotide.

"Linked nucleosides" means adjacent nucleosides linked together by an internucleoside linkage.

"Mismatch" or "non-complementary" means a nucleobase of a first oligonucleotide that is not complementary to the corresponding nucleobase of a second oligonucleotide or target nucleic acid when the first and second oligonucleotides are aligned. For example, nucleobases including but not limited to a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modulating" refers to changing or adjusting a feature in a cell, tissue, organ or organism. For example, modulating GYS1 can mean to increase or decrease the level of GYS1 in a cell, tissue, organ or organism. A "modulator" effects the change in the cell, tissue, organ or organism. For example, a compound can be a modulator of GYS1 that decreases the amount of GYS1 in a cell, tissue, organ or organism.

"MOE" means methoxyethyl.

"Monomer" refers to a single unit of an oligomer. Monomers include, but are not limited to, nucleosides and nucleotides.

"Motif" means the pattern of unmodified and/or modified sugar moieties, nucleobases, and/or internucleoside linkages, in an oligonucleotide.

"Myoclonus" means episodes of repeated, stereotypic, involuntary muscle jerking or twitching that can affect part of the body or the entire body for variable durations.

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Oligomeric compound" means a compound comprising a single oligonucleotide and optionally one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified. "Unmodified oligonucleotide" means an oligonucleotide that does not comprise any sugar, nucleobase, or internucleoside modification.

"Parent oligonucleotide" means an oligonucleotide whose sequence is used as the basis of design for more oligonucleotides of similar sequence but with different lengths, motifs, and/or chemistries. The newly designed oligonucleotides may have the same or overlapping sequence as the parent oligonucleotide.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutically acceptable carrier or diluent" means any substance suitable for use in administering to an animal. For example, a pharmaceutically acceptable carrier can be a sterile aqueous solution, such as PBS or water-for-injection.

"Pharmaceutically acceptable salts" means physiologically and pharmaceutically acceptable salts of compounds, such as oligomeric compounds or oligonucleotides, i.e., salts that retain the desired biological activity of the parent compound and do not impart undesired toxicological effects thereto.

"Pharmaceutical agent" means a compound that provides a therapeutic benefit when administered to an individual.

"Pharmaceutical composition" means a mixture of substances suitable for administering to an individual. For example, a pharmaceutical composition may comprise one or more compounds or salt thereof and a sterile aqueous solution.

"Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Pompe disease" also called glycogen storage disease type II, is a neuromuscular disorder caused by buildup of glycogen in the body's cells. Pompe disease is a single disease continuum with variable rates of disease progression and different ages of onset. The first symptoms can occur at any age from birth to late adulthood.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Prevent" refers to delaying or forestalling the onset, development or progression of a disease, disorder, or condition for a period of time from minutes to indefinitely.

"Prodrug" means a compound in a form outside the body which, when administered to an individual, is metabolized to another form within the body or cells thereof. In certain embodiments, the metabolized form is the active, or more active, form of the compound (e.g., drug). Typically conversion of a prodrug within the body is facilitated by the action of an enzyme(s) (e.g., endogenous or viral enzyme) or chemical(s) present in cells or tissues, and/or by physiologic conditions.

"Reduce" means to bring down to a smaller extent, size, amount, or number.

"RefSeq No." is a unique combination of letters and numbers assigned to a sequence to indicate the sequence is for a particular target transcript (e.g., target gene). Such sequence and information about the target gene (collectively, the gene record) can be found in a genetic sequence database. Genetic sequence databases include the NCBI Reference Sequence database, GenBank, the European Nucleotide Archive, and the DNA Data Bank of Japan (the latter three forming the International Nucleotide Sequence Database Collaboration or INSDC).

"Region" is defined as a portion of the target nucleic acid having at least one identifiable structure, function, or characteristic.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double-stranded siRNA, single-stranded RNA (ssRNA), and microRNA, including microRNA mimics.

"Segments" are defined as smaller or sub-portions of regions within a nucleic acid.

"Seizures" are a symptom of many different disorders and conditions that can affect the brain. "Seizures" are typically caused by disruptions in the electric communication between neurons in the brain, resulting from a brain injury or a disease or disorder. Seizures can take on different forms and affect different people in different ways. Common physical changes that may occur during a seizure are difficulty talking, inability to swallow, drooling, repeated blinking of the eyes, staring, lack of movement of muscle tone, slumping tremors, twitching, or jerking movements, rigid or tense muscles, repeated non-purposeful movements, called automatisms, involving the face, arms, or legs, convulsions, loss of control of urine or stool, sweating, change in skin color (paleness or flushing), dilation of pupils, biting of tongue, difficulty breathing, heart palpitations. In some embodiments, seizures are mild. In other embodiments, seizures are completely disabling or may result in death. Abnormal brain activity can often be documented by abnormal findings on an electroencephalogram (EEG).

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded" in reference to a compound means the compound has only one oligonucleotide. "Self-complementary" means an oligonucleotide that at least partially hybridizes to itself. A compound consisting of one oligonucleotide, wherein the oligonucleotide of the compound is self-complementary, is a single-stranded compound. A single-stranded compound may be capable of binding to a complementary compound to form a duplex.

"Sites," are defined as unique nucleobase positions within a target nucleic acid.

"Specifically hybridizable" refers to an oligonucleotide having a sufficient degree of complementarity between the oligonucleotide and a target nucleic acid to induce a desired effect, while exhibiting minimal or no effects on non-target nucleic acids. In certain embodiments, specific hybridization occurs under physiological conditions.

"Specifically inhibit" a target nucleic acid means to reduce or block expression of the target nucleic acid while exhibiting fewer, minimal, or no effects on non-target nucleic acids reduction and does not necessarily indicate a total elimination of the target nucleic acid's expression.

"Standard cell assay" means assay(s) described in the Examples and reasonable variations thereof.

"Standard in vivo experiment" means the procedure(s) described in the Example(s) and reasonable variations thereof.

"Sugar moiety" means an unmodified sugar moiety or a modified sugar moiety. "Unmodified sugar moiety" or "unmodified sugar" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. "Modified sugar moiety" or "modified sugar" means a modified furanosyl sugar moiety or a sugar surrogate. "Modified furanosyl sugar moiety" means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars.

"Sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

"Subcutaneous administration" means administration just below the skin.

"Target gene" refers to a gene encoding a target.

"Targeting" means specific hybridization of a compound that to a target nucleic acid in order to induce a desired effect.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"Target segment" means the sequence of nucleotides of a target nucleic acid to which a compound described herein is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

"Therapeutically effective amount" means an amount of a compound, pharmaceutical agent, or composition that provides a therapeutic benefit to an individual.

"Treat" refers to administering a compound or pharmaceutical composition to an animal in order to effect an alteration or improvement of a disease, disorder, or condition in the animal.

Certain Embodiments

Certain embodiments provide methods, compounds, and compositions for modulating a glycogen storage disease or a polyglucosan disorder or a symptom thereof, in an individual by administering the compound or composition to the individual, wherein the compound or composition comprises a GYS1 modulator. Modulation of GYS1 can lead to a decrease of GYS1 level or expression in order to reduce glycogen synthesis and aggregation in order to treat, prevent, ameliorate or delay a glycogen storage disease, or a symptom thereof. In certain embodiments, the GYS1 modulator is a GYS1-specific inhibitor. In certain embodiments, GYS1-specific inhibitors are nucleic acids (including antisense compounds), peptides, antibodies, small molecules, and other agents capable of inhibiting the expression or activity of GYS1. In certain embodiments, the individual is human.

Certain embodiments disclosed herein provide compounds or compositions comprising a GYS1 modulator. Such compounds or compositions are useful to treat, prevent, ameliorate, or delay the onset of a glycogen storage disease, or a symptom thereof. In certain embodiments, the compound comprises a GYS1-specific inhibitor. In certain embodiments, the GYS1-specific inhibitor is a nucleic acid, polypeptide, antibody, small molecules, or other agent capable of inhibiting the expression or activity of GYS1. In certain embodiments, a GYS1-specific inhibitor is a nucleic acid targeting GYS1. In certain embodiments, the nucleic acid is single stranded. In certain embodiments, the nucleic acid is double stranded. In certain embodiments, the compound or composition comprises an antisense compound. In any of the foregoing embodiments, the compound or composition comprises an oligomeric compound. In certain embodiments, the compound or composition comprises an oligonucleotide targeting GYS1. In certain embodiments, the oligonucleotide is single stranded. In certain embodiments, the compound comprises deoxyribonucleotides. In certain embodiments, the compound comprises ribonucleotides and is double-stranded. In certain embodiments, the oligonucleotide is a modified oligonucleotide. In certain embodiments, the modified oligonucleotide is single stranded.

In any of the foregoing embodiments, the compound can comprise a modified oligonucleotide 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides in length.

In certain embodiments, at least one internucleoside linkage of said modified oligonucleotide is a modified internucleoside linkage. In certain embodiments, at least one internucleoside linkage is a phosphorothioate internucleoside linkage. In certain embodiments, the internucleoside linkages are phosphorothioate linkages and phosphate ester linkages.

In certain embodiments, any of the foregoing oligonucleotides comprises at least one modified sugar. In certain embodiments, at least one modified sugar comprises a 2'-O-methoxyethyl group. In certain embodiments, at least one modified sugar is a bicyclic sugar, such as a 4'-CH(CH$_3$)—O-2' group, a 4'-CH$_2$—O-2' group, or a 4'-(CH$_2$)$_2$—O-2' group.

In certain embodiments, at least one nucleoside of said modified oligonucleotide comprises a modified nucleobase. In certain embodiments, the modified nucleobase is a 5-methylcytosine.

In certain embodiments, a compound or composition comprises a modified oligonucleotide comprising: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar. In certain embodiments, at least one internucleoside linkage is a phosphorothioate linkage. In certain embodiments, and at least one cytosine is a 5-methylcytosine.

In certain embodiments, a compound comprises a modified oligonucleotide 12 to 80 linked nucleosides in length and having a nucleobase sequence comprising the nucleobase sequence of any one of SEQ ID Nos: 10-76. In certain embodiments, the compound is an antisense compound or oligomeric compound. In certain embodiments, the compound is single-stranded. In certain embodiments, the compound is double-stranded. In certain embodiments, the modified oligonucleotide is 12 to 30 linked nucleosides in length.

In certain embodiments, the compounds or compositions disclosed herein further comprise a pharmaceutically acceptable carrier or diluent.

In certain embodiments, the compound or composition is co-administered with a second agent. In certain embodiments, the compound and the second agent are administered concomitantly.

In certain embodiments, compounds and compositions described herein targeting GYS1 can be used in methods of inhibiting expression of GYS1 in a cell. In certain embodiments, compounds and compositions described herein targeting GYS1 can be used in methods of treating, preventing, delaying, or ameliorating a glycogen storage disease or a polyglucosan disorder, including, but not limited to, Lafora disease, adult polyglucosan body disease, and Pompe disease.

Certain Indications

Certain embodiments provided herein relate to methods of inhibiting GYS1 expression or activity, which can be useful for treating, preventing, or ameliorating a disease associated with GYS1 in an individual, by administration of a compound or composition that targets GYS1. In certain embodiments, such a compound or composition comprises a GYS1-specific inhibitor. In certain embodiments, the compound comprises an antisense compound or an oligomeric compound targeted to GYS1. In certain embodiments, the compound comprises a modified oligonucleotide targeted to GYS1.

In certain embodiments, a method of inhibiting expression or activity of GYS1 in a cell comprises contacting the cell with a compound or composition comprising a GYS1-specific inhibitor, thereby inhibiting the expression or activity of GYS1 in the cell. In certain embodiments, the cell is a neuron. In certain embodiments, the cell is a hepatocyte. In certain embodiments, the cell is a skeletal muscle cell. In certain embodiments, the cell is a cardiac muscle cell. In certain embodiments, the cell is in the brain tissue, in the liver, in the heart, or in the skeletal muscle. In certain embodiments, the cell is in the brain, liver, heart, or skeletal muscle tissue of an individual who has, or is at risk of having a disease, disorder, condition, symptom, or physiological marker associated with a glycogen storage disease or a polyglucosan disorder. In certain embodiments, the polyglucosan disease or disorder is Lafora disease. In certain embodiments, the polyglucosan disease or disorder is adult polyglucosan body disease. In certain embodiments, the disease or disorder is Andersen's disease. In certain embodiments, the polyglucosan disease or disorder is Pompe disease. In certain embodiments, the GYS1-specific inhibitor is a nucleic acid, peptide, antibody, small molecule or other agent capable of inhibiting the expression or activity of the GYS1. In certain embodiments, the GYS1-specific inhibitor is an antisense compound or an oligomeric compound targeted to GYS1. In certain embodiments, the GYS1-specific inhibitor is oligonucleotide targeted to GYS1. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded.

In certain embodiments, a method of treating, preventing, delaying the onset, slowing the progression, or ameliorating one or more disease, disorders, conditions, symptoms, or physiological markers associated with GYS1 comprises administering to the individual a compound or composition comprising a GYS1-specific inhibitor. In certain embodiments, a method of treating, preventing, delaying the onset, slowing the progression, or ameliorating a disease, disorder, condition, symptom, or physiological marker associated with a with a glycogen storage disease or a polyglucosan disease or disorder in an individual comprises administering to the individual a compound or composition comprising a GYS1-specific inhibitor, thereby treating, preventing, delaying the onset, slowing the progression, or ameliorating the disease. In certain embodiments, the individual is identified as having, or at risk of having, the disease, disorder, condition, symptom or physiological marker. In certain embodiments, the polyglucosan disease or disorder is Lafora disease. In certain embodiments, the polyglucosan disease or disorder is adult polyglucosan body disease. In certain embodiments, the disease or disorder is Andersen's disease. In certain embodiments, the polyglucosan disease or disorder is Pompe disease. In certain embodiments, the GYS1-specific inhibitor is administered to the individual parenterally. In certain embodiments, the parenteral administration is intracerebroventricular administration. In certain embodiments, the parenteral administration is intrathecal administration. In certain embodiments, the parenteral administration is subcutaneous administration. In certain embodiments, the individual is human. In certain embodiments, the GYS1-specific inhibitor is a nucleic acid, peptide, antibody, small molecule or other agent capable of inhibiting the expression or activity of GYS1. In certain embodiments, the GYS1-specific inhibitor comprises an antisense compound or an oligomeric compound targeted to GYS1. In certain embodiments, the GYS1-specific inhibitor is an oligonucleotide targeted to GYS1. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded.

In certain embodiments, a method of reducing seizures, decreasing myoclonus or muscle spasms, alleviating difficulty in walking (peripheral neuropathy), spasticity, reducing, preventing the onset of, or treating dementia, alleviating difficulties in speech, reducing or preventing the onset of visual hallucinations, treating, reducing or preventing the onset of progressive neurologic degeneration, treating, reducing, or preventing the onset of damage to nerves that control bladder function, lessening hypotonia, improving muscle tone, reducing or preventing the onset of an enlarged liver, reducing or preventing the onset of heart defects, reducing or preventing the accumulation of polyglucosan bodies in a cell. reducing or preventing the accumulation of lafora bodies in a cell, reducing glycogen accumulation in a cell, improving or preventing cognitive deterioration, and reducing ataxia, or a combination thereof, in an individual comprises administering to the individual a compound or composition comprising a GYS1-specific inhibitor. In certain embodiments, the cell is a neuron. In certain embodiments, the cell is a hepatocyte. In certain embodiments, the cell is a skeletal muscle cell. In certain embodiments, the cell is a cardiac muscle cell. In certain embodiments, administering the compound or composition reduces seizures in the individual. In certain embodiments, administering the compound or composition decreases myoclonus or muscle spasms in the individual. In certain embodiments, administering the compound or composition alleviates difficulty in walking in the individual. In certain embodiments, administering the compound or composition alleviates peripheral neuropathy in the individual. In certain embodiments, administering the compound or composition alleviates spasticity in the individual. In certain embodiments, administering the compound or composition reduces, prevents the onset of, or treats dementia in the individual. In certain embodiments, administering the compound or composition alleviates difficulties in speech in the individual. In certain embodiments, administering the compound or composition reduces or prevents the onset of visual hallucinations in the individual. In certain embodiments, administering the compound or composition treats, reduces or prevents the onset of progressive neurologic degeneration in the individual. In certain embodiments, administering the compound or composition treats, reduces or prevents the onset of damage to the nerves that control bladder function in the individual. In certain embodiments, administering the compound or composition treats, reduces or prevents the onset of hypotonia in the individual. In certain embodiments, administering the compound or composition improves muscle tone in the individual. In certain embodiments, administering the compound or composition treats, reduces or prevents the onset of liver enlargement in the individual. In certain embodiments, administering the compound or composition treats, reduces or prevents the onset of heart defects in the individual. In certain embodiments, administering the compound or composition treats, reduces or prevents the onset of polyglucosan bodies in a cell in the individual. In certain embodiments, administering the compound or composition treats, reduces or prevents the onset of lafora bodies in a cell in the individual. In certain embodiments, administering the compound or composition treats, reduces or prevents the onset of glycogen accumulation in a cell in the individual. In certain embodiments, the cell is a neuron. In certain embodiments, the cell is a hepatocyte. In certain embodiments, the cell is a skeletal muscle cell. In certain embodiments, the cell is a cardiac muscle cell. In certain embodiments, administering the compound or composition improves or prevents cognitive deterioration. In certain embodiments, administering the compound or composition treats, reduces ataxia in the individual. In certain embodiments, the individual is identified as having, or at risk of having a disease, disorder, condition, symptom, or physiological marker associated with a glycogen storage disease or a polyglucosan disease or disorder. In certain embodiments, the polyglucosan disease or disorder is Lafora disease. In certain embodiments, the polyglucosan disease or disorder is adult polyglucosan body disease. In certain embodiments, the disease or disorder is Andersen's disease. In certain embodiments, the polyglucosan disease or disorder is Pompe disease. In certain embodiments, the GYS1-specific inhibitor is administered to the individual parenterally. In certain embodiments, the parenteral administration is intracerebroventricular administration. In certain embodiments, the parenteral administration is intrathecal administration. In certain embodiments, the parenteral administration is subcutaneous administration. In certain embodiments, the individual is human. In certain embodiments, the GYS1-specific inhibitor is a nucleic acid, peptide, antibody, small molecule or other agent capable of inhibiting the expression or activity of the GYS1. In certain embodiments, the GYS1-specific inhibitor is an antisense compound or an oligomeric compound targeted to GYS1. In certain embodiments, the GYS1-specific inhibitor is oligonucleotide targeted to GYS1. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded.

In certain embodiments, administering the compound or composition disclosed herein decreases seizures, decreases myoclonus or muscle spasms, alleviates difficulty in walking, alleviates spasticity, reduces, prevents the onset of or treats dementia, alleviates difficulties in speech, reduces or prevents the onset of visual hallucinations, treats, reduces or prevents the onset of progressive neurologic degeneration, treating, reducing, or preventing the onset of damage to nerves that control bladder function, lessening hypotonia, improving muscle tone, reducing or preventing the onset of an enlarged liver, reducing or preventing the onset of heart defects, reduces polyglucosan bodies in a cell, reduces lafora bodies in a cell, reduces glycogen accumulation in a cell, improves cognitive deterioration, and reduces ataxia, or a combination thereof. In certain embodiments, seizures were independently reduced by at least 5%, at least 10%, at least 20%, at least 30%, at least 35%, at least 40%, at least 45% or at least 50%. In certain embodiments, myoclonus or muscle spasms were independently reduced by at least 5%, at least 10%, at least 20%, at least 30%, at least 35%, at least 40%, at least 45% or at least 50%. In certain embodiments, difficulty in walking was independently alleviated by at least 5%, at least 10%, at least 20%, at least 30%, at least 35%, at least 40%, at least 45% or at least 50%. In certain embodiments, spasticity was independently reduced by at least 5%, at least 10%, at least 20%, at least 30%, at least 35%, at least 40%, at least 45% or at least 50%. In certain embodiments, difficulty in speech was independently alleviated by at least 5%, at least 10%, at least 20%, at least 30%, at least 35%, at least 40%, at least 45% or at least 50%. In certain embodiments, visual hallucinations were independently reduced by at least 5%, at least 10%, at least 20%, at least 30%, at least 35%, at least 40%, at least 45% or at least 50%. In certain embodiments, progressive neurologic degeneration was independently reduced by at least 5%, at least 10%, at least 20%, at least 30%, at least 35%, at least 40%, at least 45% or at least 50%. In certain embodiments, dementia progression was independently reduced by at least 5%, at least 10%, at least 20%, at least 30%, at least 35%, at least 40%, at least 45% or at least 50%. In certain embodiments, nerve damage of bladder function independently reduced by at least 5%, at least 10%, at least 20%, at least 30%, at least 35%, at least 40%, at least 45% or at least 50%. In certain embodiments, hypotonia was independently reduced by at least 5%, at least 10%, at least 20%, at least 30%, at least 35%, at least 40%, at least 45% or at least 50%. In certain embodiments, liver enlargement was independently reduced by at least 5%, at least 10%, at least 20%, at least 30%, at least 35%, at least 40%, at least 45% or at least 50%. In certain embodiments, heart defects were independently reduced by at least 5%, at least 10%, at least 20%, at least 30%, at least 35%, at least 40%, at least 45% or at least 50%. In certain embodiments, polyglucosan bodies in a cell were independently reduced by at least 5%, at least 10%, at least 20%, at least 30%, at least 35%, at least 40%, at least 45% or at least 50%. In certain embodiments, lafora bodies in a cell were independently reduced by at least 5%, at least 10%, at least 20%, at least 30%, at least 35%, at least 40%, at least 45% or at least 50%. In certain embodiments, glycogen accumulation in a cell were independently reduced by at least 5%, at least 10%, at least 20%, at least 30%, at least 35%, at least 40%, at least 45% or at least 50%. In certain embodiments, cognitive deterioration was reduced by at least 5%, at least 10%, at least 20%, at least 30%, at least 35%, at least 40%, at least 45% or at least 50%. In certain embodiments, ataxia was independently reduced by at least 5%, at least 10%, at least 20%, at least 30%, at least 35%, at least 40%, at least 45% or at least 50%. In certain embodiments, the cell is a neuron. In certain embodiments, the cell is a hepatocyte. In certain embodiments, the cell is a skeletal muscle cell. In certain embodiments, the cell is a cardiac muscle cell.

Certain embodiments provide compounds and compositions described herein for use in therapy. Certain embodiments are drawn to a compound or composition comprising a GYS1-specific inhibitor for use in treating, preventing, delaying the onset, slowing the progression, or ameliorating one or more diseases, disorders, conditions, symptoms, or physiological markers associated with GYS1. Certain embodiments are drawn to a compound or composition for use in treating, preventing, delaying the onset, slowing the progression, or ameliorating a glycogen storage disease or a polyglucosan disease or disorder, or a symptom or physiological marker thereof. In certain embodiments, the polyglucosan disease or disorder is Lafora disease. In certain embodiments, the polyglucosan disease or disorder is adult polyglucosan body disease. In certain embodiments, the disease or disorder is Andersen's disease.

In certain embodiments, the polyglucosan disease or disorder is Pompe disease. In certain embodiments, the GYS1-specific inhibitor is a nucleic acid, peptide, antibody, small molecule or other agent capable of inhibiting the expression or activity of the GYS1. In certain embodiments, the GYS1-specific inhibitor is an antisense compound or an oligomeric compound targeted to GYS1. In certain embodiments, the GYS1-specific inhibitor is oligonucleotide targeted to GYS1. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded.

Certain embodiments are drawn to a compound or composition comprising a GYS1-specific inhibitor for use in reducing seizures, decreasing myoclonus or muscle spasms, alleviating difficulty in walking, reducing, preventing the onset of, or treating dementia, alleviating difficulties in speech, reducing or preventing the onset of visual hallucinations, treating, reducing or preventing the onset of progressive neurologic degeneration, treating, reducing, or preventing the onset of damage to nerves that control bladder function, lessening hypotonia, improving muscle tone, reducing or preventing the onset of an enlarged liver, reducing or preventing the onset of heart defects, reducing or preventing the accumulation of polyglucosan bodies in a cell. reducing or preventing the accumulation of lafora bodies in a cell, reducing glycogen accumulation in a cell, improving or preventing cognitive deterioration, and reducing ataxia, or a combination thereof, in an individual. In certain embodiments, administering the compound or composition reduces seizures in the individual. In certain embodiments, administering the compound or composition decreases myoclonus or muscle spasms in the individual. In certain embodiments, administering the compound or composition alleviates difficulty in walking in the individual. In certain embodiments, administering the compound or composition reduces, prevents the onset of, or treats dementia in the individual. In certain embodiments, administering the compound or composition alleviates difficulties in speech in the individual. In certain embodiments, administering the compound or composition reduces or prevents the onset of visual hallucinations in the individual. In certain embodiments, administering the compound or composition treats, reduces or prevents the onset of progressive neurologic degeneration in the individual. In certain embodiments, administering the compound or composition treats, reduces, or prevents the onset of damage to nerves that control bladder function in the individual. In certain embodiments, administering the compound or composition treats, reduces, or prevents hypotonia in the individual. In certain embodiments, administering the compound or composition improves muscle tone in the individual. In certain embodiments, administering the compound or composition reduces or prevents the onset of an enlarged liver in the individual. In certain embodiments, administering the compound or composition reduces or prevents the onset of heart defects in the individual. In certain embodiments, administering the compound or composition treats, reduces or prevents the onset of polyglucosan bodies in a cell in the individual. In certain embodiments, administering the compound or composition treats, reduces or prevents the onset of lafora bodies in a cell in the individual. In certain embodiments, administering the compound or composition treats, reduces or prevents the onset of glycogen accumulation in a cell in the individual. In certain embodiments, the cell is a neuron. In certain embodiments, the cell is a hepatocyte. In certain embodiments, the cell is a skeletal muscle cell. In certain embodiments, the cell is a cardiac muscle cell. In certain embodiments, administering the compound or composition improves or prevents cognitive deterioration. In certain embodiments, administering the compound or composition treats, reduces ataxia in the individual. In certain embodiments, the individual is identified as having, or at risk of having a disease, disorder, condition, symptom, or physiological marker associated with a glycogen storage disease or a polyglucosan disease or disorder. In certain embodiments, the polyglucosan disease or disorder is Lafora disease. In certain embodiments, the polyglucosan disease or disorder is adult polyglucosan body disease. In certain embodiments, the disease or disorder is Andersen's disease. In certain embodiments, the polyglucosan disease or disorder is Pompe disease. In certain embodiments, the individual is human. In certain embodiments, the GYS1-specific inhibitor is a nucleic acid, peptide, antibody, small molecule or other agent capable of inhibiting the expression or activity of the GYS1. In certain embodiments, the GYS1-specific inhibitor is an antisense compound or an oligomeric compound targeted to GYS1. In certain embodiments, the GYS1-specific inhibitor is oligonucleotide targeted to GYS1. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded.

Certain embodiments are drawn to the use of compounds or compositions described herein for the manufacture or preparation of a medicament for therapy. Certain embodiments are drawn to the use of a compound or composition as described herein in the manufacture or preparation of a medicament for treating, preventing, delaying the onset, slowing progression, or ameliorating one or more diseases, disorders, conditions, symptoms, or physiological markers associated with GYS1. In certain embodiments, the compound or composition as described herein is used in the manufacture or preparation of a medicament for treating, ameliorating, delaying or preventing a glycogen storage disease or a polyglucosan disease or disorder. In certain embodiments, the polyglucosan disease or disorder is Lafora disease. In certain embodiments, the polyglucosan disease or disorder is adult polyglucosan body disease. In certain embodiments, the disease or disorder is Andersen's disease. In certain embodiments, the polyglucosan disease or disorder is Pompe disease. In certain embodiments, the compound or composition comprises a nucleic acid, peptide, antibody, small molecule or other agent capable of inhibiting the expression or activity of GYS1. In certain embodiments, the compound or composition comprises an antisense compound or an oligomeric compound targeted to GYS1. In certain embodiments, the compound or composition comprises an oligonucleotide targeted to GYS1. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound or composition comprising a modified oligonucleotide can be single-stranded. In certain embodiments, the compound or composition comprising a modified oligonucleotide can be double-stranded.

Certain embodiments are drawn to the use of a compound or composition for the manufacture or preparation of a medicament for reducing seizures, decreasing myoclonus or muscle spasms, alleviating difficulty in walking, reducing, preventing the onset of, or treating dementia, alleviating difficulties in speech, reducing or preventing the onset of visual hallucinations, treating, reducing or preventing the onset of progressive neurologic degeneration, treating, reducing, or preventing the onset of damage to nerves that control bladder function, lessening hypotonia, improving muscle tone, reducing or preventing the onset of an enlarged liver, reducing or preventing the onset of heart defects, reducing or preventing the accumulation of polyglucosan bodies in a cell. reducing or preventing the accumulation of lafora bodies in a cell, reducing glycogen accumulation in a cell, improving or preventing cognitive deterioration, and reducing ataxia, or a combination thereof, in an individual having or at risk of having a glycogen storage disease or a polyglucosan disease or disorder. In certain embodiments, the cell is a neuron. In certain embodiments, the cell is a hepatocyte. In certain embodiments, the cell is a skeletal muscle cell. In certain embodiments, the cell is a cardiac muscle cell. Certain embodiments are drawn to use of a compound or composition in the manufacture or preparation of a medicament for reducing seizures in the individual. Certain embodiments are drawn to use of a compound or composition in the manufacture or preparation of a medicament for decreasing myoclonus or muscle spasms in the individual. Certain embodiments are drawn to use of a compound or composition in the manufacture or preparation of a medicament for alleviating difficulty in walking in the individual. Certain embodiments are drawn to use of a compound or composition in the manufacture or preparation of a medicament for reducing, preventing the onset of, or treating dementia in the individual. Certain embodiments are drawn to use of a compound or composition in the manufacture or preparation of a medicament alleviating difficulties in speech in the individual. Certain embodiments are drawn to use of a compound or composition in the manufacture or preparation of a medicament reducing or preventing the onset of visual hallucinations in the individual. Certain embodiments are drawn to use of a compound or composition in the manufacture or preparation of a medicament treating, reducing or preventing the onset of progressive neurologic degeneration in the individual. Certain embodiments are drawn to the use of a compound or composition in the manufacture or preparation of a medicament for treating, reducing, or preventing the onset of damage to nerves that control bladder function in the individual. Certain embodiments are drawn to the use of a compound or composition in the manufacture or preparation of a medicament for treating, reducing, or preventing hypotonia in the individual. Certain embodiments are drawn to the use of a compound or composition in the manufacture or preparation of a medicament for improving muscle tone in the individual. Certain embodiments are drawn to the use of a compound or composition in the manufacture or preparation of a medicament for treating, reducing, or preventing the onset of an enlarged liver in the individual. Certain embodiments are drawn to the use of a compound or composition in the manufacture or preparation of a medicament for treating, reducing, or preventing the onset of heart defects in the individual. Certain embodiments are drawn to the use of a compound or composition in the manufacture or preparation of a medicament for treating, reducing, or preventing the onset of polyglucosan bodies in a cell in the individual. Certain embodiments are drawn to the use of a compound or composition in the manufacture or preparation of a medicament for treating, reducing, or preventing the onset of lafora bodies in the individual. Certain embodiments are drawn to the use of a compound or composition in the manufacture or preparation of a medicament for treating, reducing, or preventing the onset of glycogen accumulation in the individual. Certain embodiments are drawn to use of a compound or composition in the manufacture or preparation of a medicament reducing ataxia in the individual. In certain embodiments, the cell is a neuron. In certain embodiments, the cell is a hepatocyte. In certain embodiments, the cell is a skeletal muscle cell. In certain embodiments, the cell is a cardiac muscle cell. In certain embodiments, the compound or composition comprises a nucleic acid, peptide, antibody, small molecule or other agent capable of inhibiting the expression or activity of the GYS1. In certain embodiments, the compound or composition comprises an antisense compound or an oligomeric compound targeted to GYS1. In certain embodiments, the compound or composition comprises an oligonucleotide targeted to GYS1. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound or composition comprising a modified oligonucleotide can be single-stranded. In certain embodiments, the compound or composition comprising a modified oligonucleotide can be double-stranded.

In any of the foregoing methods or uses, the compound or composition can comprise an antisense compound targeted to GYS1. In certain embodiments, the compound comprises an oligonucleotide, for example an oligonucleotide consisting of 8 to 80 linked nucleosides, 10 to 30 linked nucleosides, 12 to 30 linked nucleosides, or 20 linked nucleosides. In certain embodiments, the oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar. In certain embodiments, the compound can comprise a modified oligonucleotide 12 to 80 linked nucleosides in length and having a nucleobase sequence comprising the nucleobase sequences of any one of SEQ ID NOs: 10-76. In certain embodiments, the compound is an antisense compound or oligomeric compound. In certain embodiments, the compound is single-stranded. In certain embodiments, the compound is double-stranded. In certain embodiments, the modified oligonucleotide is 12 to 30 linked nucleosides in length. In certain embodiments, the compounds or compositions disclosed herein further comprise a pharmaceutically acceptable carrier or diluent.

In any of the foregoing methods or uses, the compound or composition comprises or consists of a modified oligonucleotide 12 to 30 linked nucleosides in length, wherein the modified oligonucleotide comprises:

a gap segment consisting of linked 2'-deoxynucleosides;
a 5' wing segment consisting of linked nucleosides; and
a 3' wing segment consisting of linked nucleosides;

wherein the gap segment is positioned between the 5' wing segment and the 3' wing segment and wherein each nucleoside of each wing segment comprises a modified sugar.

In any of the foregoing methods or uses, the compound or composition can be administered parenterally. For example, in certain embodiments the compound or composition can be administered through injection or infusion. Parenteral administration includes subcutaneous administration, intravenous administration, intramuscular administration, intraarterial administration, intraperitoneal administration, or intracranial administration. In certain embodiments, the compound or composition is co-administered with a second agent. In certain embodiments, the compound or composition and the second agent are administered concomitantly.

Certain Compounds

In certain embodiments, compounds described herein are antisense compounds. In certain embodiments, the antisense compound comprises or consists of an oligomeric compound. In certain embodiments, the oligomeric compound comprises a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, compounds are double-stranded. Such double-stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, compound comprises a conjugate group. In certain embodiments, each modified oligonucleotide is 12-30 linked nucleosides in length.

In certain embodiments, compounds are double-stranded. Such double-stranded compounds comprise a first oligomeric compound having a region complementary to a target nucleic acid and a second oligomeric compound having a region complementary to the first oligomeric compound. The first oligomeric compound of such double stranded compounds typically comprises or consists of a modified oligonucleotide. The oligonucleotide of the second oligomeric compound of such double-stranded compound may be modified or unmodified. The oligomeric compounds of double-stranded compounds may include non-complementary overhanging nucleosides.

Examples of single-stranded and double-stranded compounds include but are not limited to oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 10 to 30 linked subunits in length. In certain embodiments, compound described herein comprises an oligonucleotide is 12 to 30 linked subunits in length. In certain embodiments, compound described herein comprises an oligonucleotide is 12 to 22 linked subunits in length. In certain embodiments, compound described herein comprises an oligonucleotide is 14 to 30 linked subunits in length. In certain embodiments, compound described herein comprises an oligonucleotide is 14 to 20 linked subunits in length. In certain embodiments, compound described herein comprises an oligonucleotide is 15 to 30 linked subunits in length. In certain embodiments, compound described herein comprises an oligonucleotide is 15 to 20 linked subunits in length. In certain embodiments, compound described herein comprises an oligonucleotide is 16 to 30 linked subunits in length. In certain embodiments, compound described herein comprises an oligonucleotide is 16 to 20 linked subunits in length. In certain embodiments, compound described herein comprises an oligonucleotide is 17 to 30 linked subunits in length. In certain embodiments, compound described herein comprises an oligonucleotide is 17 to 20 linked subunits in length. In certain embodiments, compound described herein comprises an oligonucleotide is 18 to 30 linked subunits in length. In certain embodiments, compound described herein comprises an oligonucleotide is 18 to 21 linked subunits in length. In certain embodiments, compound described herein comprises an oligonucleotide is 18 to 20 linked subunits in length. In certain embodiments, compound described herein comprises an oligonucleotide is 20 to 30 linked subunits in length. In other words, such oligonucleotides are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the linked subunits are nucleotides, nucleosides, or nucleobases.

In certain embodiments, compounds may be shortened or truncated. For example, a single subunit may be deleted from the 5' end (5' truncation), or alternatively from the 3' end (3' truncation). A shortened or truncated compound targeted to a GYS1 nucleic acid may have two subunits deleted from the 5' end, or alternatively may have two subunits deleted from the 3' end, of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively to the 3' end (3' addition), of the compound. Alternatively, the added subunits may be dispersed throughout the compound.

It is possible to increase or decrease the length of a compound, such as an oligonucleotide, and/or introduce mismatch bases without eliminating activity (Woolf et al. (Proc. Natl. Acad. Sci. USA 89:7305-7309, 1992; Gautschi et al. *J. Natl. Cancer Inst.* 93:463-471, March 2001; Maher and Dolnick *Nuc. Acid. Res.* 16:3341-3358, 1988). However, seemingly small changes in oligonucleotide sequence, chemistry and motif can make large differences in one or more of the many properties required for clinical development (Seth et al. *J. Med. Chem.* 2009, 52, 10; Egli et al. *J. Am. Chem. Soc.* 2011, 133, 16642).

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics.

In certain embodiments, a double-stranded compound comprises a first strand comprising the nucleobase sequence complementary to a target region of a GYS1 nucleic acid and a second strand. In certain embodiments, the double-stranded compound comprises ribonucleotides in which the first strand has uracil (U) in place of thymine (T) and is complementary to a target region. In certain embodiments, a double-stranded compound comprises (i) a first strand comprising a nucleobase sequence complementary to a target region of a GYS1 nucleic acid, and (ii) a second strand. In certain embodiments, the double-stranded compound comprises one or more modified nucleotides in which the 2' position in the sugar contains a halogen (such as fluorine group; 2'-F) or contains an alkoxy group (such as a methoxy group; 2'-OMe). In certain embodiments, the double-stranded compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the double-stranded compound comprises one or more linkages between adjacent nucleotides other than a naturally-occurring phosphodiester linkage. Examples of such linkages include phosphoramide, phosphorothioate, and phosphorodithioate linkages. The double-stranded compounds may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000. In certain embodiments, the first strand of the double-stranded compound is an siRNA guide strand and the second strand of the double-stranded compound is an siRNA passenger strand. In certain embodiments, the second strand of the double-stranded compound is complementary to the first strand. In certain embodiments, each strand of the double-stranded compound consists of 16, 17, 18, 19, 20, 21, 22, or 23 linked nucleosides.

In certain embodiments, a single-stranded compound described herein can comprise any of the oligonucleotide sequences targeted to GYS1 described herein. In certain embodiments, such a single-stranded compound is a single-stranded RNAi (ssRNAi) compound. In certain embodiments, a ssRNAi compound comprises the nucleobase sequence complementary to a target region of a GYS1 nucleic acid. In certain embodiments, the ssRNAi compound comprises ribonucleotides in which uracil (U) is in place of thymine (T). In certain embodiments, ssRNAi compound comprises a nucleobase sequence complementary to a target region of a GYS1 nucleic acid. In certain embodiments, a ssRNAi compound comprises one or more modified nucleotides in which the 2' position in the sugar contains a halogen (such as fluorine group; 2'-F) or contains an alkoxy group (such as a methoxy group; 2'-OMe). In certain embodiments, a ssRNAi compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the ssRNAi compound. In certain embodiments, the ssRNAi compound comprises one or more linkages between adjacent nucleotides other than a naturally-occurring phosphodiester linkage. Examples of such linkages include phosphoramide, phosphorothioate, and phosphorodithioate linkages. The ssRNAi compounds may also be chemically modified nucleic acid molecules as taught in U.S. Pat. No. 6,673,661. In other embodiments, the ssRNAi contains a capped strand, as disclosed, for example, by WO 00/63364, filed Apr. 19, 2000. In certain embodiments, the ssRNAi compound consists of 16, 17, 18, 19, 20, 21, 22, or 23 linked nucleosides.

In certain embodiments, compounds described herein comprise modified oligonucleotides. Certain modified oligonucleotides have one or more asymmetric center and thus give rise to enantiomers, diastereomers, and other stereoisomeric configurations that may be defined, in terms of absolute stereochemistry, as (R) or (S), as a or β such as for sugar anomers, or as (D) or (L) such as for amino acids etc. Included in the modified oligonucleotides provided herein are all such possible isomers, including their racemic and optically pure forms, unless specified otherwise. Likewise, all cis- and trans-isomers and tautomeric forms are also included.

Certain Mechanisms

In certain embodiments, compounds described herein comprise or consist of modified oligonucleotides. In certain embodiments, compounds described herein are antisense compounds. In certain embodiments, such antisense compounds comprise oligomeric compounds. In certain embodiments, compounds described herein are capable of hybridizing to a target nucleic acid, resulting in at least one antisense activity. In certain embodiments, compounds described herein selectively affect one or more target nucleic acid. Such selective compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain such embodiments, the target nucleic acid is selected from: an mRNA and a pre-mRNA, including intronic, exonic and untranslated regions. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

Human gene sequences that encode GYS1 include, without limitation, the following gene sequences: RefSeqNo. NM_002103.4 (SEQ ID NO: 2), RefSeqNo. NM_001161587.1 (SEQ ID NO: 3), RefSeqNo. NR_027763.1 (SEQ ID NO: 4), RefSeqNo. AK303712.1 (SEQ ID NO: 5), and the complement of RefSeqNo. NC_000019.10 truncated from nucleotides 48965001 to 48996000 (SEQ ID NO: 6).

Hybridization

In some embodiments, hybridization occurs between a compound disclosed herein and a GYS1 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a GYS1 nucleic acid.

Complementarity

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a GYS1 nucleic acid may be tolerated provided that the compound remains able to specifically hybridize to a target nucleic acid. Moreover, a compound may hybridize over one or more segments of a GYS1 nucleic acid such that intervening or adjacent segments are not involved in the hybridization event (e.g., a loop structure, mismatch or hairpin structure).

In certain embodiments, the compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a GYS1 nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of a compound with a region of a target nucleic acid can be determined routinely using BLAST programs (basic local alignment search tools) and PowerBLAST programs known in the art (Altschul et al., *J. Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e. 100% complementary) to a target nucleic acid, or specified portion thereof. For example, a compound may be fully complementary to a GYS1 nucleic acid, or a target region, or a target segment or target sequence thereof. As used herein, "fully complementary" means each nucleobase of a compound is capable of precise base pairing with the corresponding nucleobases of a target nucleic acid. For example, a 20 nucleobase compound is fully complementary to a target sequence that is 400 nucleobases long, so long as there is a corresponding 20 nucleobase portion of the target nucleic acid that is fully complementary to the compound. Fully complementary can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e. linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a GYS1 nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a GYS1 nucleic acid, or specified portion thereof.

In certain embodiments, compounds described herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of a compound. In certain embodiments, the compounds are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

Identity

The compounds provided herein may also have a defined percent identity to a particular nucleotide sequence, SEQ ID NO, or compound represented by a specific Isis number, or portion thereof. In certain embodiments, compounds described herein are antisense compounds or oligomeric compounds. In certain embodiments, compounds described herein are modified oligonucleotides. As used herein, a compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of an compound is calculated according to the number of bases that have identical base pairing relative to the sequence to which it is being compared.

In certain embodiments, compounds described herein, or portions thereof, are, or are at least, 70%, 75%, 80%, 85%, 90%, 91%, 92%, 93%, 94%, 95%, 96%, 97%, 98%, 99% or 100% identical to one or more of the compounds or SEQ ID NOs, or a portion thereof, disclosed herein. In certain embodiments, compounds described herein are about 70%, 75%, 80%, 85%, 90%, 91%, 92%, 93%, 94%, 95%, 96%, 97%, 98%, or 99% identical, or any percentage between such values, to a particular nucleotide sequence, SEQ ID NO, or compound represented by a specific Isis number, or portion thereof, in which the compounds comprise an oligonucleotide having one or more mismatched nucleobases. In certain such embodiments, the mismatch is at position 1, 2, 3, 4, 5, 6, 7, 8, 9, 10, 11, or 12 from the 5'-end of the oligonucleotide. In certain such embodiments, the mismatch is at position 2, 3, 4, 5, 6, 7, 8, 9, 10, 11, or 12 from the 3'-end of the oligonucleotide.

In certain embodiments, compounds described herein are antisense compounds. In certain embodiments, a portion of the compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, compounds described herein are oligonucleotides. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Certain Modified Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Modified Nucleosides

Modified nucleosides comprise a modified sugar moiety or a modified nucleobase or both a modified sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for linearly non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted nucleoside or 2'-non-bicyclic modified nucleoside comprises a sugar moiety comprising a linear 2'-substituent group selected from: F, NH$_2$, N$_3$, OCF$_3$, OCH$_3$, O(CH$_2$)$_3$NH$_2$, CH$_2$CH=CH$_2$, OCH₂CH=CH₂, OCH₂CH₂OCH₃, O(CH₂)₂SCH₃, O(CH₂)₂ON($R_m$)($R_n$), O(CH₂)₂O(CH₂)₂N(CH₃)₂, and N-substituted acetamide (OCH₂C(=O)—N($R_m$)($R_n$)), where each $R_m$ and $R_n$ is, independently, H, an amino protecting group, or substituted or unsubstituted $C_1$-$C_{10}$ alkyl.

In certain embodiments, a 2'-substituted nucleoside or 2'-non-bicyclic modified nucleoside comprises a sugar moiety comprising a linear 2'-substituent group selected from: F, OCF₃, OCH₃, OCH₂CH₂OCH₃, O(CH₂)₂SCH₃, O(CH₂)₂ON(CH₃)₂, O(CH₂)₂O(CH₂)₂N(CH₃)₂, and OCH₂C(=O)—N(H)CH₃ ("NMA").

In certain embodiments, a 2'-substituted nucleoside or 2'-non-bicyclic modified nucleoside comprises a sugar moiety comprising a linear 2'-substituent group selected from: F, OCH₃, and OCH₂CH₂OCH₃.

Nucleosides comprising modified sugar moieties, such as non-bicyclic modified sugar moieties, are referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH₂-2', 4'-(CH₂)₂-2', 4'-(CH₂)₃-2', 4'-CH₂—O-2' ("LNA"), 4'-CH₂—S-2', 4'-(CH₂)₂—O-2' ("ENA"), 4'-CH(CH₃)—O-2' (referred to as "constrained ethyl" or "cEt" when in the S configuration), 4'-CH₂—O—CH₂-2', 4'-CH₂—N(R)-2', 4'-CH(CH₂OCH₃)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. 7,741,457, and Swayze et al., U.S. Pat. No. 8,022,193), 4'-C(CH₃)(CH₃)—O-2' and analogs thereof (see, e.g., Seth et al., U.S. Pat. No. 8,278,283), 4'-CH₂—N(OCH₃)-2' and analogs thereof (see, e.g., Prakash et al., U.S. Pat. No. 8,278,425), 4'-CH₂—O—N(CH₃)-2' (see, e.g., Allerson et al., U.S. Pat. No. 7,696,345 and Allerson et al., U.S. Pat. No. 8,124,745), 4'-CH₂—C(H)(CH₃)-2' (see, e.g., Zhou, et al., J. Org. Chem., 2009, 74, 118-134), 4'-CH₂—C(=CH₂)-2' and analogs thereof (see e.g., Seth et al., U.S. Pat. No. 8,278,426), 4'-C($R_a R_b$)—N(R)—O-2', 4'-C($R_a R_b$)—O—N(R)-2', 4'-CH₂—O—N(R)-2', and 4'-CH₂—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —[C($R_a$)($R_b$)]$_n$—, —[C($R_a$)($R_b$)]$_n$—O—, —C($R_a$)=C($R_b$)—, —C($R_a$)=N—, —C(=N$R_a$)—, —C(=O)—, —C(=S)—, —O—, —Si($R_a$)₂—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)₂-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research,* 1997, 25(22), 4429-4443, Albaek et al., *J. Org. Chem.,* 2006, 71, 7731-7740, Singh et al., *Chem. Commun.,* 1998, 4, 455-456; Koshkin et al., *Tetrahedron,* 1998, 54, 3607-3630; Wahlestedt et al., *Proc. Natl. Acad. Sci. U S. A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 20017, 129, 8362-8379; Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. RE44,779; Wengel et al., U.S. Pat. No. 6,794,499, Wengel et al., U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 91999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

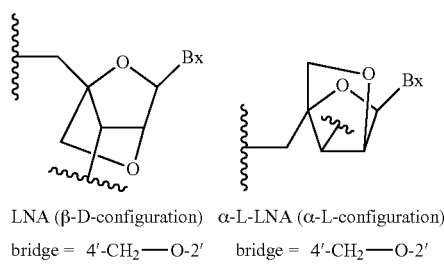

LNA (β-D-configuration)   α-L-LNA (α-L-configuration)
bridge = 4'-CH₂——O-2'     bridge = 4'-CH₂——O-2'

α-L-methyleneoxy (4'-CH₂—O-2') or α-L-LNA bicyclic nucleosides have been incorporated into oligonucleotides that showed antisense activity (Frieden et al., *Nucleic Acids Research,* 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see e.g., Leumann, C J. *Bioorg. & Med. Chem.* 2002, 10, 841-854), fluoro HNA:

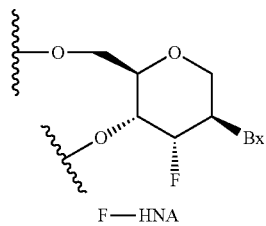

F—HNA ("F-HNA", see e.g., Swayze et al., U.S. Pat. No. 8,088,904; Swayze et al., U.S. Pat. No. 8,440,803; Swayze et al., U.S.; and Swayze et al., U.S. Pat. No. 9,005,906, F-HNA can also be referred to as a F-THP or 3'-fluoro tetrahydropyran), and nucleosides comprising additional modified THP compounds having the formula:

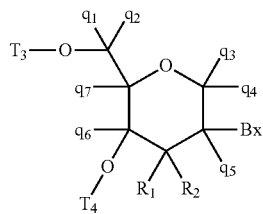

wherein, independently, for each of said modified THP nucleoside: Bx is a nucleobase moiety; $T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

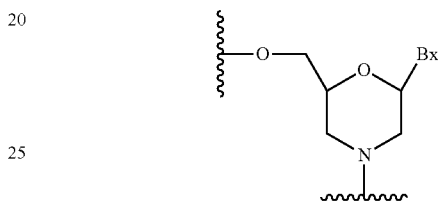

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to compounds described herein.

In certain embodiments, compounds described herein comprise modified oligonucleotides. In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (C≡C—CH3) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403, Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

In certain embodiments, compounds targeted to a GYS1 nucleic acid comprise one or more modified nucleobases. In certain embodiments, the modified nucleobase is 5-methylcytosine. In certain embodiments, each cytosine is a 5-methylcytosine.

Modified Internucleoside Linkages

The naturally occurring internucleoside linkage of RNA and DNA is a 3' to 5' phosphodiester linkage. In certain embodiments, compounds described herein having one or more modified, i.e. non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases.

In certain embodiments, compounds targeted to a GYS1 nucleic acid comprise one or more modified internucleoside linkages. In certain embodiments, the modified internucleoside linkages are phosphorothioate linkages. In certain embodiments, each internucleoside linkage of the compound is a phosphorothioate internucleoside linkage.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH2-N(CH3)-O—CH2-), thiodiester, thionocarbamate (—O—C(=O)(NH)—S—); siloxane (—O—SiH2-O—); and N,N'-dimethylhydrazine (—CH2-N(CH3)-N(CH3)-). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH2-N(CH3)-O-5'), amide-3 (3'-CH2-C(=O)—N(H)-5'), amide-4 (3'-CH2-N(H)—C(=O)-5'), formacetal (3'-O—CH2-O-5'), methoxypropyl, and thioformacetal (3'-S—CH2-O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH2 component parts.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosponate linkages. In certain embodiments, oligonucleotides having a gapmer nucleoside motif comprise a linkage motif comprising all phosphorothioate linkages except for one or two methylphosponate linkages. In certain embodiments, one methylphosponate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

B. Certain Motifs

In certain embodiments, compounds described herein comprise oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, compounds described herein comprise oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified oligonucleotide comprises the same 2'-modification.

2. Certain Nucleobase Motifs

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, compounds described herein comprise oligonucleotides. In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

C. Certain Modified Oligonucleotides

In certain embodiments, compounds described herein comprise modified oligonucleotides. In certain embodiments, the above modifications (sugar, nucleobase, internucleoside linkage) are incorporated into a modified oligonucleotide. In certain embodiments, modified oligonucleotides are characterized by their modification, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

In certain embodiments, the present invention provides pharmaceutical compositions comprising one or more compounds or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compound and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

A compound described herein targeted to a GYS1 nucleic acid can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a compound targeted to a GYS1 nucleic acid and a pharmaceutically acceptable diluent. In certain embodiments, the pharmaceutically acceptable diluent is water. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound.

In certain embodiments, the compounds or compositions further comprise a pharmaceutically acceptable carrier or diluent.

Advantages of Certain Embodiments

Provided herein, for the first time, are methods and compositions for the modulation of a GYS1 nucleic acid that can treat, delay, prevent and/or ameliorate Lafora disease, or a physiological marker thereof. In a particular embodiment, for the first time, GYS1 inhibitors (e.g., oligonucleotides targeting a nucleic acid encoding GYS1) are provided for decreasing seizures, decreasing myoclonus or muscle spasms, alleviating difficulty in walking, reducing, preventing the onset of or treating dementia, alleviating difficulties in speech, reducing or preventing the onset of visual hallucinations, treating, reducing or preventing the onset of progressive neurologic degeneration, reducing ataxia, or a combination thereof in an animal.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Mouse GYS1 in B16-F10 Cells

Three hundred antisense oligonucleotides were screened in B16-F10 cells. The studies described below are a representative of these extensive experiments.

Antisense oligonucleotides were designed targeting a GYS1 nucleic acid and were tested for their effects on GYS1 mRNA in vitro. Cultured B16-F10 cells were transfected using electroporation with 7,000 nM antisense oligonucleotide. After a treatment period of approximately 24 hours, RNA was isolated from the cells and GYS1 mRNA levels were measured by quantitative real-time PCR. Mouse primer probe set RTS4382 (forward sequence TGATGAAGAGAGCCATCTTTGC, designated herein as SEQ ID NO: 7; reverse sequence AGGAGTCGTCCAGCATGTTGT, designated herein as SEQ ID NO: 8; probe sequence ACTCAGCGGCAGTCTTTCCCACCA, designated herein as SEQ ID NO: 9) was used to measure mRNA levels. GYS1 mRNA levels were adjusted according to total RNA content, as measured by RIBOGREEN®. Results are presented as percent inhibition of GYS1, relative to untreated control cells.

The chimeric antisense oligonucleotides in the Table below were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (denoted herein as 's') and phosphate ester linkages (denoted herein as 'o'). The linkage chemistry is denoted at 'soooossssssss-sooss'. All cytosine residues throughout each gapmer are 5-methylcytosines.

"Start site" indicates the 5'-most nucleoside to which the gapmer is targeted in the mouse genomic sequence. "Stop site" indicates the 3'-most nucleoside to which the gapmer is targeted mouse genomic sequence. Each gapmer listed in the Tables below is targeted to the mouse GYS1 genomic sequence, designated herein as SEQ ID NO: 1 (RefSeq No. NC_000073.6 truncated from nucleotides 45432001 to 45460000).

TABLE 1

Inhibition of mouse GYS1 mRNA by 5-10-5 MOE gapmers targeting SEQ ID NO: 1

| ISIS NO | SEQ ID NO: 1 Start Site | SEQ ID NO: 1 Stop Site | Sequence | % inhibition | SEQ ID NO |
|---|---|---|---|---|---|
| 648122 | 2870 | 2889 | CCGACTCAGGTAGGGTGAGC | 58 | 10 |
| 648127 | 2963 | 2982 | CTTGGTGACCGGTAGAGTTA | 21 | 11 |
| 648130 | 3042 | 3061 | GAGAGGCATGGCTACTGCGG | 68 | 12 |
| 648131 | 3047 | 3066 | CGGCTGAGAGGCATGGCTAC | 45 | 13 |
| 648135 | 3083 | 3102 | TCTTCCAATCCTGGAAGCGA | 8 | 14 |
| 648154 | 4596 | 4615 | ATGGTCCCACCAGATAGTAG | 78 | 15 |
| 648155 | 4601 | 4620 | CGTGTATGGTCCCACCAGAT | 73 | 16 |
| 648194 | 8013 | 8032 | AGGTGTTGAGCCTCGATTGC | 45 | 17 |
| 648222 | 12632 | 12651 | TGACTGTATTGGCTGTGTCC | 57 | 18 |
| 648223 | 12637 | 12656 | CTCCTTGACTGTATTGGCTG | 57 | 19 |
| 648226 | 12658 | 12677 | GTAGAGCTTCCTCCCAAATT | 39 | 20 |
| 648258 | 19754 | 19773 | CCTCCGATCCAGAATGTAAA | 24 | 21 |
| 648267 | 19884 | 19903 | ACTTCCAATCTAGCAAGTCC | 28 | 22 |
| 648291 | 23125 | 23144 | TCCCGTGGCTCTTCCTCATC | 11 | 23 |
| 648298 | 23240 | 23259 | TGTGGAGGAGGAACAGGAGG | 0 | 24 |
| 648299 | 23247 | 23266 | TGCCACCTGTGGAGGAGGAA | 22 | 25 |
| 648302 | 23284 | 23303 | CTGGAGGGCCCAGTGTCCAC | 45 | 26 |
| 648303 | 23289 | 23308 | GTGAGCTGGAGGGCCCAGTG | 32 | 27 |
| 648306 | 23406 | 23425 | CATAGGCCCTCTGCGAGAGG | 52 | 28 |
| 648307 | 23411 | 23430 | ATCTGCATAGGCCCTCTGCG | 52 | 29 |
| 648310 | 23426 | 23445 | TTCAGGCACCCTCCCATCTG | 53 | 30 |
| 648311 | 23447 | 23466 | ACTCAAGAGTCTGGAGTGGG | 26 | 31 |
| 648314 | 23502 | 23521 | GGCTGGAGTGTCTGAAACAG | 64 | 32 |
| 648315 | 23513 | 23532 | TGGAGCTCAAGGGCTGGAGT | 23 | 33 |
| 648318 | 23555 | 23574 | CCAAGAAAGGCACGGCGGCG | 74 | 34 |
| 648319 | 23597 | 23616 | CTGGAGACTCCAGATCAGTG | 50 | 35 |
| 648322 | 23638 | 23657 | AAACAATGGCAGATGCCTGG | 40 | 36 |
| 648323 | 23659 | 23678 | CCTAAAACCTCTGGCATTGA | 42 | 37 |
| 648326 | 23683 | 23702 | CCTGGAAGCCAATAAACCAG | 64 | 38 |
| 648327 | 23690 | 23709 | GCCACACGCCTGGAAGCCAAT | 76 | 39 |
| 648330 | 23774 | 23793 | GCCACACAGAATCCAACATG | 80 | 40 |
| 648331 | 23781 | 23800 | TCGGGAAGCCACACAGAATC | 34 | 41 |
| 648334 | 23813 | 23832 | CCTGAAATGTCCTAACTCTG | 49 | 42 |
| 648335 | 23819 | 23838 | TTAATCCCTGAAATGTCCTA | 21 | 43 |
| 648338 | 23870 | 23889 | AATCTGTCGACAGAGCTACT | 72 | 44 |
| 648339 | 23877 | 23896 | GACAAGCAATCTGTCGACAG | 79 | 45 |
| 648342 | 23940 | 23959 | TGTGTATCACCGCACCAGGT | 65 | 46 |
| 648346 | 24097 | 24116 | GAAATGGAGGACCGTGAGCA | 62 | 47 |
| 648347 | 24165 | 24184 | TGCTCCTTTGAAGAACACAC | 39 | 48 |
| 648350 | 24193 | 24212 | GCAGAAAGGTGTCTGGTCCA | 75 | 49 |
| 648351 | 24196 | 24215 | AAGGCAGAAAGGTGTCTGGT | 30 | 50 |
| 648354 | 24275 | 24294 | TGACAGACATTCTGCCCTCA | 65 | 51 |
| 648355 | 24298 | 24317 | AGTGGGCTGAGCACTTGTGG | 39 | 52 |
| 648359 | 24330 | 24349 | AGCCACTGGGACCCAGAACC | 18 | 53 |
| 648362 | 24408 | 24427 | TTCAAGAAGCCGGTGGGCTC | 45 | 54 |
| 648363 | 24437 | 24456 | GCAGAAAGGCCTCGAGGTAC | 59 | 55 |
| 648371 | 3326 | 3345 | CCCCCCAGGGCCTAGGACGC | 65 | 56 |
| 648375 | 3961 | 3980 | ACAGCATTGAGTCTGCCATC | 60 | 57 |
| 648382 | 5607 | 5626 | TGGCCTGACTGGATGCTGGA | 7 | 58 |
| 648390 | 5778 | 5797 | ATTGATCTAACTCTGTCCCA | 32 | 59 |
| 648394 | 6413 | 6432 | ATCCTTGGATTAAAAGAGTG | 42 | 60 |
| 648395 | 6775 | 6794 | GACCAAAACTCCCAGATTTC | 51 | 61 |
| 648399 | 8063 | 8082 | AGCCACATGTAGGGACCACA | 49 | 62 |
| 648402 | 10168 | 10187 | CATGCTTCATTTCTTTATTG | 81 | 63 |
| 648403 | 10380 | 10399 | GGCCCATGCTTCATTTCTTT | 63 | 64 |
| 648406 | 11693 | 11712 | TCAGAGATAGCCAGAGAGAG | 51 | 65 |
| 648407 | 12197 | 12216 | CCCTACTGTCTCATGACTTA | 39 | 66 |
| 648414 | 12895 | 12914 | GAGGCCTCAGCAAATGCCAG | 29 | 67 |
| 648415 | 13163 | 13182 | CCTCCAGCAATGTATTTTAA | 35 | 68 |
| 648418 | 14487 | 14506 | AGGAATCAGAGGGTTCTGTG | 50 | 69 |
| 648419 | 14886 | 14905 | AGCCCTCTCTTTTATGACAA | 13 | 70 |
| 648422 | 16141 | 16160 | ACAAGCTAAAGACTTAAACT | 29 | 71 |
| 648423 | 17471 | 17490 | GATTTGCAAGTGACTCTCAA | 69 | 72 |
| 648426 | 20057 | 20076 | TGGATTCCCTCTGTAGATCA | 59 | 73 |
| 648427 | 20466 | 20485 | TGTCTCTAGCTCTGACAACA | 45 | 74 |
| 648430 | 22024 | 22043 | CCAGATGCTATTTCTAGATT | 88 | 75 |
| 648431 | 22395 | 22414 | ACTGCTGGAGTCCCCAGCAA | 3 | 76 |

Example 2: Dose-Dependent Antisense Inhibition of Mouse GYS1 in B16-F10 Cells

Gapmers from Example 1 exhibiting significant in vitro inhibition of GYS1 mRNA were selected and tested at various doses in B16-F10 cells. Cells were plated at a density of 20,000 cells per well and transfected using electroporation with 0.625 µM, 1.25 µM, 5.00 µM, and 10.0 µM concentrations of antisense oligonucleotide. After a treatment period of approximately 16 hours, RNA was isolated from the cells and GYS1 mRNA levels were measured by quantitative real-time PCR. Mouse primer probe set RTS4382 was used to measure mRNA levels. GYS1 mRNA levels were adjusted according to total RNA content, as measured by RIBOGREEN®. The half maximal inhibitory concentration ($IC_{50}$) of each oligonucleotide is presented. GYS1 mRNA levels were significantly reduced in a dose-dependent manner in antisense oligonucleotide treated cells.

Two antisense oligonucleotides, ISIS 648327 and ISIS 648402 were selected for further experimentation in vivo.

TABLE 2

Dose dependent inhibition by antisense oligonucleotides targeting GYS1

| ISIS No | 625.0 nM | 1250.0 nM | 2500.0 nM | 5000.0 nM | 10000.0 nM | $IC_{50}$ (µM) |
|---|---|---|---|---|---|---|
| 648339 | 19 | 38 | 58 | 77 | 93 | 1.9 |
| 648327 | 32 | 44 | 66 | 82 | 90 | 1.4 |
| 648155 | 18 | 42 | 62 | 76 | 90 | 1.9 |
| 648423 | 12 | 26 | 38 | 64 | 70 | 3.6 |
| 648371 | 38 | 55 | 78 | 82 | 93 | 0.9 |
| 648430 | 4 | 9 | 25 | 31 | 53 | 10.7 |
| 648402 | 53 | 42 | 62 | 84 | 89 | 0.9 |
| 648330 | 35 | 42 | 62 | 74 | 89 | 1.5 |
| 648154 | 21 | 32 | 55 | 69 | 83 | 2.3 |
| 648350 | 21 | 29 | 58 | 70 | 85 | 2.3 |

Example 3: Intracerebroventricular Administration of Antisense Oligonucleotides Against GYS1 mRNA C57BL/6 mice were treated with ISIS oligonucleotides via intracerebroventricular (ICV) administration to a defined mouse brain area, the right lateral ventricle, for the purpose of evaluating the efficacy of ICV dosing in mice.

Treatment

Groups of four C57BL/6 mice each were administered ISIS 648154, ISIS 648155, ISIS 648327, ISIS 648330, ISIS 648339, ISIS 648350, ISIS 648371, or ISIS 648402 at 300 µg delivered as an ICV bolus injection. A control group of 4 mice were similarly treated with PBS. The animals were euthanized after 2 weeks.

RNA Analysis

RNA was extracted from the right hemisphere of the cortex, hippocampus, and the cerebellar sections for real-time PCR analysis of GYS-1 mRNA levels. Murine GYS-1 mRNA levels were measured using the primer probe set RTS4382. Results were calculated as percent inhibition of murine GYS-1 mRNA expression compared to the control and are presented in the Table below. Of the antisense oligonucleotides tested, ISIS 648327 and ISIS 648402 were utilized in further studies.

TABLE 3

Percent inhibition by antisense oligonucleotides targeting GYS1

| ISIS No | Cortex | Hippocampus | Cerebellum |
|---|---|---|---|
| 648154 | 0 | 7 | 24 |
| 648155 | 6 | 0 | 30 |
| 648327 | 60 | 40 | 27 |
| 648330 | 21 | 21 | 33 |
| 648339 | 16 | 0 | 2 |
| 648350 | 24 | 12 | 10 |
| 648371 | 3 | 0 | 21 |
| 648402 | 51 | 21 | 45 |

Example 4: Effect of Antisense Inhibition of GYS1 in Mice Models for Lafora Disease Mutations in the EPM2A gene, encoding a dual-specificity phosphatase (Laforin) or in the EPM2B gene, encoding ubiquitin E3 ligase malin, cause Lafora disease (LD). The phenotype of targeted disruption of the Epm2a or Epm2b murine genes is comparable to the phenotype of human LD resulting from the same genetic defect. Both $Epm2a^{-/-}$ and $Epm2b^{-/-}$ mice show altered motor activity, impaired motor coordination, episodic memory deficit, and myoclonus (Garcia-Cabrero A. M. et al., 2012. J. Neuropathol. Exp. Neurol. 71: 413-421). Neurologic alterations observed in the mutants were comparable and correlated with the accumulation of abundant Lafora bodies in the cerebral cortex, the hippocampus, the basal ganglia, the cerebellum, and the brainstem, suggesting that these inclusions could cause cognitive and behavioral deterioration. Thus, both $Epm2a^{-/-}$ and $Epm2b^{-/-}$ mice exhibit many pathologic aspects seen in patients with Lafora disease and serve as mouse models for the disease.

$Epm2a^{-/-}$ Mice

Treatment

The effects of antisense inhibition of GYS1 were investigated in $Epm2a^{-/-}$ mice. The mice have been previously described (Pedersen, B. A. et al., Ann. Neurol. 74: 297-300, 2013; Turnball, J. et al., PLoS Genet. 7: e1002037 (2011). The mice were randomly divided into 4 groups of 6 mice each. Two groups of mice were injected intracerebroventricularly with 300 µg of ISIS 648327 or ISIS 648402 at 1 month and 2 months of age. A third group of mice were injected intracerebroventricularly with 300 µg of ISIS 676630 (CCTATAGGACTATCCAGGAA, 5-10-5 MOE gapmer with phosphorothioate and phosphate internucleoside linkages and with no known murine target; SEQ ID NO: 77) at 1 month and 2 months of age.

A control group of mice was injected intracerebroventricularly with PBS at 1 month and 2 months of age. The mice were sacrificed at 3 months by cervical dislocation, one cerebral hemisphere was snap-frozen in liquid nitrogen for biochemical analysis; the other was immersed in formalin for histopathology.

RNA Analysis

RNA was extracted from cerebral hemisphere of the mice for RT-PCR analysis of murine GYS1 expression. The data was normalized to GAPDH. The results are presented in the Table below and demonstrate the in vivo inhibition of GYS1 by antisense oligonucleotide.

TABLE 4

In vivo inhibition (% of PBS control) of mouse GYS1 mRNA levels

|  | % |
|---|---|
| Control oligo | 23 |
| ISIS 648327 | 76 |
| ISIS 648402 | 84 |

Protein Analysis

Western blot analysis of murine GYS1 protein expression was quantititated. The results are presented relative to the housekeeping gene, GAPDH, in the Table below and demonstrate the in vivo inhibition of GYS1 protein levels by antisense oligonucleotide.

TABLE 5

Mouse GYS1 protein levels (% relative to GAPDH)

|  | % |
|---|---|
| PBS | 14 |
| Control oligo | 11 |
| ISIS 648327 | 2 |
| ISIS 648402 | 1 |

Glycogen Level Analysis

Lafora bodies were quantified by biochemical measurement of total brain glycogen, as previously described (Turball, J. et al. PLoS Genet. 7: e1002037, 2011). This mice model typically has two-fold increased brain glycogen at 3 months of age. The results are presented in the Table below and demonstrate the effect of inhibition of GYS1 on brain glycogen levels. The data indicates that brain glycogen levels were normalized by both antisense oligonucleotides. Glycogen levels of wild-type mice are also shown for comparison. The PBS and control oligonucleotide groups have high glycogen content, representing the levels in Lafora disease.

TABLE 6

Brain glycogen levels (μmol/g tissue)

| PBS | 8.7 |
|---|---|
| Control oligo | 7.8 |
| ISIS 648327 | 3.4 |
| ISIS 648402 | 2.8 |
| Wild-type | 2.4 |

Lafora Bodies Analysis

Lafora bodies (LB) were visualized by staining diastase-pretreated brain sections with periodic acid-Schiff. In animals treated with ISIS 648327, LB were completely eliminated from all brain regions. In animals treated with ISIS 648402, LB were almost completely eliminated from all brain regions. The data thus demonstrates that antisense inhibition of GYS1 significantly reduced or completely eliminated LB from the brain.

$Epm2b^{-/-}$ Mice

Treatment

The effects of antisense inhibition of GYS1 were investigated in $Epm2b^{-/-}$ mice. The mice have been previously described (Pedersen, B. A. et al., Ann. Neurol. 74: 297-300, 2013; Turnball, J. et al., PLoS Genet. 7: e1002037 (2011). The mice were randomly divided into 3 groups of 6 mice each. One group of mice was injected intracerebroventricularly with 300 μg of ISIS 648327 at 1 month and 2 months of age. A second group of mice were injected intracerebroventricularly with 300 μg of ISIS 676630 at 1 month and 2 months of age. A control group of mice was injected intracerebroventricularly with PBS at 1 month and 2 months of age. The mice were sacrificed at 3 months by cervical dislocation, one cerebral hemisphere was span-frozen in liquid nitrogen for biochemical analysis; the other was immersed in formalin for histopathology.

RNA Analysis

RNA was extracted from cerebral hemisphere of the mice for RT-PCR analysis of murine GYS1 expression. The data was normalized to GAPDH. The results are presented in the Table below and demonstrate the in vivo inhibition of GYS1 by antisense oligonucleotide.

TABLE 7

In vivo inhibition (% of PBS control) of mouse GYS1 mRNA levels

|  | % |
|---|---|
| Control oligo | 17 |
| ISIS 648327 | 56 |

Protein Analysis

Western blot analysis of murine GYS1 protein expression was quantititated. The results are presented relative to the housekeeping gene, GAPDH, in the Table below and demonstrate the in vivo inhibition of GYS1 protein levels by antisense oligonucleotide.

TABLE 8

Mouse GYS1 protein levels (% relative to GAPDH)

|  | % |
|---|---|
| PBS | 42 |
| Control oligo | 34 |
| ISIS 648327 | 6 |

Glycogen Level Analysis

Lafora bodies were quantified by biochemical measurement of total brain glycogen, as previously described (Turball, J. et al. PLoS Genet. 7: e1002037, 2011). The results are presented in the Table below and demonstrate the effect of inhibition of GYS1 on brain glycogen levels. The data indicates that brain glycogen levels were normalized by both antisense oligonucleotides. Glycogen levels of wild-type mice are also shown for comparison. As previously described in DePaoli-Roach et al (J. Biochem. 13: 25372-25381, 2010), the abnormal glycogen accumulation as not as high in in $Epm2b^{-/-}$ mice as in in $Epm2a^{-/-}$ mice.

Example 5: Effect of Antisense Inhibition of GYS1 in Mice Models for Adult Polyglucosan Body Disease The effects of antisense inhibition of GYS1 were investigated in APBD mice or Gbe1 Y329S mice. The mice have been previously described (Akman, O. H. et al., Hum. Mo. Genet. 24: 6801-6810, 2015). The mice were randomly divided into 4 groups. Two groups of mice were injected intracerebroventricularly with 300 μg of ISIS 648402 or ISIS 648327 at 1 month and 2 months of age. A third group of mice were injected intracerebroventricularly with 300 μg of control oligonucleotide ISIS 676630 at 1 month and 2 months of age. Another group of mice was injected intracerebroventricularly with PBS at 1 month and 2 months of age. The mice were sacrificed at 3 months by cervical dislocation, one cerebral hemisphere was span-frozen in liquid nitrogen for biochemical analysis; the other was immersed in formalin for histopathology.

RNA Analysis

RNA was extracted from cerebral hemisphere of the mice for RT-PCR analysis of murine GYS1 expression. The data was normalized to GAPDH. The results are presented in the Table below and demonstrate the in vivo inhibition of GYS1 by antisense oligonucleotide.

TABLE 9

In vivo inhibition (% of PBS control) of mouse GYS1 mRNA levels

|  | % |
|---|---|
| Control oligo | 9 |
| ISIS 648402 | 59 |
| ISIS 648327 | 69 |

Protein Analysis

Western blot analysis of murine GYS1 protein expression was quantititated. The results are presented relative to the housekeeping gene, GAPDH, in the Table below and demonstrate the in vivo inhibition of GYS1 protein levels by antisense oligonucleotide.

TABLE 10

Mouse GYS1 protein levels (% relative to GAPDH)

|  | % |
|---|---|
| PBS | 10.0 |
| Control oligo | 16.0 |
| ISIS 648402 | 0.8 |
| ISIS 648327 | 3.1 |

Glycogen Level Analysis

Lafora bodies were quantified by biochemical measurement of total brain glycogen, as previously described (Turball, J. et al. PLoS Genet. 7: e1002037, 2011). The results are presented in the Table below and demonstrate the effect of inhibition of GYS1 on brain glycogen levels.

TABLE 11

| Brain glycogen levels (μmol/g tissue) | |
|---|---|
| PBS | 1.5 |
| Control oligo | 1.6 |
| ISIS 648402 | 1.1 |
| ISIS 648327 | 0.8 |

Example 6: Effect of Antisense Inhibition of GYS1 in the Treatment of a Glycogen Storage Disease The effects of antisense inhibition of GYS1 were investigated in aged EMP2A (Laforin) knockout mice. Lafora bodies begin to appear in the brain by two months, behavioral abnormalities are detected at 4 months, and by 9 months, the animals have myoclonic seizures, ataxia, and EEG activity (Wang W. et al., Arch. Biochem. Biophys. 457: 264, 2007).

Eight months old Epm2a$^{-/-}$ mice were randomly divided into 3 groups. Two groups of mice were injected intracerebroventricularly with 300 μg of ISIS 648402 or the control oligonucleotide at 8 months, 9.5 months, 11 months, and 12.5 months of age. Another group of mice was injected intracerebroventricularly with PBS at 8 months, 9.5 months, 11 months, and 12.5 months of age. The mice were sacrificed at 14 months by cervical dislocation, one cerebral hemisphere was span-frozen in liquid nitrogen for biochemical analysis; the other was immersed in formalin for histopathology.

RNA Analysis

RNA was extracted from cerebral hemisphere of the mice for RT-PCR analysis of murine GYS1 expression. The data was normalized to GAPDH. The results are presented in the Table below and demonstrate the in vivo inhibition of GYS1 by antisense oligonucleotide.

TABLE 12

In vivo inhibition (% of PBS control) of mouse GYS1 mRNA levels

|  | % |
|---|---|
| Control oligo | 0 |
| ISIS 648327 | 54 |

Protein Analysis

Western blot analysis of murine GYS1 protein expression was quantititated. The results are presented relative to the housekeeping gene, GAPDH, in the Table below and demonstrate the in vivo inhibition of GYS1 protein levels by antisense oligonucleotide.

TABLE 13

Mouse GYS1 protein levels (relative to GAPDH)

|  | % |
|---|---|
| Untreated mice at 8 months | 22.1 |
| Control oligo-treated mice at 14 months | 13.2 |
| ISIS 648327-treated mice at 14 months | 0.50 |

Glycogen Level Analysis

Total brain glycogen levels and Lafora bodies quantification in the hippocampus were measured. Brain tissue of mice at 8 months shows glycogen levels and accumulation of Lafora bodies in the hippocampus, implying a robust phenotype of glycogen storage disease in these mice at that age. The results are presented in the Tables below and demonstrate the effect of inhibition of GYS1 and the significant reduction in Lafora bodies in the hippocampus.

TABLE 14

| Lafora bodies in hippocampus (%) | |
|---|---|
| Untreated mice at 8 months | 7.02 |
| Control oligo-treated mice at 14 months | 8.04 |
| ISIS 648327-treated mice at 14 months | 2.67 |

TABLE 15

| Brain glycogen levels (μmol/g tissue) | |
|---|---|
| Untreated mice at 8 months | 5.9 |
| Control oligo-treated mice at 14 months | 7.5 |
| ISIS 648327-treated mice at 14 months | 3.5 |

What is claimed is:

1. A method of treating Lafora disease in an individual having Lafora disease comprising administering to the individual a compound comprising a modified oligonucleotide consisting of 15 to 30 nucleosides, wherein the modified oligonucleotide has a nucleobase sequence at least 95% complementary to an equal length portion of the nucleobase sequence of any one of SEQ ID NO: 2, SEQ ID NO: 3, SEQ ID NO: 4, or SEQ ID NO: 5, wherein at least one internucleoside linkage of the modified oligonucleotide is a phosphorothioate internucleoside linkage, and wherein Lafora bodies are reduced in a cell in the individual, thereby treating the Lafora disease in the individual.

2. The method of claim 1, wherein the compound is single-stranded.

3. The method of claim 1, wherein the modified oligonucleotide comprises at least one modified nucleobase or at least one modified sugar moiety.

4. The method of claim 3, wherein the at least one modified nucleobase is a 5-methylcytosine.

5. The method of claim 3, wherein the at least one modified sugar moiety is a bicyclic sugar moiety.

6. The method of claim 1, wherein the modified oligonucleotide comprises:
a gap segment consisting of linked deoxynucleosides;
a 5' wing segment consisting of linked nucleosides; and
a 3' wing segment consisting of linked nucleosides;
wherein the gap segment is positioned immediately adjacent to and between the 5' wing segment and the 3' wing segment and wherein each nucleoside of each wing segment comprises a modified sugar.

7. The method of claim 6, wherein the modified sugar moiety of each wing segment is a 2'-O-methoxyethyl, and wherein each cytosine of said modified oligonucleotide is a 5-methylcytosine.

8. The method of claim 5, wherein the bicyclic sugar moiety comprises a 4'-CH($CH_3$)—O-2' bridge or a 4'-($CH_2$)n-O-2' bridge, wherein n is 1 or 2.

9. The method of claim 3, wherein the at least one modified sugar moiety is a non-bicyclic moiety.

10. The method of claim 9, wherein the non-bicyclic moiety is selected from 2'-F, 2'-OMe, and 2'-MOE.

11. The method of claim 1, wherein the modified oligonucleotide comprises at least one modified nucleoside comprising a sugar surrogate.

12. The method of claim 11, wherein the sugar surrogate is selected from morpholino and PNA.

13. The method of claim 1, wherein the modified oligonucleotide is a gapmer.

14. The method of claim 1, wherein the modified oligonucleotide comprises:
a gap segment consisting of 7-12 linked deoxynucleosides;
a 5' wing segment consisting of 1-5 linked nucleosides; and
a 3' wing segment consisting of 1-5 linked nucleosides;
wherein the gap segment is positioned immediately adjacent to and between the 5' wing segment and the 3' wing segment and wherein each nucleoside of each wing segment comprises a modified sugar.

15. The method of claim 1, wherein at least one internucleoside linkage of the modified oligonucleotide is a phosphodiester internucleoside linkage.

16. The method of claim 1, wherein the modified oligonucleotide consists of 15-25, 16-20, 18-22, or 18-20 linked nucleosides.

17. The method of claim 1, wherein the individual is a human.

* * * * *